US010614283B2

United States Patent
He et al.

(10) Patent No.: US 10,614,283 B2
(45) Date of Patent: Apr. 7, 2020

(54) DEVICES WITH PERIPHERAL TASK BAR DISPLAY ZONE AND UNDER-LCD SCREEN OPTICAL SENSOR MODULE FOR ON-SCREEN FINGERPRINT SENSING

(71) Applicant: Shenzhen Goodix Technology Co., Ltd., Shenzhen (CN)

(72) Inventors: Yi He, San Diego, CA (US); Bo Pi, San Diego, CA (US)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 20 days.

(21) Appl. No.: 15/913,869

(22) Filed: Mar. 6, 2018

(65) Prior Publication Data

US 2018/0260602 A1 Sep. 13, 2018

Related U.S. Application Data

(63) Continuation-in-part of application No. 15/708,088, filed on Sep. 18, 2017.

(Continued)

(51) Int. Cl.
*G06K 9/00* (2006.01)
*G06F 3/14* (2006.01)
(Continued)

(52) U.S. Cl.
CPC .......... *G06K 9/0012* (2013.01); *A61B 5/0075* (2013.01); *A61B 5/024* (2013.01);
(Continued)

(58) Field of Classification Search
CPC .. G06K 9/0012; G06K 9/0008; G06K 9/2036; G06K 9/209; G06K 9/0004;
(Continued)

(56) References Cited

U.S. PATENT DOCUMENTS 5,420,936 A 5/1995 Fitzpatrick et al.
5,726,443 A 3/1998 Immega et al.
(Continued)

FOREIGN PATENT DOCUMENTS

CN 101416202 A 4/2009
CN 102411878 A 4/2012
(Continued)

OTHER PUBLICATIONS

Extended European Search Report dated Apr. 1, 2019 for EP Application No. 17743741.5 (13 pages).
(Continued)

*Primary Examiner* — John B Strege
(74) *Attorney, Agent, or Firm* — Perkins Coie LLP

(57) ABSTRACT

Devices or systems with display designs to include both a main display zone and a peripheral display zone that collectively form a seamless contiguous display area for displaying images, content or information over the two zones as a single display area and further allowing for operating the peripheral display zone independently from the main display zone to display certain images, information, or content only on the peripheral display zone even when the main display zone is turned off. In addition to providing display functions separate from or in combination with the display functions by the main display zone, the peripheral display zone based on the disclosed technology can be used to provide for certain sensing functions by including one or more sensors under the display area for the peripheral display zone.

52 Claims, 62 Drawing Sheets

431- Cover glass
433f- modified LCD structure layers 433a to permit light transmission for illuminating the peripheral display zone and for optical sensing
433b- LCD light diffuser layer
433c- LCD lightguide board
433d- LCD reflector film layer
436a- Probe light sources
436b- Task bar light sources under the display
436c- Task bar light sources embedded in the display
490- Backlighting light module for directing illumination light to both the main display zone and the peripheral display zone
621a- Photo detector array
623- Circuit board
951c- Modified window in other layers of the LCD layers 433f
951d- Modified window in the light diffuser 433b
951e- Micro transparent structures in the reflector film 433d

Related U.S. Application Data

(60) Provisional application No. 62/468,337, filed on Mar. 7, 2017.

(51) Int. Cl.

| | | |
|---|---|---|
| *G06F 3/0488* | (2013.01) | |
| *G06F 21/32* | (2013.01) | |
| *G06F 3/042* | (2006.01) | |
| *G06F 3/041* | (2006.01) | |
| *H04L 29/06* | (2006.01) | |
| *G06F 21/83* | (2013.01) | |
| *G06F 3/044* | (2006.01) | |
| *G06K 9/20* | (2006.01) | |
| *A61B 5/145* | (2006.01) | |
| *A61B 5/00* | (2006.01) | |
| *A61B 5/103* | (2006.01) | |
| *G09G 3/34* | (2006.01) | |
| *A61B 5/026* | (2006.01) | |
| *A61B 5/1495* | (2006.01) | |
| *A61B 5/024* | (2006.01) | |
| *A61B 5/1172* | (2016.01) | |

(52) U.S. Cl.
CPC .......... *A61B 5/0261* (2013.01); *A61B 5/1032* (2013.01); *A61B 5/1172* (2013.01); *A61B 5/1495* (2013.01); *A61B 5/14532* (2013.01); *A61B 5/14542* (2013.01); *A61B 5/681* (2013.01); *G06F 3/042* (2013.01); *G06F 3/044* (2013.01); *G06F 3/0412* (2013.01); *G06F 3/0418* (2013.01); *G06F 3/0488* (2013.01); *G06F 3/14* (2013.01); *G06F 21/32* (2013.01); *G06F 21/83* (2013.01); *G06K 9/0004* (2013.01); *G06K 9/0008* (2013.01); *G06K 9/00114* (2013.01); *G06K 9/209* (2013.01); *G06K 9/2036* (2013.01); *G09G 3/3413* (2013.01); *H04L 63/0861* (2013.01); *A61B 2562/043* (2013.01); *G06F 2203/04106* (2013.01); *G06F 2221/2133* (2013.01); *G06K 9/00906* (2013.01); *G06K 9/2018* (2013.01); *G06K 2009/00939* (2013.01); *G09G 2310/04* (2013.01); *G09G 2358/00* (2013.01)

(58) Field of Classification Search
CPC ............ G06K 9/00114; G06K 9/2018; G06K 9/00906; G06K 2009/00939; G09G 3/3413; G09G 2358/00; G09G 2358/04; H04L 63/0861; G06F 21/32; G06F 21/83; G06F 3/044; G06F 3/0418; G06F 3/0412; G06F 3/042; G06F 3/0488; G06F 3/14; G06F 2221/2133; G06F 2203/04106; A61B 2562/043; A61B 5/0261; A61B 5/024; A61B 5/14542; A61B 5/0075; A61B 5/1172; A61B 5/1495; A61B 5/681; A61B 5/14532; A61B 5/1032
See application file for complete search history.

(56) References Cited

U.S. PATENT DOCUMENTS

| | | | |
|---|---|---|---|
| 5,953,441 A | 9/1999 | Setlak | |
| 6,292,576 B1 | 9/2001 | Brownlee | |
| 6,327,376 B1 | 12/2001 | Harkin | |
| 7,535,468 B2 | 5/2009 | Uy | |
| 7,728,959 B2 | 6/2010 | Waldman et al. | |
| 7,751,595 B2 | 7/2010 | Russo et al. | |
| 7,936,907 B2 | 5/2011 | Maurer et al. | |
| 9,829,614 B2 | 11/2017 | Smith et al. | |
| 9,946,375 B2 | 4/2018 | Akhavan et al. | |
| 9,990,533 B2 | 6/2018 | Pi et al. | |
| 2003/0044051 A1 | 3/2003 | Fujieda | |
| 2003/0090650 A1 | 5/2003 | Fujieda | |
| 2003/0190062 A1 | 10/2003 | Noro | |
| 2004/0252867 A1 | 12/2004 | Lan et al. | |
| 2006/0115128 A1 | 6/2006 | Mainguet | |
| 2007/0035843 A1 | 2/2007 | Cassarly | |
| 2007/0109438 A1 | 5/2007 | Duparre et al. | |
| 2007/0147667 A1 | 6/2007 | Sumita et al. | |
| 2007/0211926 A1 | 9/2007 | Shinzaki et al. | |
| 2008/0121442 A1 | 5/2008 | Boer et al. | |
| 2008/0122803 A1 | 5/2008 | Izadi et al. | |
| 2008/0237766 A1 | 10/2008 | Kim | |
| 2009/0021487 A1 | 1/2009 | Tien | |
| 2009/0232367 A1 | 9/2009 | Shinzaki | |
| 2010/0008552 A1 | 1/2010 | Shin et al. | |
| 2010/0113952 A1 | 5/2010 | Raguin et al. | |
| 2010/0321152 A1 | 12/2010 | Argudyaev et al. | |
| 2011/0080348 A1* | 4/2011 | Lin | G06F 1/1626 345/173 |
| 2011/0233383 A1 | 9/2011 | Oku | |
| 2012/0019744 A1 | 1/2012 | Lee | |
| 2012/0069042 A1 | 3/2012 | Ogita et al. | |
| 2012/0105614 A1 | 5/2012 | Wu et al. | |
| 2012/0182266 A1 | 7/2012 | Han | |
| 2013/0051635 A1 | 2/2013 | Wu et al. | |
| 2013/0120760 A1 | 5/2013 | Raguin et al. | |
| 2013/0222282 A1 | 8/2013 | Huang et al. | |
| 2013/0258086 A1 | 10/2013 | Erhart et al. | |
| 2013/0287272 A1 | 10/2013 | Lu et al. | |
| 2014/0016047 A1 | 1/2014 | Hwang et al. | |
| 2014/0036168 A1 | 2/2014 | Ludwig | |
| 2014/0098058 A1 | 4/2014 | Baharav et al. | |
| 2014/0125788 A1 | 5/2014 | Wu | |
| 2014/0133715 A1 | 5/2014 | Ballard | |
| 2014/0168167 A1 | 6/2014 | Chou | |
| 2014/0218327 A1 | 8/2014 | Shi et al. | |
| 2014/0354905 A1 | 12/2014 | Kitchens et al. | |
| 2014/0368764 A1 | 12/2014 | Lee et al. | |
| 2015/0078633 A1 | 3/2015 | Hung | |
| 2015/0220767 A1 | 8/2015 | Yoon et al. | |
| 2016/0004899 A1 | 1/2016 | Pi et al. | |
| 2016/0026844 A1 | 1/2016 | Kim et al. | |
| 2016/0042216 A1 | 2/2016 | Yang et al. | |
| 2016/0092718 A1 | 3/2016 | Jensen et al. | |
| 2016/0104025 A1 | 4/2016 | Thompson et al. | |
| 2016/0132712 A1 | 5/2016 | Yang et al. | |
| 2016/0180146 A1 | 6/2016 | Setterberg et al. | |
| 2016/0224816 A1 | 8/2016 | Smith et al. | |
| 2016/0247010 A1 | 8/2016 | Huang et al. | |
| 2016/0254312 A1 | 9/2016 | Lee | |
| 2016/0266695 A1 | 9/2016 | Bae et al. | |
| 2016/0364036 A1 | 12/2016 | Deng et al. | |
| 2017/0017824 A1 | 1/2017 | Smith et al. | |
| 2017/0083745 A1 | 3/2017 | Goodelle et al. | |
| 2017/0124370 A1 | 5/2017 | He et al. | |
| 2017/0220182 A1 | 8/2017 | Schwartz et al. | |
| 2017/0220838 A1 | 8/2017 | He et al. | |
| 2017/0220842 A1* | 8/2017 | Thompson | G06F 21/81 |
| 2017/0220844 A1 | 8/2017 | Jones et al. | |
| 2017/0270340 A1 | 9/2017 | Gao et al. | |
| 2017/0270342 A1 | 9/2017 | He et al. | |
| 2017/0337412 A1 | 11/2017 | Bhat et al. | |
| 2017/0337413 A1 | 11/2017 | Bhat et al. | |
| 2018/0000500 A1 | 1/2018 | He et al. | |
| 2018/0075283 A1 | 3/2018 | You et al. | |
| 2018/0113512 A1 | 4/2018 | Kang et al. | |
| 2018/0114047 A1 | 4/2018 | Kim et al. | |
| 2018/0017334 A1 | 6/2018 | Pi et al. | |
| 2018/0165494 A1 | 6/2018 | Kim et al. | |
| 2018/0188422 A1 | 7/2018 | Fujii et al. | |

FOREIGN PATENT DOCUMENTS

| | | |
|---|---|---|
| CN | 104155785 A | 11/2014 |
| CN | 204069106 U | 12/2014 |
| CN | 105094443 A | 11/2015 |
| CN | 105184282 A | 12/2015 |
| CN | 107004130 A | 8/2017 |

(56) References Cited

FOREIGN PATENT DOCUMENTS

| EP | 2562683 | A1 | 2/2013 |
|---|---|---|---|
| EP | 3273329 | A1 | 1/2018 |
| TW | 200905578 | A | 2/2009 |
| TW | 201426563 | A | 7/2014 |
| WO | 01/69520 | A2 | 9/2001 |
| WO | 2001/069520 | A3 | 9/2001 |
| WO | 2011110821 | A1 | 9/2011 |
| WO | 2016205832 | A1 | 12/2016 |

OTHER PUBLICATIONS

Extended European Search Report dated Jun. 3, 2019 for EP Application No. 17809591.5 (8 pages).
Partial/Supplementary European Search Report dated May 20, 2019 for EP1875868.4 (14 pages).
Partial/Supplemental European Search Report dated Jun. 5, 2019 for EP17850146.6 (14 pages).
Partial/Supplemental European Search Report dated Jun. 11, 2019.
Office Action dated Feb. 6, 2019 for EP16812652.2.
International Search Report from PCT/CN2017/095908 dated Nov. 7, 2017 (6 pages).
International Search Report from PCT/CN2018/078360 dated May 31, 2018 (4 pages).
International Search Report and Written Opinion from International Application No. PCT/US2016/038445, dated Sep. 30, 2016 (16 pages).
International Search Report from PCT/CN2017/072575 dated Apr. 1, 2017 (4 pages).
International Search Report from PCT/CN2017/083117 dated Aug. 10, 2017 (4 pages).
International Search Report from PCT/CN2018/071400 dated Mar. 29, 2018 (5 pages).
Supplementary Partial European Search Report from related European Patent Application No. 17743741 dated Nov. 8, 2018 (13 pages).
International Search Report from PCT/CN2016/104354 dated Feb. 8, 2017 (5 pages).
Supplementary European Search Report from related European Patent Application No. 16861560 dated Nov. 22, 2017 (8 pages).
Supplementary European Search Report from related European Patent Application No. 16812652 dated Mar. 19, 2018 (7 pages).
International Search Report and Written Opinion dated Sep. 29, 2018 for International Application No. PCT/CN2018/094865, filed on Jul. 6, 2018 (4 pages).
"Counterclockwise: OLED screens challenge old-fashioned LCDs", GSM Arena, Dec. 2017, available at address: https://www.gsmarena.com/counterclockwise_oled_screens-news-28552.php.
Chinese Application No. 201680003673.X Office Action dated Oct. 9, 2019.
Extended European Search Report dated Aug. 27, 2019 for EP18735868.4 (12 pages).
Extended European Search Report dated Sep. 25, 2019 for EP18763421.7 (12 pages).
Office Action dated Jul. 8, 2019 for EP16812652.2 (6 pages).
Extended European Search Report dated Nov. 4, 2019 for European Patent Application No. 17850146.6 (16 pages).
Office Action for Chinese Patent Application No. 201780000132.6 dated Nov. 12, 2019 (3 pages).

* cited by examiner

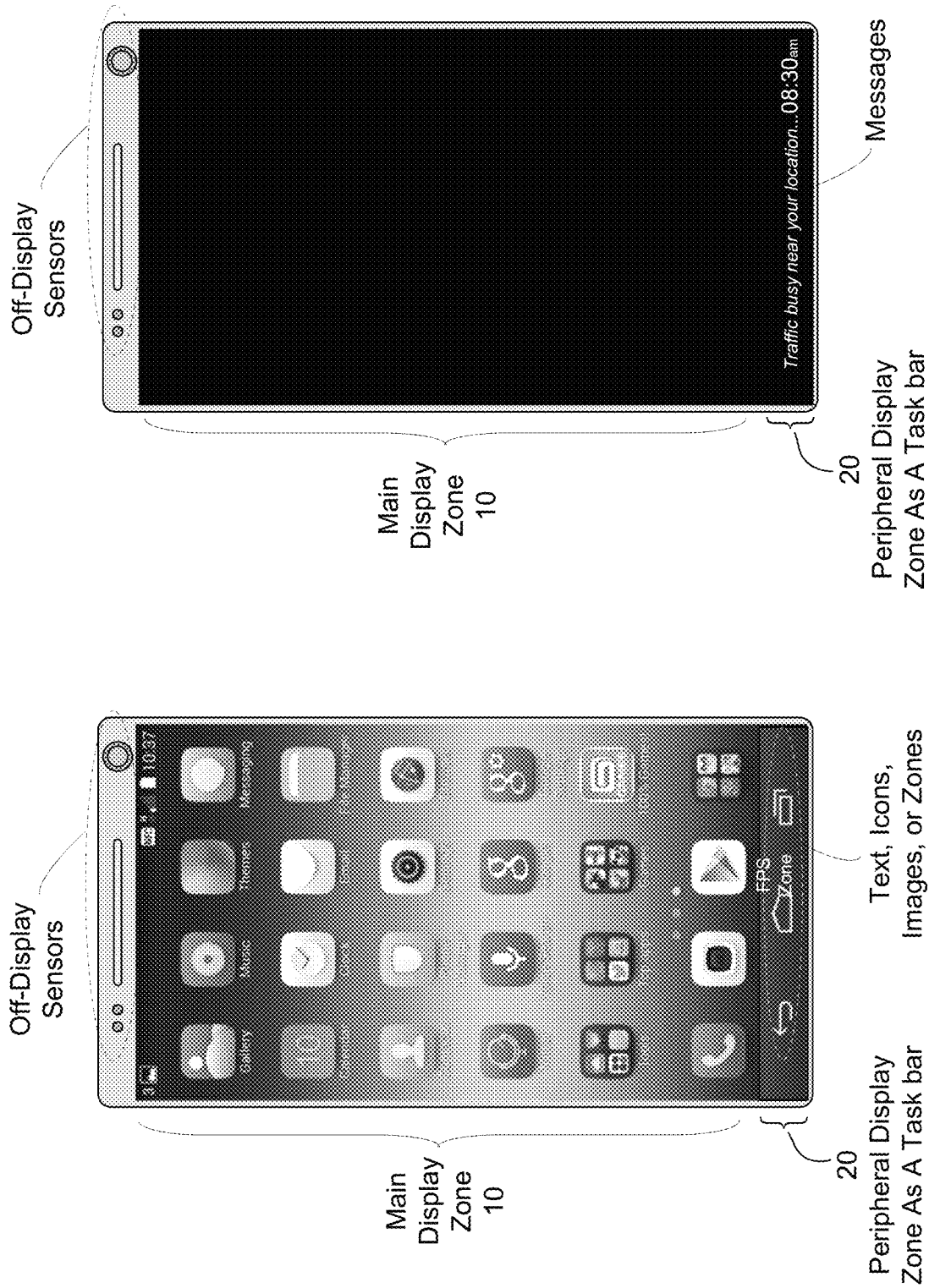

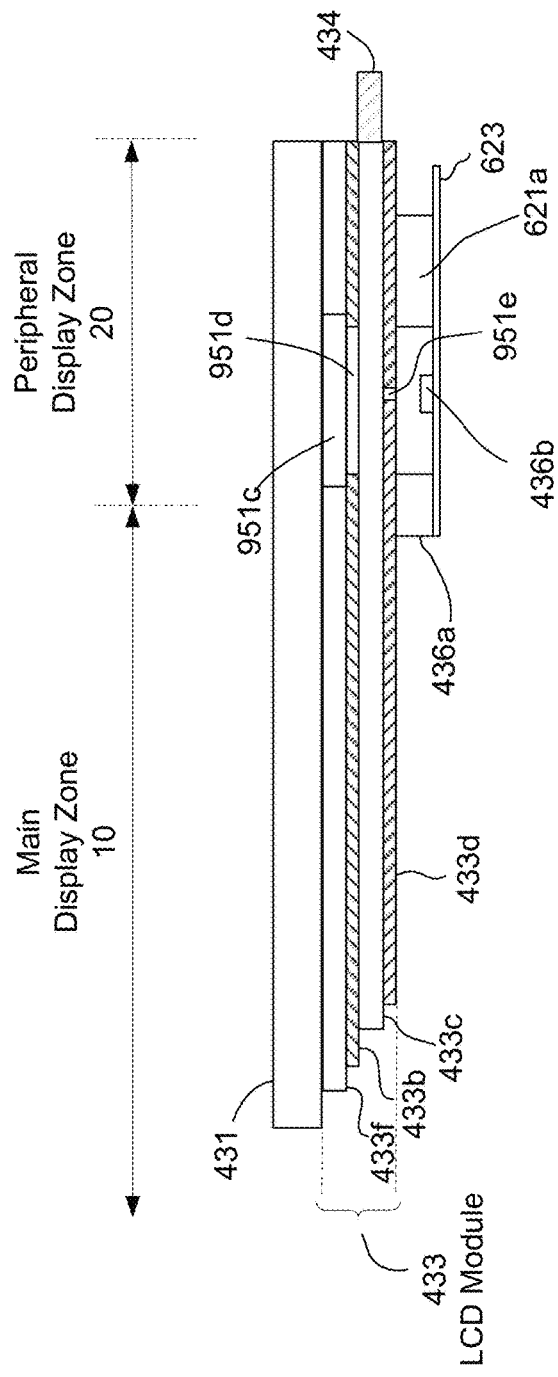

FIG. 2A

431- Cover glass
433f- Modified LCD structure layers 433a to permit light transmission for illuminating the peripheral display zone and for optical sensing
433b- LCD light diffuser layer
433c- LCD lightguide board
433d- LCD reflector film layer
436a- Probe light sources
436b- Task bar light sources under the display
436c- Task bar light sources embedded in the display
490- Backlighting light module for directing illumination light to both the main display zone and the peripheral display zone
621a- Photo detector array
623- Circuit board
951c- Modified window in other layers of the LCD layers 433f
951d- Modified window in the light diffuser 433b
951e- Micro transparent structures in the reflector film 433d

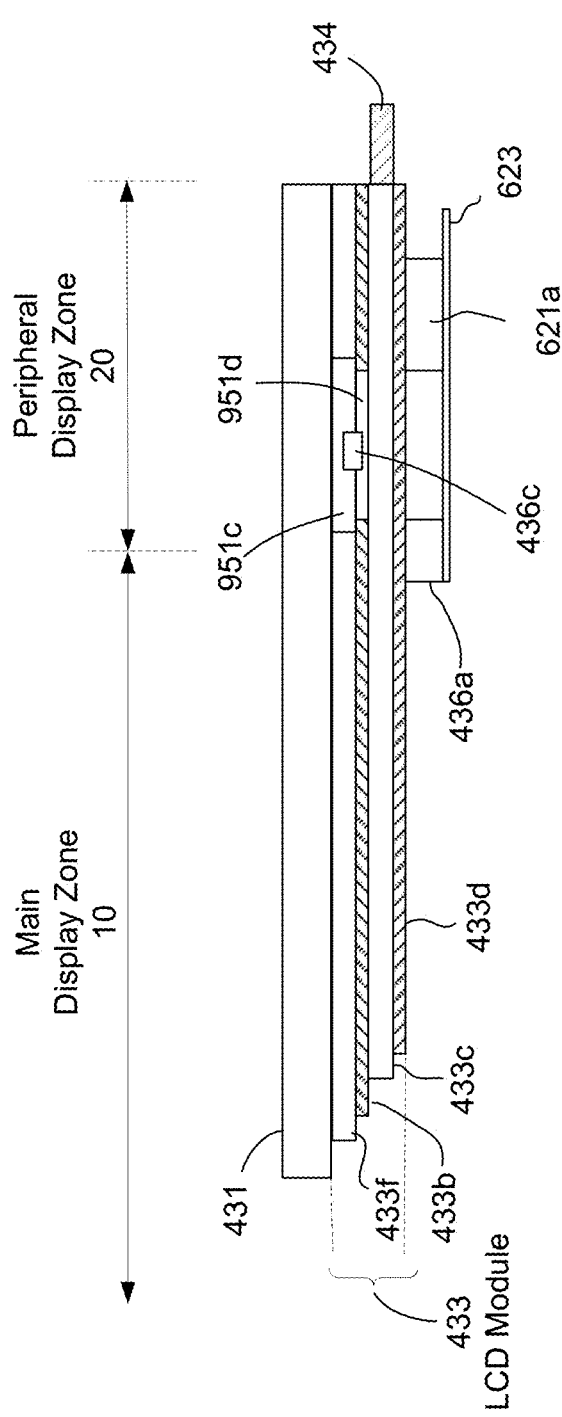

FIG. 2C

431- Cover glass
433f- Modified LCD structure layers 433a to permit light transmission for illuminating the peripheral display zone and for optical sensing
433b- LCD light diffuser layer
433c- LCD lightguide board
433d- LCD reflector film layer
436a- Probe light sources
436b- Task bar light sources under the display
436c- Task bar light sources embedded in the display
490- Backlighting light module for directing illumination light to both the main display zone and the peripheral display zone
621a- Photo detector array
623- Circuit board
951c- Modified window in other layers of the LCD layers 433f
951d- Modified window in the light diffuser 433b
951e- Micro transparent structures in the reflector film 433d

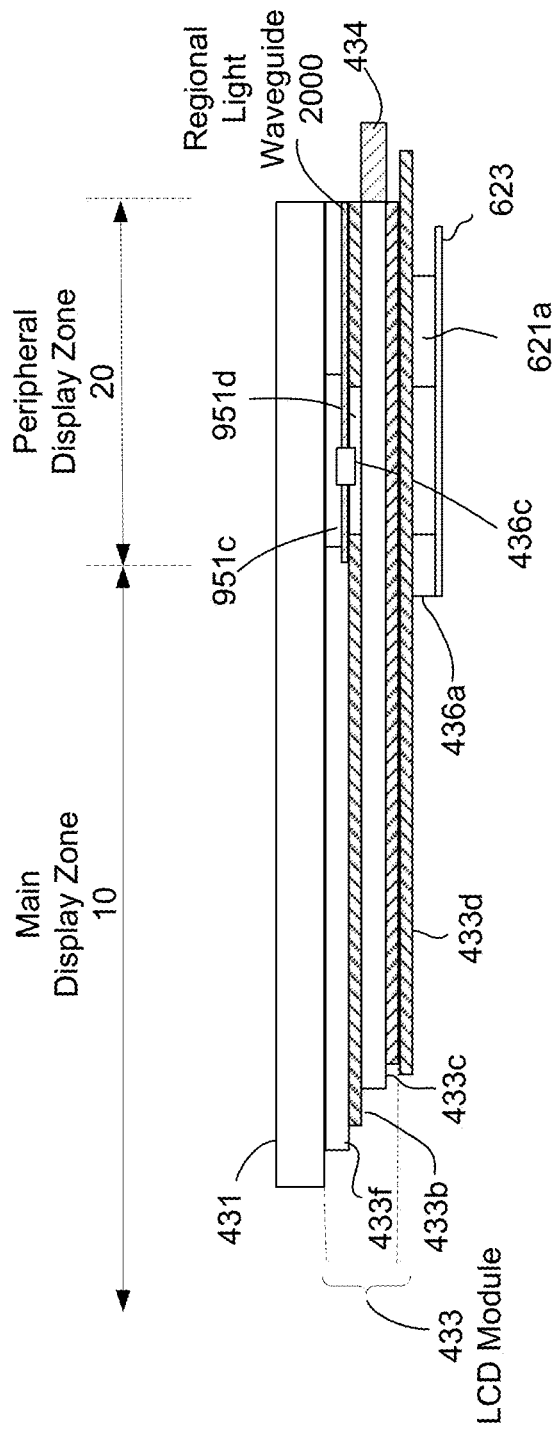

FIG. 2E

431- Cover glass
433f- modified LCD structure layers 433a to permit light transmission for illuminating the peripheral display zone and for optical sensing
433b- LCD light diffuser layer
433c- LCD lightguide board
433d- LCD reflector film
436a- Probe light sources
436b- Task bar light sources under the display
436c- Task bar light sources embedded in the display
490- Backlighting light module for directing illumination light to both the main display zone and the peripheral display zone
621a- Photo detector array
623- Circuit board
951c- Modified window in other layers of the LCD layers 433f
951d- Modified window in the light diffuser 433b
951e- Micro transparent structures in the reflector film 433d

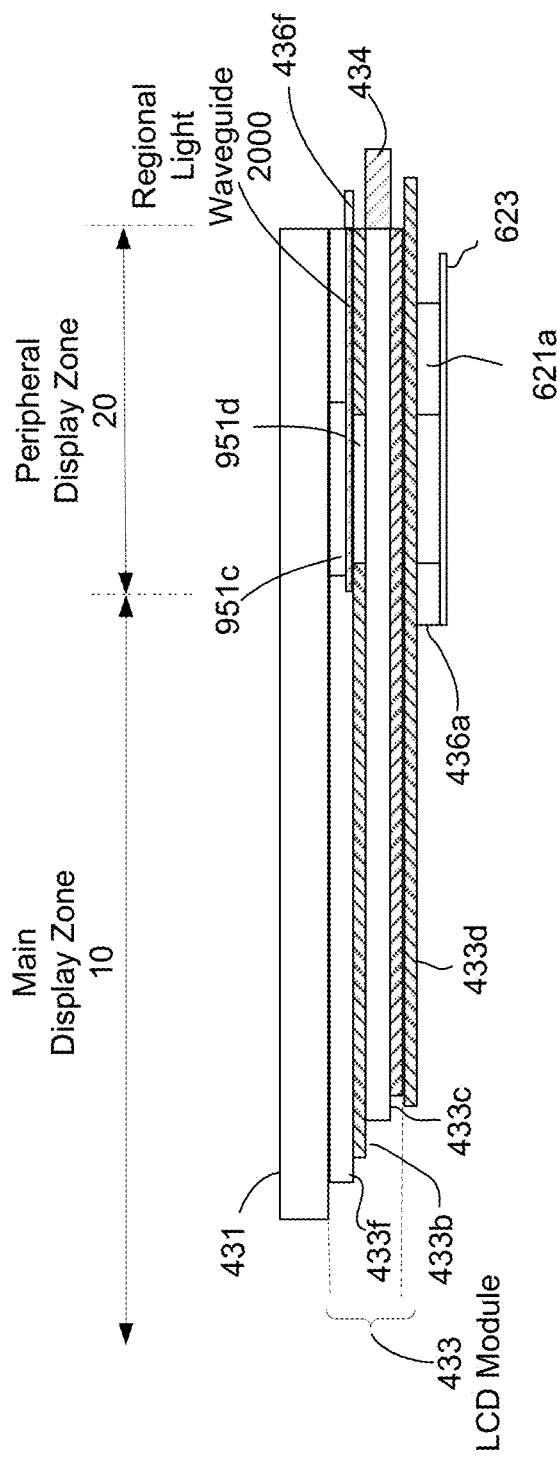

FIG. 2F

431- Cover glass
433f- Modified LCD structure layers 433a to permit light transmission for illuminating the peripheral display zone and for optical sensing
433b- LCD light diffuser layer
433c- LCD lightguide board
433d- LCD reflector film
436a- Probe light sources
436b- Task bar light sources under the display
436c- Task bar light sources embedded in the display
490- Backlighting light module for directing illumination light to both the main display zone and the peripheral display zone
621a- Photo detector array
623- Circuit board
951c- Modified window in other layers of the LCD layers 433f
951d- Modified window in the light diffuser 433b
951e- Micro transparent structures in the reflector film 433d 423- Display assembly
431- Enhanced cover glass
433- LCD display module
445, 447- Touching finger
613- Illumination light zone
615- Effective fingerprint Sensing zone
703- Optical sensor light source 524- Bottom layers
431- Cover glass
433- Display module
60- Finger tissues
61- Finger skin ridge
63- Finger skin valley
211, 212- Illumination light beams
213, 214- Cover glass total reflected light

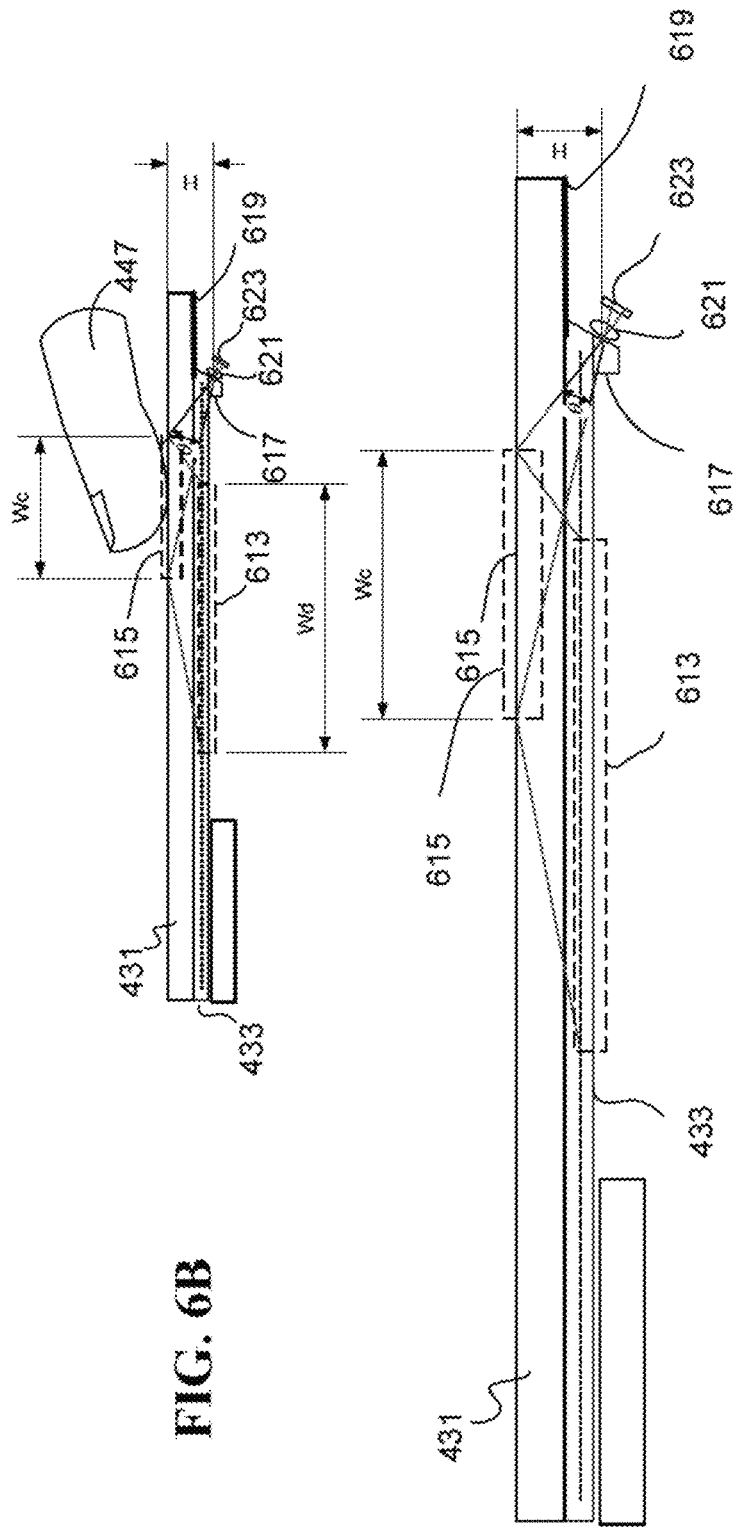

431- Enhanced cover glass
433- LCD display module
435- Circuits
613- Viewing zone
615- Effective sensing zone
618- Spacer with low RI
619- Color coating
621- Micro lens
623- Photodiode array
625- Detection axis 431- Enhanced cover glass
433- LCD display module
433b- LCD display module bottom
435- Circuits
613- Viewing zone
615- Effective sensing zone
618, 618b- Spacer with low RI
618c- Filling material
619, 619b- Color coating
621- Micro lens
623- Photodiode array
625- Detection axis 431- Enhanced cover glass
433- LCD display module
433b- LCD display module bottom
435- Circuits
613- Viewing zone
614- Extra light sources
615- Effective sensing zone
618, 618b- Spacer with low RI
618c- Filling material
619, 619b- Color coating
621- Micro lens
623- Photodiode array
625- Detection axis 431- Enhanced cover glass
433- LCD display module
433b- LCD display module bottom
435- Circuits
615- Effective sensing zone
628, 628b- Spacer with low RI
628c- Filling material
619, 619b- Color coating
621- Micro lens
623- Photodiode array
625- Detection axis

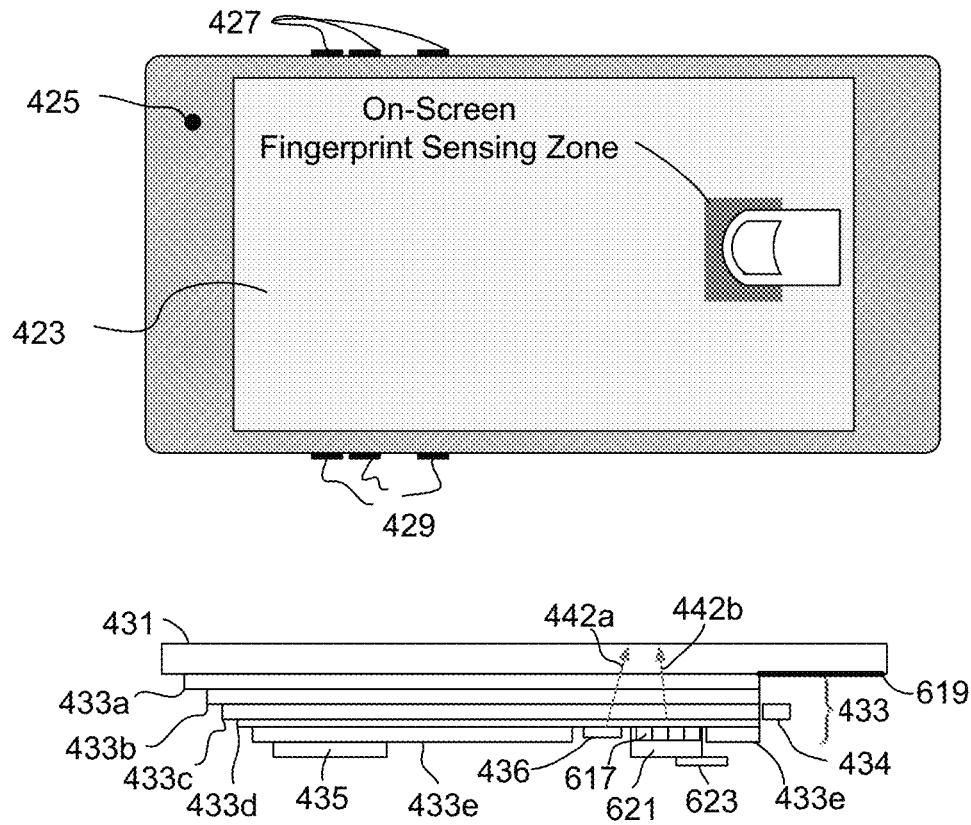

423- Display system
425- other sensor
427, 429- Side buttons
431- Cover glass
433- Liquid crystal display (LCD) module
433a- Other layers of the LCD
433b- Light diffuser
433c- Light waveguide board
433d- Reflector film
433e- LCD module frame
434- Display light sources
435- Electronics module
436- Extra light sources
442a- Light beams from extra light sources
442b- Light beams from the LCD display or display light sources
617- Collimator
619- Color layer under cover glass
621- Photo detector array
623- Circuit board

FIG. 20

423- Display system
431- Cover glass
433- LCD module
433S- LCD module scattering interfaces
617- Optical collimator array of optical collimators
621- Photo detector array
82P- Illumination light to the fingerprint sensing surface
82R- Light reflected from the fingerprint sensing surface
82D- Diffused signal light
82S- Light propagated through the optical collimator array

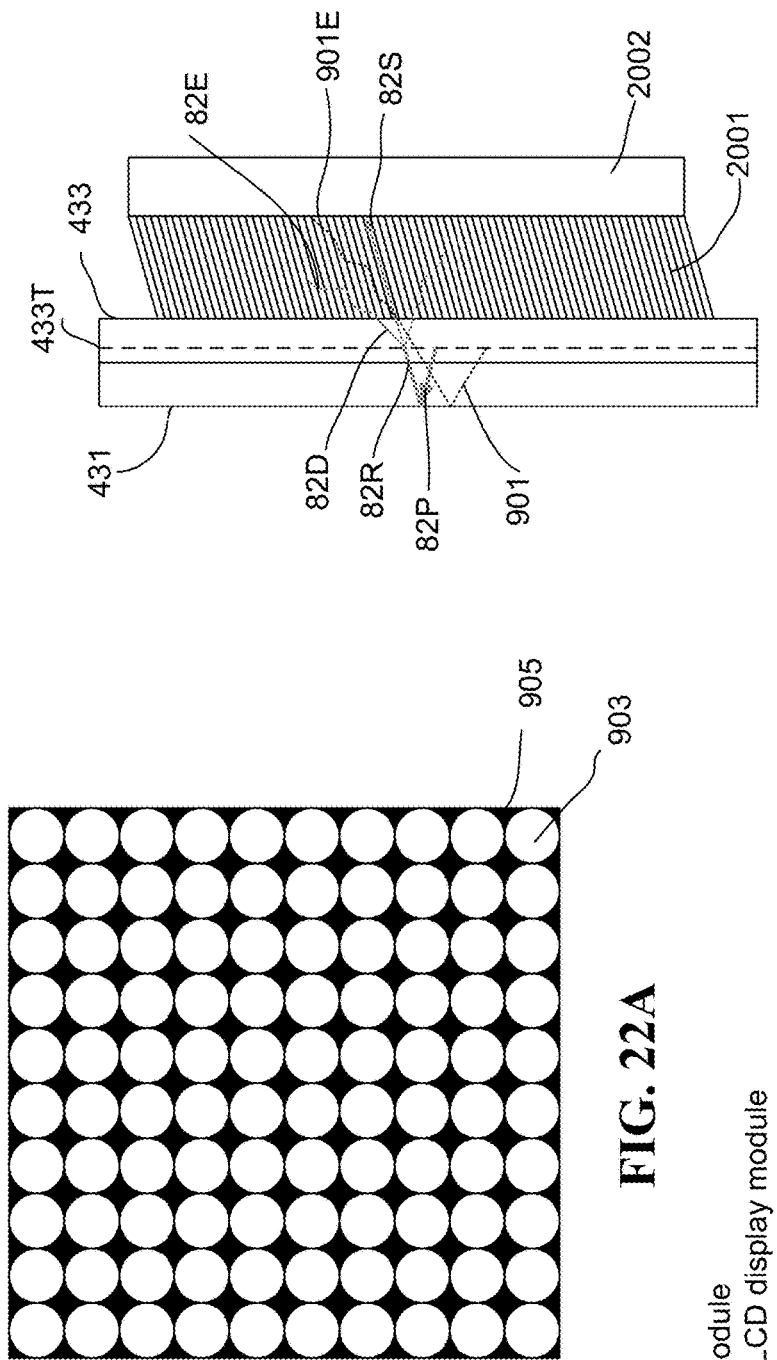

431- Cover glass
433- LCD display module
433T- TFT layer of LCD display module
2001- Optical Collimators
2002- Photo detector array
82P- Light incident to the fingerprint sensing surface
82R- Light reflected from the fingerprint sensing surface
82D- Light diffracted from TFT small holes of the LCD display module
82S- Light that goes through the optical collimator array
82E- Light absorbed by the optical collimator array
901- Other lights
901E- Light absorbed by the optical collimator array
903- Optical collimator array
905- Absorption materials 700- photo detector silicon substrate
701- photo detection detector array
702- oxide layer
703- thick oxide layer
704- metal layer in photo detector
705- holes in metal layer
706- light collimated by the metal layers with small aligned holes
710- LCD display module
711- optical hole array in LCD TFT layer
720- cover glass
730- finger on top of cover glass 431 - Cover glass
433T - TFT layer of display module
618 - One collimator Unit
681a - Filter films for the collimator unit
618b - FOV of a collimator unit
621 - Photo detector array
621a - Pinhole image by a collimator unit

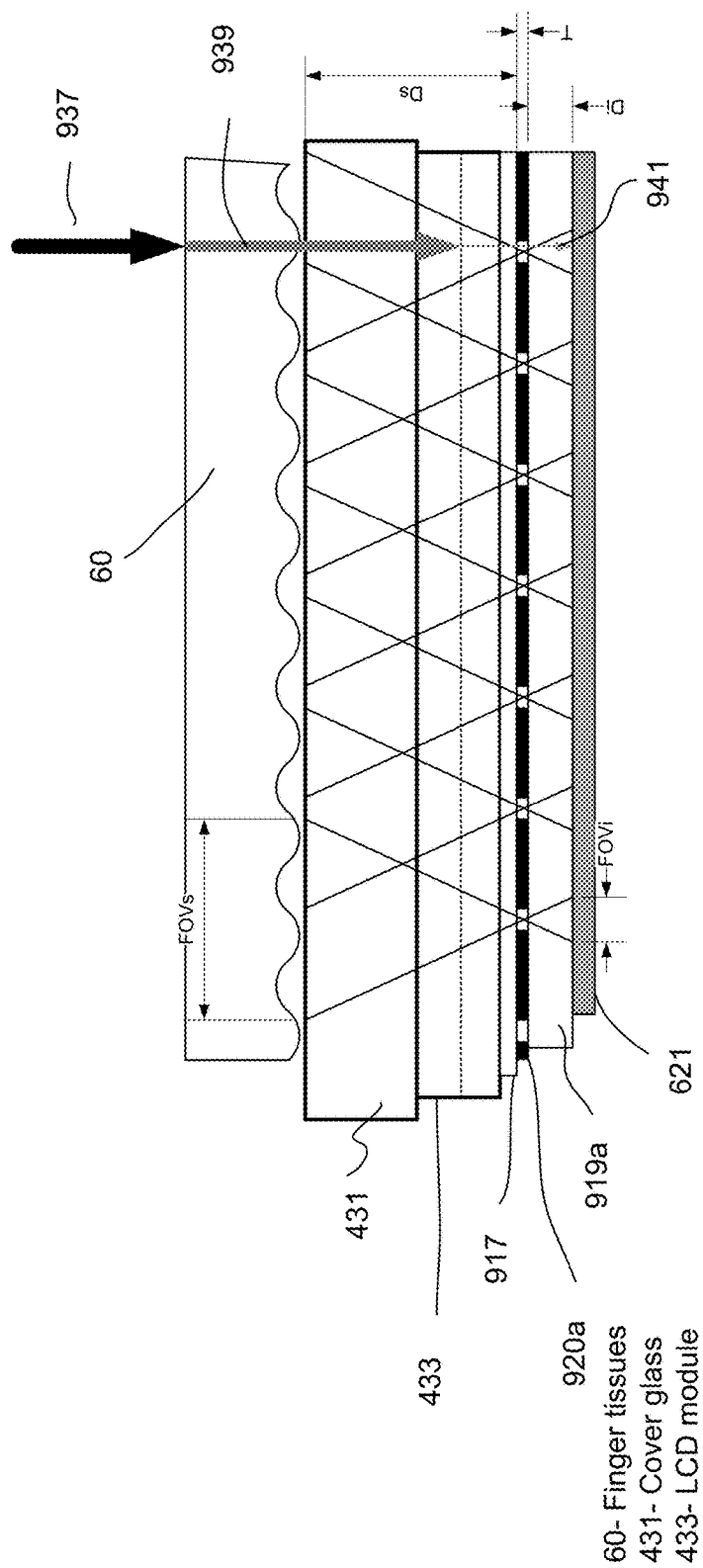

FIG. 32

60- Finger tissues
431- Cover glass
433- LCD module
621- Photo detector array
623- Circuit board
917- Spacer
919a- Protection material
920a- Pinhole array
937- Background light
939- Transmitted background light
941- Filtered background light
FOVs- Field of view on sensing surface
FOVi- Field of view on imaging plane
Ds- Distance of the sensing surface
Di- Distance of the image plane
T- Thickness of the pinhole layers

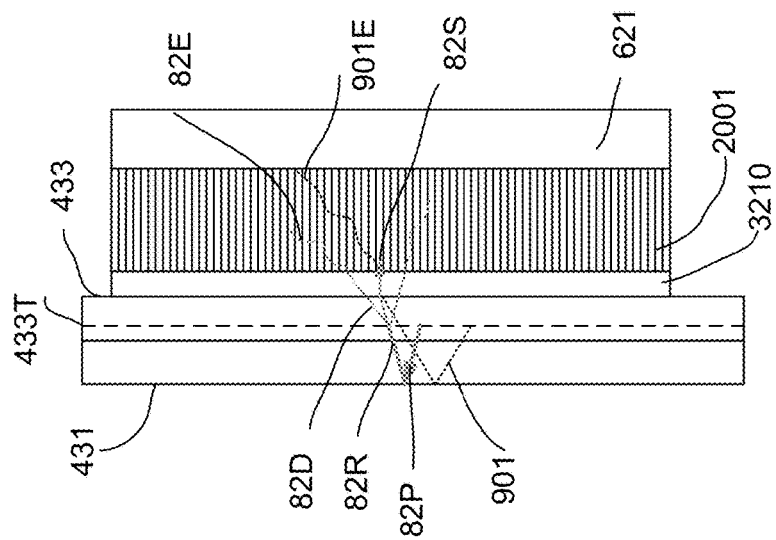

FIG. 33A

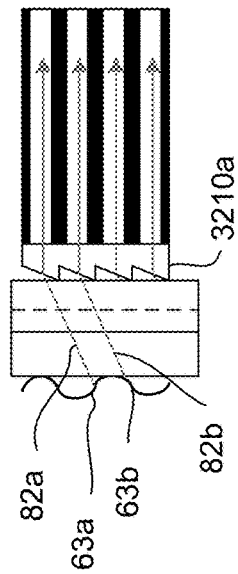

FIG. 33B

431- Cover glass
433- LCD display module
433T- TFT layer of LCD display module
3210- Viewing angle adaptor optical layer
3210a- Detail of the viewing angle adaptor layer
2001- Light Collimator
621- Photo detector array
63a, 63b- Different positions in fingerprint valley
82a, 82b- Light from different fingerprint valley positions
82P- Light shine to finger
82R- Light reflected from finger surface
82D- Light diffracted from TFT small holes
82S- Light goes through collimator
82E- Light absorbed by collimator
901- Other lights
901E- Light absorbed by collimator 431- Cover glass
433a- Other layers of the LCD
433b- Light diffuser
433c- Light waveguide board
433d- Reflector film
436- Extra light sources
617- Collimator
951a- Holes in the LCD diffuser sheet
951b- Weak diffusion positions
969- Tilted holes for the detection and the extra light source illumination

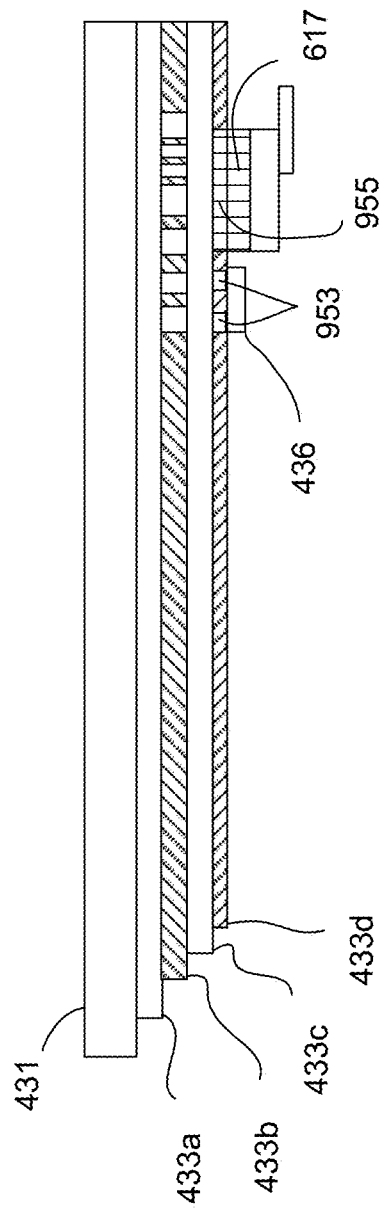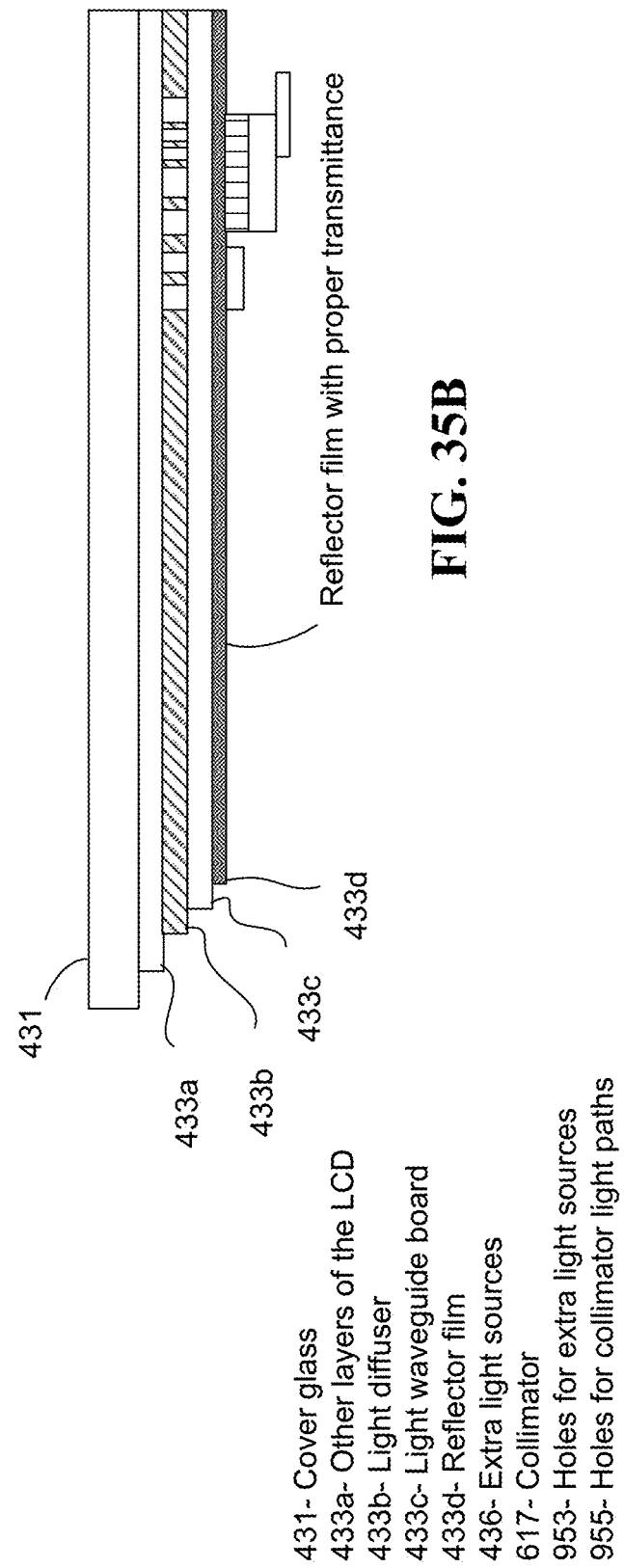
FIG. 35A
FIG. 35B
- 431- Cover glass
- 433a- Other layers of the LCD
- 433b- Light diffuser
- 433c- Light waveguide board
- 433d- Reflector film
- 436- Extra light sources
- 617- Collimator
- 953- Holes for extra light sources
- 955- Holes for collimator light paths 431- Cover glass
433a- Other layers of the LCD
433b- Light diffuser
433c- Light waveguide board
433d- Reflector film
434- Display light sources
436- Extra light sources
617- Collimator
957- Diffused light from display light sources
959- Diffused light from extra light sources

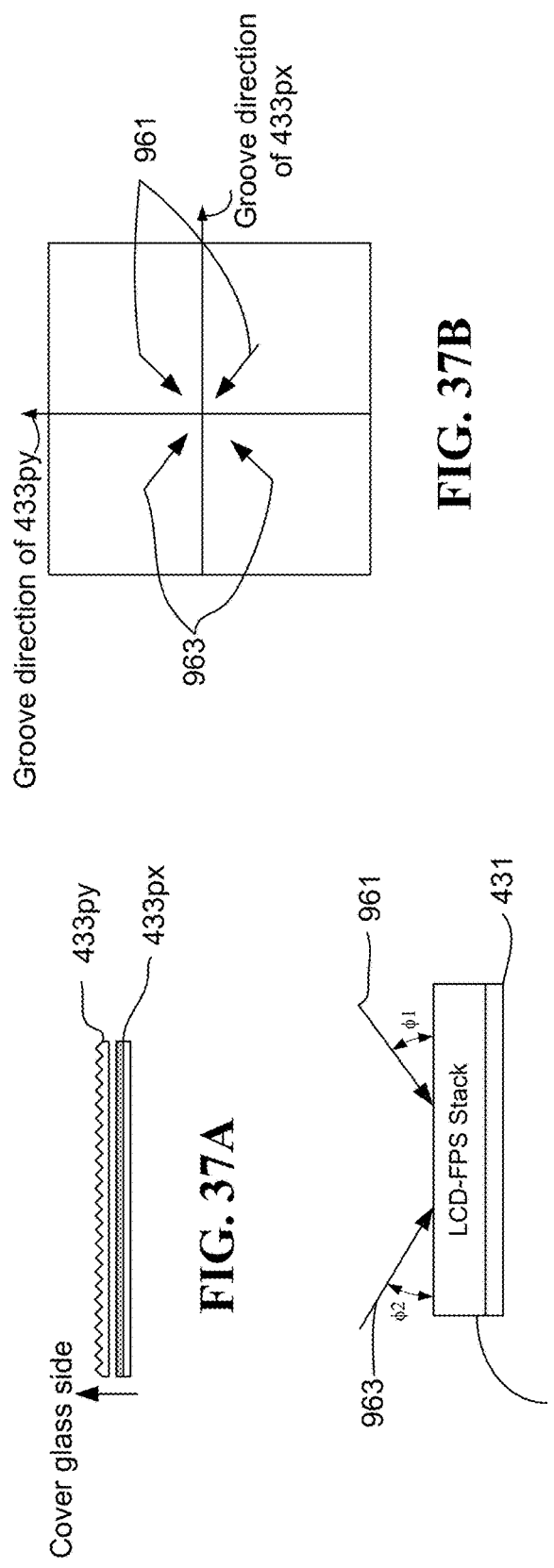

LCD-FPS Stack includes the enhancement films

431- Cover glass
433px, 433py- Back light enhancement films
436- Extra light source
617U- A collimator unit
621U- A photodetector array unit
961,963- Detection module viewing direction or extra light illumination direction
965- Sub detection light path of a detection unit
967- Partial of the illumination light path
$\phi 1, \phi 2$ - Detection module viewing direction or extra light illumination direction 431 - Cover glass
433a - Other layers of the LCD
433b - Light diffuser
433c - Light waveguide board
433d - Reflector film
434 - Display light sources
436 - Extra light sources
617 - Collimator
959 - Diffused light from extra light sources
973 - Micro holes for extra light source
975 - Narrow transparent window 3301- Lightly pressed fingerprint
3303- Heavily pressed fingerprint
3305- Integration zone

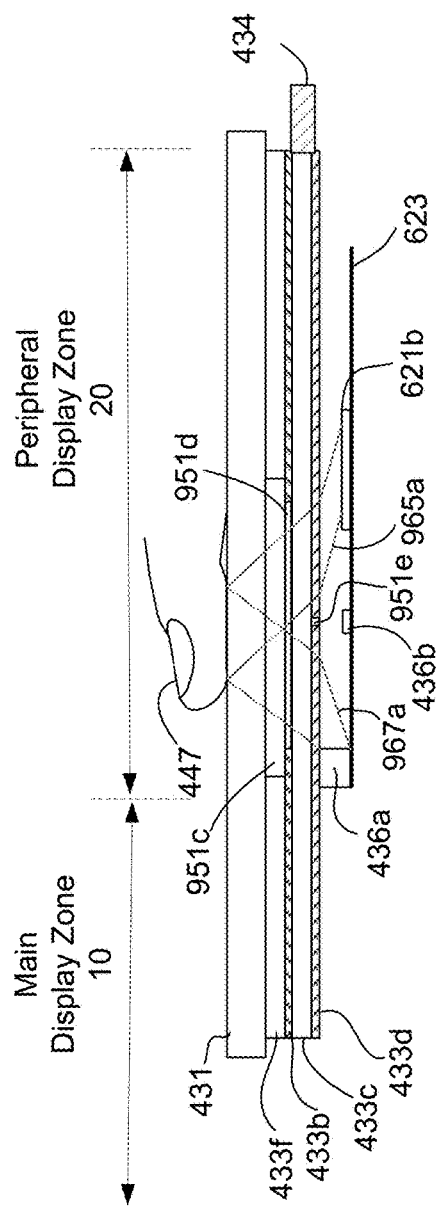
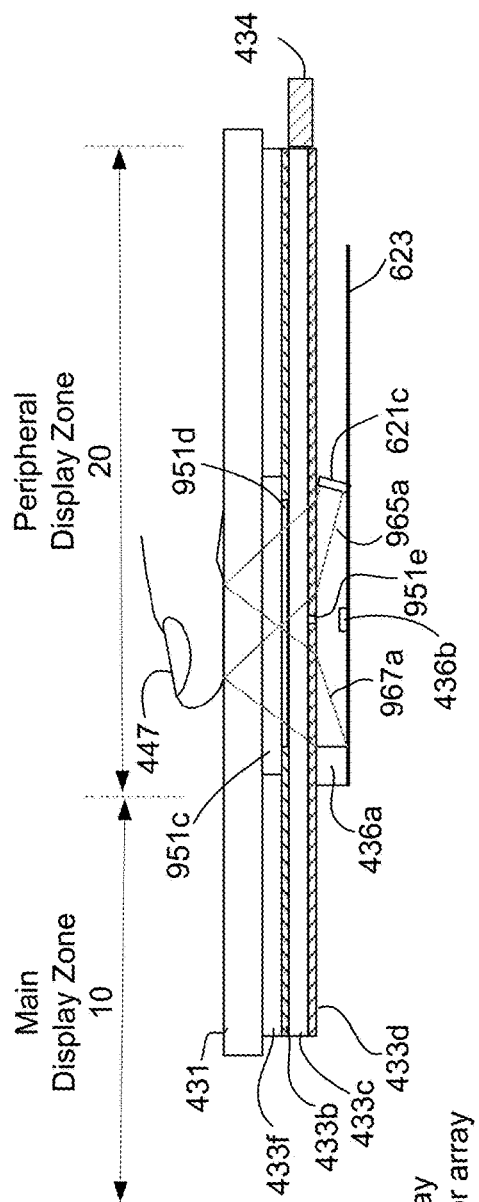
FIG. 41A
FIG. 41B
431 - Cover glass
447 - Finger
436a - Probe light sources
621b - Uniform photo detector array
621c - Compressed photo detector array
623 - Circuit board
965a - Signal light beam
967a - Probe light beam 431 - Cover glass
447 - Finger
436a - Probe light sources
617p - Mirror
617q - Image lens
621d - Photo detector array
623 - Circuit board
965b - Signal light beam
967b - Probe light beam

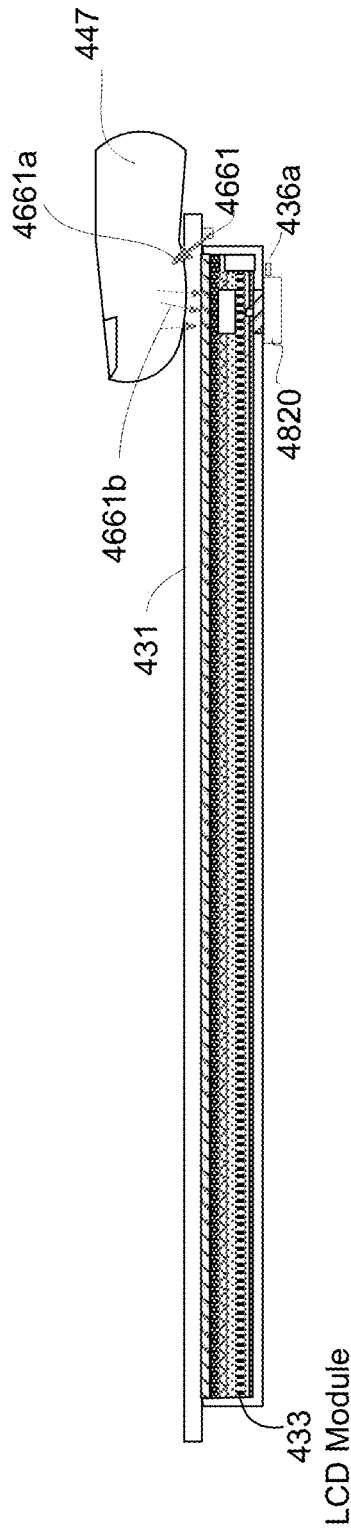

FIG. 48

447- Touching finger
4820- Under-LCD optical sensor module
4661- Under cover glass probe light sources shifted away from the fingerprint sensing area for producing transmitted probe light to carry the fingerprint pattern inside the finger
4661a- Incident light beams
4661b- Signal light scattered by finger tissues
436a- Probe light sources located near or under the fingerprint sensing area under the LCD module to produce both reflected probe light at the outer side of the finger and backscattered probe light inside the finger

DEVICES WITH PERIPHERAL TASK BAR DISPLAY ZONE AND UNDER-LCD SCREEN OPTICAL SENSOR MODULE FOR ON-SCREEN FINGERPRINT SENSING

CROSS REFERENCE TO RELATED APPLICATIONS

This patent document claims the benefits and priority of U.S. Provisional Patent Application No. 62/468,337, filed on Mar. 7, 2017, and entitled "UNDER-LCD SCREEN OPTICAL SENSOR MODULE FOR ON-SCREEN FINGERPRINT SENSING WITH PERIPHERAL TASK BAR DISPLAY ZONE IN DEVICE DISPLAY".

This patent document also claims the benefits and priority of, and is a continuation-in-part application of, U.S. patent application Ser. No. 15/708,088, filed on Sep. 18, 2017, and entitled "UNDER-LCD SCREEN OPTICAL SENSOR MODULE FOR ON-SCREEN FINGERPRINT SENSING.

TECHNICAL FIELD

This patent document relates to electronic devices or systems with displays, and optical sensor modules under device displays for performing one or more sensing operations such as fingerprints or other parameter measurements based on optical sensing in an electronic device such as a mobile device or a wearable device or a larger system.

BACKGROUND

Displays of electronic devices or systems are an important part of the user interface for performing user functions and device operations and allow display of information in various forms to users and performing operations by users. Such displays may be structured as touch-sensitive display screens to provide touch sensing operations as additional interactions between users and electronic devices and communications or interactions with others via communication links or networks.

In addition, various sensors can be implemented in electronic devices or systems to provide certain desired functions. In some designs of mobile phones, tablets and other portable devices, certain sensors can be placed outside the display screens but are on the same facet of the device where the display screen is located. Examples of some sensors in some smart phones or tablets includes a front camera, a proximity sensor, an ambient light sensor, or others (e.g., projectors and imaging sensors for facial recognition).

A sensor for user authentication is another example of sensors for devices including portable or mobile computing devices (e.g., laptops, tablets, smartphones), gaming systems, various databases, information systems or larger computer-controlled systems can employ user authentication mechanisms to protect personal data and prevent unauthorized access. User authentication on an electronic device can be carried out through one or multiple forms of biometric identifiers, which can be used alone or in addition to conventional password authentication methods. A popular form of biometric identifiers is a person's fingerprint pattern. A fingerprint sensor can be built into the electronic device to read a user's fingerprint pattern so that the device can only be unlocked by an authorized user of the device through authentication of the authorized user's fingerprint pattern. Another example of sensors for electronic devices or systems is a biomedical sensor, e.g., a heartbeat sensor in wearable devices like wrist band devices or watches. In general, different sensors can be provided in electronic devices to achieve different sensing operations and functions.

Fingerprints can be used to authenticate users for accessing electronic devices, computer-controlled systems, electronic databases or information systems, either used as a stand-alone authentication method or in combination with one or more other authentication methods such as a password authentication method. For example, electronic devices including portable or mobile computing devices, such as laptops, tablets, smartphones, and gaming systems can employ user authentication mechanisms to protect personal data and prevent unauthorized access. In another example, a computer or a computer-controlled device or system for an organization or enterprise should be secured to allow only authorized personnel to access in order to protect the information or the use of the device or system for the organization or enterprise. The information stored in portable devices and computer-controlled databases, devices or systems, may be personal in nature, such as personal contacts or phonebook, personal photos, personal health information or other personal information, or confidential information for proprietary use by an organization or enterprise, such as business financial information, employee data, trade secrets and other proprietary information. If the security of the access to the electronic device or system is compromised, these data may be accessed by others, causing loss of privacy of individuals or loss of valuable confidential information. Beyond security of information, securing access to computers and computer-controlled devices or systems also allow safeguard the use of devices or systems that are controlled by computers or computer processors such as computer-controlled automobiles and other systems such as ATMs.

SUMMARY

This patent document discloses display designs for electronic devices or systems to include both a main display zone and a peripheral display zone that collectively form a seamless contiguous display area for displaying images, content or information over the two zones as a single display area and further allowing for operating the peripheral display zone independently from the main display zone to display certain images, information, or content only on the peripheral display zone even when the main display zone is turned off. In some implementations as illustrated by examples below, when the main display zone and peripheral display zone are implemented based on the LCD display technology, the two zones may share the same backlighting light module so both zones can be active when the backlighting light module is on and, in addition, an independent illumination backlighting light source can be provided as an additional illumination source for the peripheral display zone to allow it to operate when the main display zone and the shared backlighting light module for the both zones are turned off. In addition to providing display functions separate from or in combination with the display functions by the main display zone, the peripheral display zone based on the disclosed technology can be used to provide for certain sensing functions by including one or more sensors under the display area for the peripheral display zone.

In one aspect, the disclosed technology in this patent document can be implemented to construct an electronic device capable of detecting a fingerprint by optical sensing to include a liquid crystal display (LCD) screen that provides touch sensing operations and includes a LCD display panel structure to display images, wherein the LCD display screen includes (1) a main display zone having LCD display pixels and a peripheral display zone having LCD display pixels wherein the main display zone and peripheral display zone collectively form a seamless contiguous LCD display area, and (2) a LCD backlighting module that provides backlighting light to illuminate both the main display zone and peripheral display zone. A designated peripheral display zone illumination module is located relative to the LCD screen and structured to produce and direct illumination light only to the peripheral display zone to enable the peripheral display zone to display images or information independently from the main display zone and to be operable to display images or information when the LCD backlighting module is turned off. A top transparent layer is formed over the LCD screen as an interface for being touched by a user for the touch sensing operations and for transmitting the light from LCD screen to display images or information to a user and an optical sensor module is located below the LCD display panel structure and structured to receive probe light that is from an object in contact with or near the peripheral display zone and passes through the LCD screen to detect a fingerprint.

In another aspect, the disclosed technology in this patent document can be implemented to construct an electronic device capable of detecting a fingerprint by optical sensing to include a liquid crystal display (LCD) display panel structure to display images or information and to provide touch sensing operations, the LCD display panel structure including LCD layers to display images or information by processing illumination backlighting light in a main display zone and a peripheral display zone which collectively form a seamless contiguous LCD display area, a light diffusion layer that diffuses the illumination backlighting light in the main display zone and peripheral display zone, a waveguide layer that receives the illumination backlighting light and directs the received illumination backlighting light to the main display zone and peripheral display zone, and a light reflector layer for redirecting illumination backlighting light in the LCD layers of the main display zone and peripheral display zone for displaying operations, each of the light diffuser and the light reflector layer structured to include holes or passages at a selected area in the peripheral display zone of the LCD display panel structure to allow light to be transmitted. This device include a LCD backlighting light module coupled to the waveguide layer of the LCD display panel structure to produce backlighting light to the LCD layers for displaying images or information; a designated peripheral display zone illumination module located to produce and direct illumination light only to the peripheral display zone to enable the peripheral display zone to display images or information independently from the main display zone and to be operable to display images or information when the LCD backlighting module is turned off; a top transparent layer formed over the LCD display panel structure as an interface for being touched by a user for the touch sensing operations; an optical sensor module located below the LCD display panel structure to receive probe light from the top transparent layer and passes through the LCD display panel structure to detect a fingerprint; and one or more probe light sources, separate from the LCD backlighting light module, located under the top transparent layer, to produce the probe light that illuminates a designated fingerprint sensing area on the top transparent layer in the peripheral display zone for a user to place a finger for optical fingerprint sensing by the optical sensor module.

In yet another aspect, the disclosed technology in this patent document can be implemented to construct an electronic device capable of detecting a fingerprint by optical sensing to include a liquid crystal display (LCD) screen that provides touch sensing operations and includes a LCD display panel structure to display images. The LCD display screen includes a main display zone having LCD display pixels and a peripheral display zone having LCD display pixels wherein the main display zone and peripheral display zone collectively form a seamless contiguous LCD display area. The LCD display screen can also include a LCD backlighting module that provides backlighting light to illuminate both the main display zone and peripheral display zone, and a designated peripheral display zone illumination module that provides illumination light only to the peripheral display zone to enable the peripheral display zone to display images independently from the main display zone. This device includes a top transparent layer formed over the device screen as an interface for being touched by a user for the touch sensing operations and for transmitting the light from the display structure to display images to a user; and an optical sensor module located below the display panel structure and configured such that at least part of the optical sensor module is located below the peripheral display zone. The optical sensor module is structured to receive probe light that is from an object in contact with or near the peripheral display zone and passes through the LCD screen to detect a fingerprint.

In implementing the above LCD display screen with (1) the main display zone and (2) the peripheral display, a control module may be coupled to the main display zone, peripheral display zone, the LCD backlighting module and the designated peripheral display zone illumination module to enable the designated peripheral display zone illumination module to illuminate the peripheral display zone to display images when the LCD backlighting module is turned off. In some implementations, the control module may be structured to control the peripheral display zone to display a fingerprint sensing zone in the peripheral display zone for a user to place a finger there for fingerprint sensing, to control the peripheral display zone to display a message, to display an icon that allows a user to launch an app or perform a function by touching the icon or to display other information.

In implementing the above device, the optical sensor module may include different optical designs for directing the probe light to an optical detector array for sensing. In some designs, the probe light may be projected onto the optical detector array without a lens. In some designs, one or more imaging lenses may be used to direct the probe light onto the optical detector array. In some other designs, the optical sensor module may include an optical collimator array of optical collimators that receives the probe light and an optical detector array of optical detectors to receive the probe light from the optical collimator array.

The drawings, the description and the claims below provide a more detailed description of the above and other aspects and features of the disclosed technology and their implementations.

BRIEF DESCRIPTION OF THE DRAWINGS

FIGS. 1A, 1B, 1C and 1D illustrate examples of different uses of a peripheral display zone of a display with both a main display zone and the peripheral display zone to allow the peripheral display zone to operate independently from the main display zone to display certain images, information, or content while enabling the use of the main display zone and the peripheral display as a single seamless contiguous display area.

FIGS. 2A and 2B show an example of a device having a LCD display module to provide the main and peripheral display zones in the same LCD panel with a designated peripheral display zone illumination module having one or more designated illumination light sources under the LCD panel.

FIGS. 2C and 2D show another example of a device having a LCD display module to provide the main and peripheral display zones in the same LCD panel with a designated peripheral display zone illumination module having one or more designated illumination light sources within the LCD panel.

FIGS. 2D, 2E and 2F show examples of devices having a LCD display module to provide the main and peripheral display zones in the same LCD panel with a designated peripheral display zone illumination module and a designated regional illumination waveguide for distributing the illumination light to the peripheral display zone only.

FIGS. 6A-6C, 7, 8A-8B, 9, and 10A-10B show example designs of under-screen optical sensor modules.

FIGS. 20, 21A, 21B, 22A, and 22B illustrate examples of various designs for fingerprint sensing using a under-screen optical sensor module using an array of optical collimators or pinholes for directing signal light carrying fingerprint information to the optical detector array.

FIG. 32 shows an example of an under-LCD optical sensor module using an optical pinhole array for optical sensing.

FIGS. 33A and 33B show an example of an optical fingerprint sensor under a LCD display panel having an optical deflection or diffraction device or layer.

FIGS. 35A and 35B show examples of LCD reflector designs for improved under-LCD optical sensing.

FIGS. 37A-37D show examples of enhancement features for improved under-LCD optical sensing.

FIGS. 41A, 41B and 42 show examples of specific implementations of an optical sensor module placed under an LCD display for a device having a LCD display module to provide the main and peripheral display zones in the same LCD panel.

FIG. 48 shows an example of a device having an optical sensor module placed under an LCD display by using two different probe light sources at two different locations to produce probe light that can transmit through finger tissues for optical sensing.

DETAILED DESCRIPTION

Figure 1D:
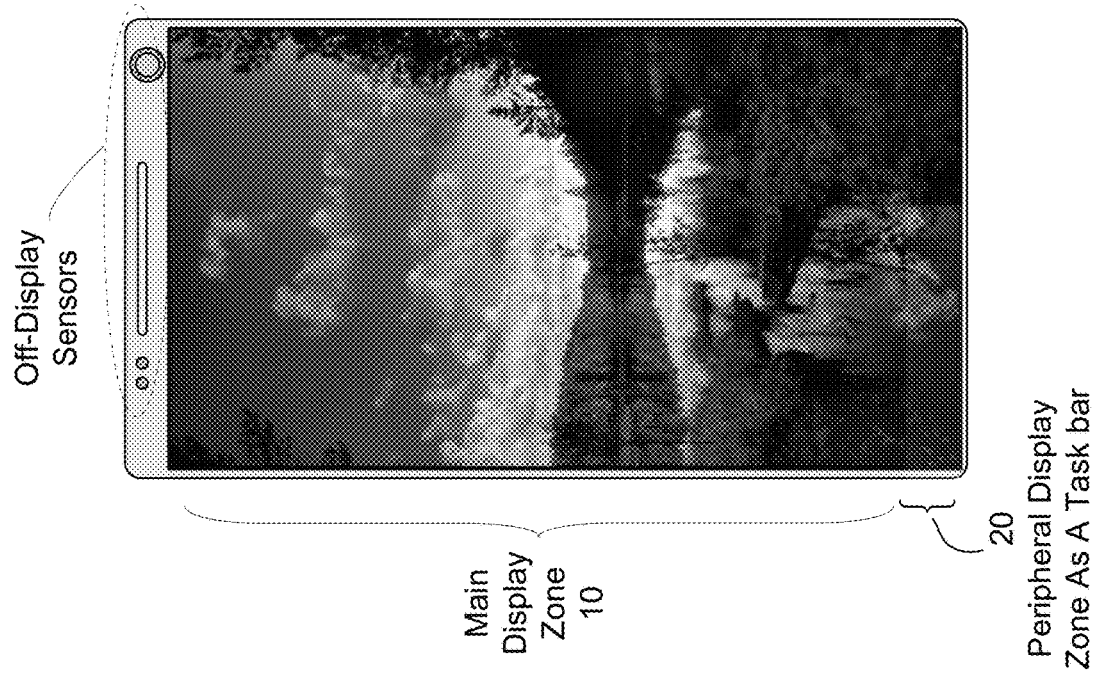
Figure 1C:
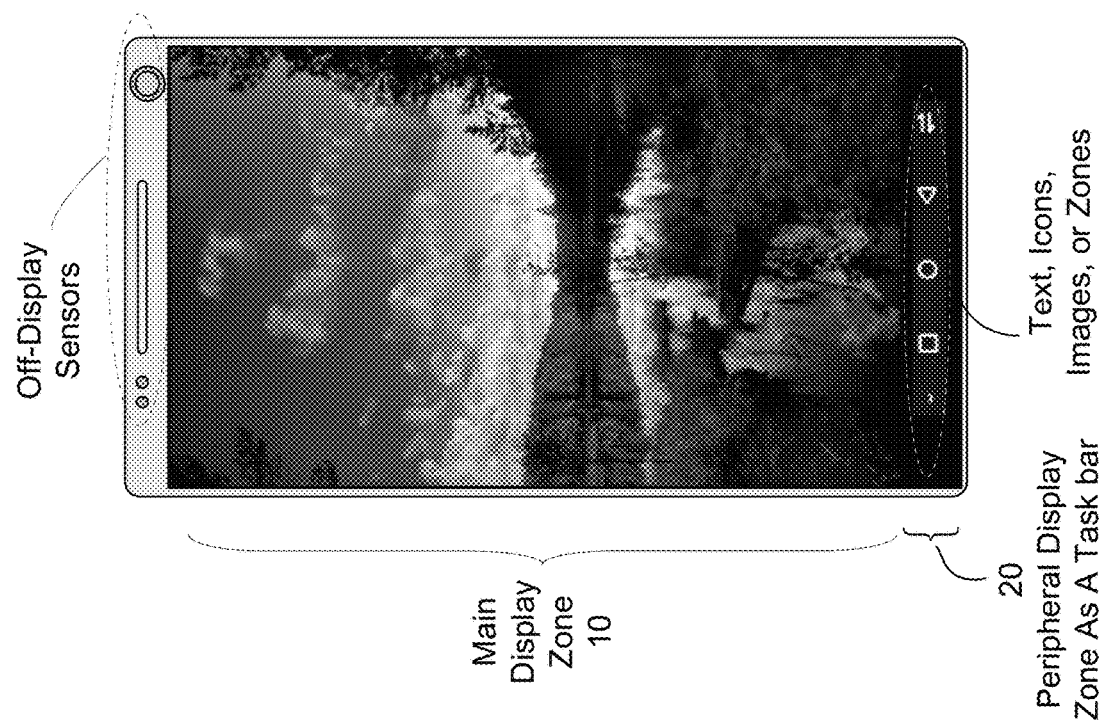

This patent document discloses display designs for electronic devices or systems to include both a main display zone and a peripheral display zone for displaying images, information, icons and for performing user operations. The two display zones are designed to be located next to each other so that they can collectively form a seamless contiguous display area for displaying images, content or information to function as a single display area and to further allow for operating the peripheral display zone independently from the main display zone to display certain images, information, or content. This combination of having both a main display zone and a peripheral display zone as either a collective single display area or two separate display areas provides versatile applications for displaying operations and for user interface operations.

In addition to providing display functions separate from or in combination with the display functions by the main display zone, the peripheral display zone based on the disclosed technology can be used to provide for certain sensing functions by including one or more sensors under the display area for the peripheral display zone. For example, the peripheral display zone may include an optical sensing area for capturing light to be detected by an optical sensor module that is placed under or near the peripheral display zone of the device display for optical sensing to provide optical sensing functions such as optical fingerprint sensing, optical sensing of other parameters or optical sensing for determining whether an object in contact is from a live person.

For example, in devices with under-screen optical sensing functions disclosed in this document, the peripheral display zone may include an optical sensing area for capturing returned light carrying fingerprint patterns and other information to be detected by an optical sensor module that is placed under or near the peripheral display zone of the device display for optical sensing to provide one or more optical sensing functions including, e.g., optical fingerprint sensing and optical sensing for determining whether an object in contact is from a live person. The techniques disclosed here based on a 2-zone design of adjacent main display zone and peripheral display zone may be implemented based on liquid crystal display (LCD) panels based on illumination light from a backlighting light source outside each LCD display pixel or other display panels such as organic light-emitting diode (OLED) panels based on light emitted within each OLED pixel.

FIGS. 1A, 1B, 1C and 1D illustrate examples of different display modes of a smartphone having adjacent main display zone 10 and peripheral display zone 20 for different uses of the peripheral display zone 20. The display having both the main display zone 10 and the peripheral display zone 20 are designed to allow the peripheral display zone 20 to operate independently from the main display zone 10 to display certain images, information, or content while enabling the use of the main display zone and the peripheral display together to function as a single seamless contiguous display area. To illustrate various features of the disclosed 2-zone display technology, the main display zone 10 and the peripheral display zone 20 can be implemented by a LCD panel in this and other examples.

The display in FIGS. 1A, 1B, 1C and 1D can be a LCD screen integrated with touch sensing layers to provide touch sensing operations and to display images, information and other objects. This LCD screen can be designed to include (1) a main display zone 10 having LCD display pixels as shown in the upper larger area and (2) a peripheral display zone 20 having LCD display pixels as shown in the lower smaller bar area. The two display zones 10 and 20 are adjacent to each other and are integrated so that the main display zone 10 and peripheral display zone 20 can collectively form and function a single, seamless and contiguous LCD display area. The peripheral display zone 20 in many implementations is a display area smaller than the main display zone 10, e.g., as a bottom task bar zone as shown in the specific example in FIGS. 1A-1D. In the example illustrated, certain device sensors are placed off the two display zones 10 and 20 but certain sensors may be placed within the two display zones 10 and 20 such as an optical sensor module without requiring real estate space outside the display screen.

In some implementations of such a LCD display, two illumination light modules may be provided: (1) a LCD backlighting module to provide visible backlighting light to illuminate LCD pixels in both the main display zone 10 and peripheral display zone 20, and (2) an additional designated peripheral display zone illumination module to produce visible illumination light only to LCD pixels in the peripheral display zone 20 for displaying images, information and other objects independently from the main display zone, including when the main display zone is turned off. Such as a 2-zone display device can include a top transparent layer formed over the device screen as an interface for being touched by a user for the touch sensing operations and for transmitting the light from the display structure to display images to a user and, in various implementations, the top transparent layer can be over both zones on the top as a single seamless layer.

In addition, a control module can be coupled to the main display zone 10, peripheral display zone 20, the LCD backlighting module and the designated peripheral display zone illumination module to control the operations of the two display zones 10 and 20. For example, this control module can control the LCD backlighting module to provide backlighting illumination light to both zones 10 and 20 and to control the LCD pixels in both zones to perform various modes of displaying functions shown in FIGS. 1A-1D where the peripheral display zone 20 can either join the main display zone 10 as a combined single display or, independent from the main display zone 10, display its own information. For another example, the control module can enable the designated peripheral display zone illumination module to illuminate the peripheral display zone 20 to display images when the LCD backlighting module is turned off as shown in the example in FIG. 1B.

In many applications, as further explained in detail below, an optical sensor module may be provided at a location below the display panel structure of the display screen and configured such that at least part of the optical sensor module is located below the peripheral display zone 20. This optical sensor module can be structured to receive probe light that is from an object in contact with or near the peripheral display zone and passes through the LCD screen to detect a fingerprint, other biometric information associated with the finger or other sensing functions based on optical sensing. The top surface of the display screen can include a fingerprint sensing (FPS) zone or area where the probe light coming from underneath the top surface is present to illuminate a finger for fingerprint sensing or for one or more other optical sensing operations. This FPS zone can be marked to be visible by displaying images representing the boundaries of a designated FPS zone or displaying an image of the FPS zone.

The peripheral display zone 20 in the specific example is a display area smaller than the main display zone 10 as a bottom task bar zone that can provide various functions, including displaying icons, images or other objects (FIG. 1A and FIG. 1C), displaying information or text messages (FIG. 1B), and displaying an extended portion of a large image displayed in the main display zone so that the two zones 10 and 20 form a single, seamless and contiguous display area (FIG. 1D). Such different display modes or configurations by the two display zones 10 and 20 can be controlled by the control module.

For example, in some implementations, the control module can be used to control the peripheral display zone 20 to display a fingerprint sensing (FPS) zone in the peripheral display zone 20 for a user to place a finger there for fingerprint sensing or other optical sensing. This displayed FPS zone is shown as one of the displayed objects in the peripheral display zone 20 in FIG. 1A. The control module may be used to control the peripheral display zone 20 to display an icon that allows a user to launch an app or perform a function by touching the icon. See FIGS. 1A and 1C. The peripheral display zone 20 may be controlled to display a group of icons at different positions in the peripheral display zone. Also shown in FIG. 1A, different icons can be placed in the peripheral display zone 20 to allow a user to select by touching or to allow user to display additional icons by a sliding touch to move some or all of the currently displayed icons or objects out of the peripheral display zone 20 while placing additional or other icons or objects in the peripheral display zone 20. This expands the functions that can be performed in the peripheral display zone 20.

In some other implementations, the control module can be used to control the peripheral display zone 20 to display a message or information as shown in FIG. 1B. The displayed message or information can be a repetition of the same text message or information or a scrolling of different text messages or information. In the specific screen capture shown FIG. 1B, the main display zone is shown as being turned off but, in other display modes, the main display zone 20 may to turned on to display while using the peripheral display zone for displaying one or more text messages or other information.

FIG. 2A shows an example of a device having a LCD display module to provide the main and peripheral display zones 10 and 20 in the same LCD panel. This example includes a touch sensing display system placed under a top transparent layer 431 such as a cover glass which serves as a user interface surface for various user interfacing operations, including, e.g., touch sensing operations by the user, displaying images to the user, and an optical sensing interface to receive a finger for optical fingerprint sensing and other optical sensing operations where probe light is directed from inside the device to the top cover glass 431 to illuminate the finger. This particular display system example includes a multi-layer LCD module 433 that includes LCD display backlighting light module 434 (e.g., LED lights in edge-lit or back lit backlighting configurations) that provide the white backlighting light for the LCD module 433, and a light waveguide layer 433c coupled to the LCD display backlighting light sources 434 to receive and guide the backlighting light to LCD structure layers 433a (e.g., in edge-lit backlighting configurations). The LCD structure layers 433a can include, e.g., a layer of liquid crystal (LC) cells, LCD electrodes, a transparent conductive ITO layer, front and back optical polarizer layers on two opposite sides of the LCD cells, a color filter layer with color filters for producing colors, and a touch sensing layer for touch sensing operations. As explained below, the LCD structure layers 433a in FIG. 2A are modified as the LCD structure layers 433f to accommodate for the peripheral display zone.

The multi-layer LCD module 433 also includes layers for managing the backlighting light in the light waveguide layer 433c from the LCD display backlighting light sources 434: a backlighting diffuser layer 433b placed underneath the LCD structure layers 433f and above the light waveguide layer 433c to spatially spread the backlighting light for illuminating the LCD display pixels in the LCD structure layers 433f, and an optical reflector film layer 433d underneath the light waveguide layer 433c to recycle backlighting light towards the LCD structure layers 433a for improved light use efficiency and the display brightness.

Different from a multi-layer LCD module in various smartphone or other devices, the multi-layer LCD module 433 has two different display zones: a main display zone 10 and a peripheral display zone 20 as illustrated in FIGS. 1A-1D. Under the peripheral display zone 20, additional modules are provided for the peripheral display zone 20: a designated peripheral display zone illumination module 436b that produces illumination light to illuminate a small peripheral LCD panel area of the multi-layer LCD module 433 as the peripheral display zone 20 to allow the peripheral display zone 20 even when the LCD display backlighting light sources 434 are turned off so that the main display zone 10 of the multi-layer LCD module 433 is turned off due to lack of backlighting. As shown in this example, the designated peripheral display zone illumination module 436b is placed below the multi-layer LCD module 433. Under this design, the illumination light from the designated peripheral display zone illumination module 436b need to penetrate through the optical reflector film layer 433d and the light waveguide layer 433c and the backlighting diffuser layer 433b in order to reach the LCD structure layers 433f in which the LCD pixels are controlled to display images by filtering the received illumination light. Accordingly, the optical reflector film layer 433d is structured to include a partial transmission zone or window in the peripheral display zone 20 to allow the illumination light from the designated peripheral display zone illumination module 436b to transmit through. As one example to achieve this, FIG. 2A shows micro transparent structures 951e are formed in the optical reflector film layer 433d which may be punched holes or other structures providing some optical transmission.

FIG. 2A also illustrates an example of an optical sensor module formed under the multi-layer LCD module 433 in the near the peripheral display zone 20 in order to provide optical sensing on or over the top transparent layer 431. Specifically in this example, such an optical sensor module includes an optical detector array 621a of optical detectors or optical sensors (e.g., photodiodes or other optical sensing elements) to receive and detect optical probe light returned from the top transparent layer 431 for optical detection such as optical fingerprint sensing or other optical sensing. One or more optical probe light sources 436a are provided under the multi-layer LCD module 433 to direct probe light through the multi-layer LCD module 433 to reach the top transparent layer 431 to illuminate the sensing zone in the peripheral display zone 20 for optical sensing and the returned probe light is directed to pass through the multi-layer LCD module 433 to reach the optical detector array 621a. Therefore, the LCD layers 433f can be structured to include a region in the peripheral display zone 20 as a window to exhibit a desired level of optical transmission to allow for transmission of the probe light as shown by a modified window 951c in the LCD layers 433f; similarly, the light diffuser layer 433b can be structured to include a region in the peripheral display zone 20 as an optical window to exhibit a desired level of optical transmission to allow for transmission of the probe light as shown by a modified window 951d in the light diffuser layer 433b. One of the technical challenges for such under LCD optical sensing is undesired background or environment light at the optical detector array 621a and proper optical filtering designs can be used in the light path to reduce or reject such undesired background or environment light by implementing optical filtering films or coatings on a suitable surface of the optical receiving path to the optical detector array 621a.

Therefore, the layers in the multi-layer LCD module 433 in the peripheral display zone 20 in FIG. 2A are modified to accommodate for directing the illumination light from the under-LCD and designated peripheral display zone illumination module 436b and for permitting sufficient transmission of the probe light to facilitate the under-LCD optical sensing. Those regions for transmitting sufficient light in the light diffuser 433b and other LCD layers 433f may be formed in different ways, including, e.g., including forming transparent holes, using a transparent or partial transparent material, to align the detection light path at proper angles, or to cut off or otherwise remove some of the scattering materials (such as light diffuser, prism films) in that region in the peripheral display zone 20.

In the illustrated example, a circuit board layer 623 is provided under the multi-layer LCD module 433 to support the designated peripheral display zone illumination module 436b, one or more optical probe light sources 436a and the optical detector array 621a for optical sensing in the peripheral display zone 20.

Probe light sources 436a may be designed to emit probe light at one or more suitable wavelengths, e.g., in the near infrared spectral range beginning at the longer visible red wavelengths (e.g., the 940 nm band) which can partially transmit through the reflector films and the liquid crystal cell polarizers at proper incident angles. The probe light sources 436a may be set at optical wavelengths different from the wavelengths of the backlighting illumination light from the light source module 434 so that the light guide function of the waveguide 433c is not effective to the light from the illumination light sources 436a so that the probe light from the 436a can be more efficiently to pass through to reach the top transparent layer 431 above of the LCD panel for illuminating a finger. Various optical systems can be designed for the optical sensor module under the LCD display. For example, the probe light may be collimated if the receiving optics for directing the returned probe light to the optical detector array 621a is lensless. Some specific examples of optical sensor module designs are disclosed in later sections of this patent document.

In some implementations, the designated illumination light sources 436b in the peripheral display zone or the task bar area 20 can be designed to provide low power-consumption illumination for displaying icons or images when the main display back lighting 434 is turned off. The designated illumination light sources 436b should be in the visible spectral range to provide colored or monochromatic displays in the peripheral display zone or the task bar area 20, e.g., white light.

Figure 2B:
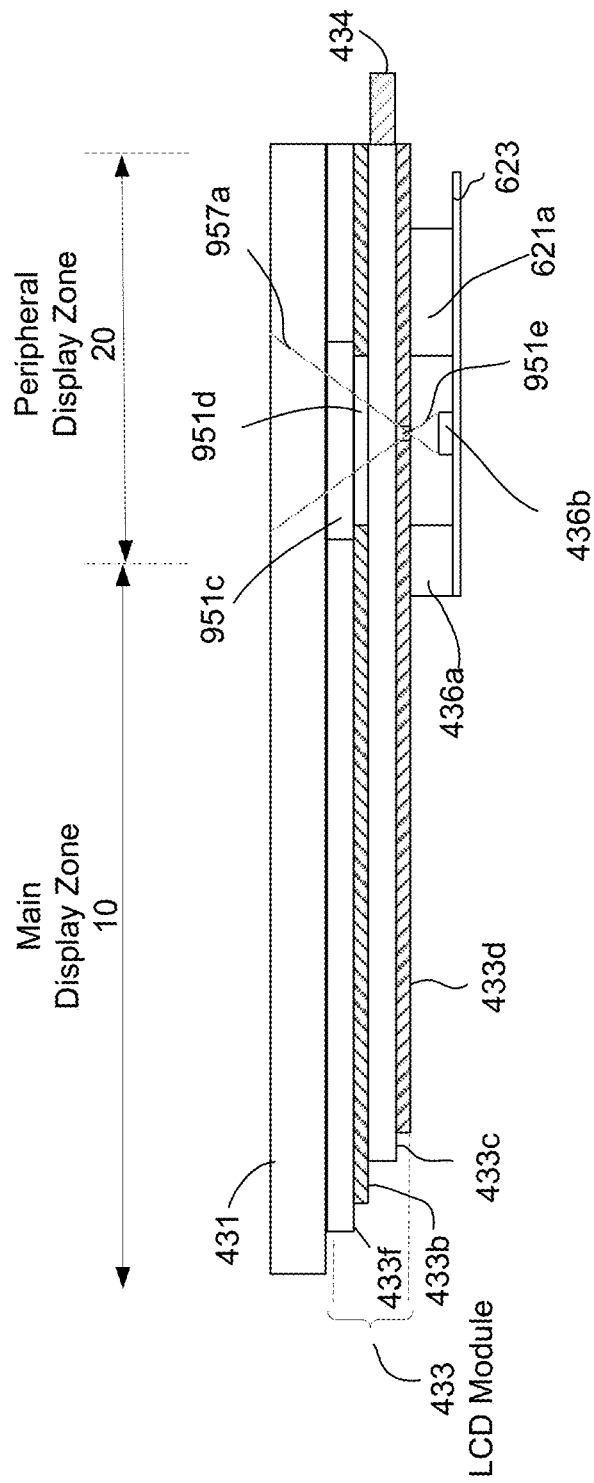

FIG. 2B illustrates the illumination operation by the designated illumination light sources 436b in the peripheral display zone or the task bar area 20 where the micro transparent structures 951e formed in the optical reflector film layer 433d receive task bar illumination light 957a from the designated illumination light sources 436b which can be controlled independent from the main display back lighting light sources 434. The task bar light sources 436b can be used to illuminate the entire region or a part of the peripheral display zone or the task bar area 20.

FIG. 2C shows another example of a device having a LCD display module to provide the main and peripheral display zones in the same LCD panel. Different from the example in FIG. 2A, one or more designated illumination light sources 436c for providing illumination light to the LCD pixels in the peripheral display zone 20 are placed inside the LCD module 433 rather than below the LCD module 433 while still placing the optical detector array 621a and the one or more probe light sources 436a under the LCD module 433. Specifically, the light source module for the one or more designated illumination light sources 436c may be in the treated region 951d of the light diffuser 433b or 951c of LCD layers 433f so the produced illumination visible light can reach the LCD pixels in the LCD module 433 within the peripheral display zone 20.

Figure 2D:
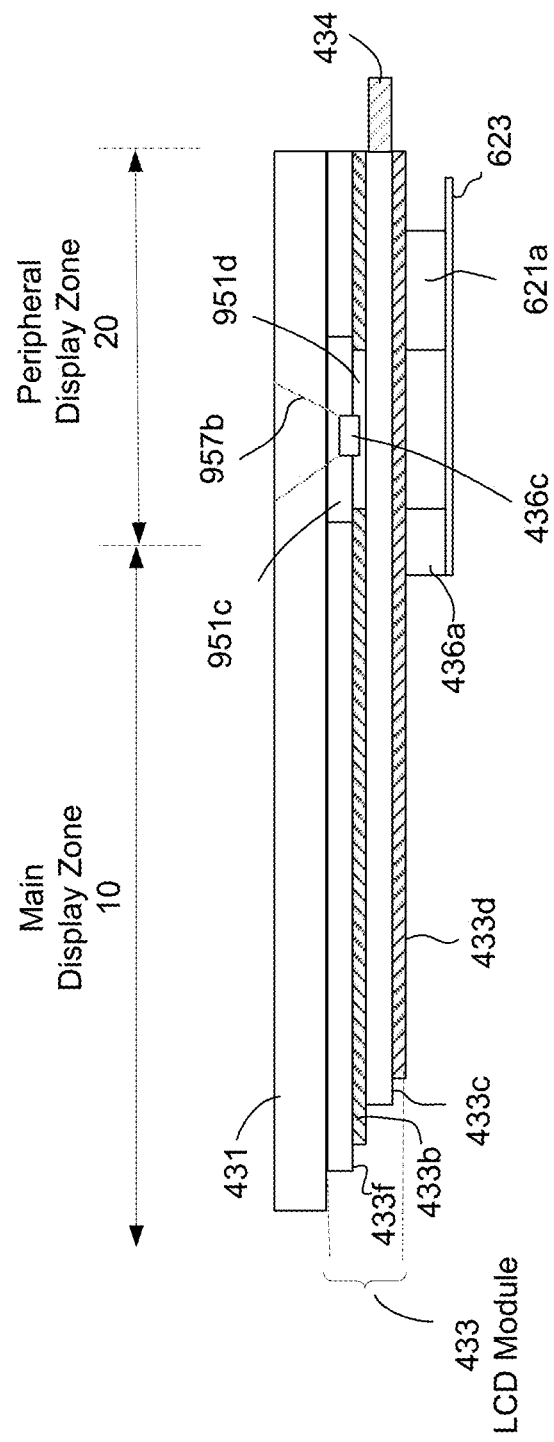

FIG. 2D illustrates the illumination operation by the designated illumination light sources 436c in the peripheral display zone or the task bar area 20 which can be controlled independent from the main display back lighting light sources 434. The task bar light sources 436c can be used to illuminate the entire region or a part of the peripheral display zone or the task bar area 20.

In some implementations, a separate peripheral display zone illumination waveguide may be provided as sidebar illumination light guide to receive the light from the one or more task bar light sources 436c or 436b and to distribute the light uniformly in the task bar 20. FIG. 2E shows an example where a regional light waveguide structure 2000 is formed inside the LCD module 433 as a peripheral display zone illumination waveguide to cover the peripheral display zone 20 of the LCD layers 433f. The regional light waveguide structure 2000 is separated from the LCD waveguide 433c which distributing illumination from the main backlighting light module 434 to the entire LCD layers 433f for both the main display zone 10 and the peripheral display zone 20. Under this design, the regional light waveguide structure 2000 is a designed waveguide to receive the illumination light from the one or more task bar light sources 436c and is operated to spatially distribute the received illumination light from the one or more task bar light sources 436c in a more spatially uniform manner at different LCD pixel locations in the peripheral display zone 20.

The regional light waveguide structure for illuminating the peripheral display zone 20 can be placed at other locations different from what is shown in the example in FIG. 2E and the presence of the regional light waveguide structure can be used to provide some design flexibility in placing the one or more designated illumination light sources as long as the output illumination light from the one or more designated illumination light sources can be coupled into the regional light waveguide structure. FIG. 2F shows another example where a regional light waveguide structure 2000 is formed inside the LCD module 433 to cover the peripheral display zone 20 of the LCD layers 433f. As shown in the specific design in FIG. 2F, one or more designated illumination light sources 436f are located at an edge of the LCD layers 433f, rather than in the OCD layers 433f in the example in FIG. 2E, and is optically coupled to the regional light waveguide structure 2000 located inside the LCD layers 433f. This particular placement of the one or more designated illumination light sources 436f simplified the multi-layer structure of the LCD with independently operated peripheral display zone 20 and under-LCD optical sensor.

In the examples in FIGS. 2A, 2C, 2E and 2F having the main and peripheral display zones in the same LCD panel, three different illumination light sources are provided: (1) a backlighting module 434 for supplying visible or white illumination light to both the main and peripheral display zones in the same LCD panel, (2) a designated illumination light module with one or more light sources 436b or 436c to provide designated illumination light to the LCD pixels in the LCD module 433 within the peripheral display zone 20 to allow display operation of the peripheral display zone 20 when the backlighting module 434 is turned off, and (3) a probe light module with one or more probe light sources 436a for under-LCD optical sensing. Various light illumination operations may be implemented. For another example, different from the backlighting module 434 and the designated illumination light module with one or more light sources 436b or 436c, the illumination light probe light module with one or more probe light sources 436a for under-LCD optical sensing, like other probe light sources for optical sensing, can be designed to emit probe light for optical sensing at one or more optical wavelengths different from the LCD display illumination light wavelengths and can be, e.g., in the infrared spectral range beyond the visible spectral range or in the visible spectral range and can be used to use different probe wavelengths to probe different optical response characteristics from an object or a finger. The illumination light sources for optical sensing can be placed in the same general locations (e.g., below the reflector film 433d next to or adjacent to the optical sensor), or at different locations where one or more are placed under the LCD module and one or more near an edge of the LCD module under the top transparent layer 431.

The subsequent sections describe designs and features of a display screen module and an optical sensor module under the display screen for performing fingerprint sensing and other optical sensing of a finger or object in touch or near the top surface of the display screen. Such under-screen optical sensing designs can be used in a 2-zone display with both a main display zone and a peripheral display zone as well a single-zone display without the peripheral display zone.

Electronic devices or systems may be equipped with fingerprint authentication mechanisms to improve the security for accessing the devices. Such electronic devices or system may include, portable or mobile computing devices, e.g., smartphones, tablet computers, wrist-worn devices and other wearable or portable devices, larger electronic devices or systems, e.g., personal computers in portable forms or desktop forms, ATMs, various terminals to various electronic systems, databases, or information systems for commercial or governmental uses, motorized transportation systems including automobiles, boats, trains, aircraft and others.

Fingerprint sensing is useful in mobile applications and other applications that use or require secure access. For example, fingerprint sensing can be used to provide secure access to a mobile device and secure financial transactions including online purchases. It is desirable to include robust and reliable fingerprint sensing suitable for mobile devices and other applications. In mobile, portable or wearable devices, it is desirable for fingerprint sensors to minimize or eliminate the footprint for fingerprint sensing given the limited space on those devices, especially considering the demands for a maximum display area on a given device.

The light produced by a display screen for displaying images necessarily passes through the top surface of the display screen in order to be viewed by a user. A finger can touch the top surface and thus interacts with the light at the top surface to cause the reflected or scattered light at the surface area of the touch to carry spatial image information of the finger to return to the display panel underneath the top surface. In touch sensing display devices, the top surface is the touch sensing interface with the user and this interaction between the light for displaying images and the user finger or hand constantly occurs but such information-carrying light returning back to the display panel is largely wasted and is not used in most touch sensing devices. In various mobile or portable devices with touch sensing displays and fingerprint sensing functions, a fingerprint sensor tends to be a separate device from the display screen, either placed on the same surface of the display screen at a location outside the display screen area such as in some models of Apple iPhones and Samsung smartphones, or placed on the backside of a smartphone, such as some models of smart phones by Huawei, Lenovo, Xiaomi or Google, to avoid taking up valuable space for placing a large display screen on the front side. Those fingerprint sensors are separate devices from the display screens and thus need to be compact to save space for display and other functions while still providing reliable and fast fingerprint sensing with a spatial image resolution above a certain acceptable level. However, the need to be compact and small and the need to provide a high spatial image resolution in capturing a fingerprint pattern are in direct conflict with each other in many fingerprint sensors because a high spatial image resolution in capturing a fingerprint pattern in based on various suitable fingerprint sensing technologies (e.g., capacitive touch sensing or optical imaging) requires a large sensor area with a large number of sensing pixels.

The sensor technology and examples of implementations of the sensor technology described in this patent document provide an optical sensor module that uses, at least in part, the light from a display screen as the illumination probe light to illuminate a fingerprint sensing area on the touch sensing surface of the display screen to perform one or more sensing operations based on optical sensing of such light. A suitable display screen for implementing the disclosed optical sensor technology can be based on various display technologies or configurations, including, a display screen having light emitting display pixels without using backlight where each individual pixel generates light for forming a display image on the screen such as liquid crystal display (LCD) screens an organic light emitting diode (OLED) display screens, or electroluminescent display screens.

In the disclosed examples for integrating optical sensing to LCD based on the disclosed optical sensor technology, the under LCD optical sensor can be used to detect a portion of the light that is used for displaying images in a LCD screen where such a portion of the light for the display screen may be the scattered light, reflected light or some stray light. For example, in some implementations, the image light of the LCD screen based on backlighting may be reflected or scattered back into the LCD display screen as returned light when encountering an object such as a user finger or palm, or a user pointer device like a stylus. Such returned light can be captured for performing one or more optical sensing operations using the disclosed optical sensor technology. Due to the use of the light from LCD screen for optical sensing, an optical sensor module based on the disclosed optical sensor technology is specially designed to be integrated to the LCD display screen in a way that maintains the display operations and functions of the LCD display screen without interference while providing optical sensing operations and functions to enhance overall functionality, device integration and user experience of an electronic device or system such as a smart phone, a tablet, or a mobile/wearable device.

In addition, in various implementations of the disclosed optical sensing technology, one or more designated probe light sources may be provided to produce additional illumination probe light for the optical sensing operations by the under LCD screen optical sensing module. In such applications, the light from the backlighting of the LCD screen and the probe light from the one or more designated probe light sources collectively form the illumination light for optical sensing operations.

Regarding the additional optical sensing functions beyond fingerprint detection, the optical sensing may be used to measure other parameters. For example, the disclosed optical sensor technology can measure a pattern of a palm of a person given the large touch area available over the entire LCD display screen (in contrast, some designated fingerprint sensors such as the fingerprint sensor in the home button of Apple's iPhone/iPad devices have a rather small and designated off-screen fingerprint sensing area that is highly limited in the sensing area size that may not be suitable for sensing large patterns). For yet another example, the disclosed optical sensor technology can be used not only to use optical sensing to capture and detect a pattern of a finger or palm that is associated with a person, but also to use optical sensing or other sensing mechanisms to detect whether the captured or detected pattern of a fingerprint or palm is from a live person's hand by a "live finger" detection mechanism, which may be based on, for example, the different optical absorption behaviors of the blood at different optical wavelengths, the fact that a live person's finger tends to be moving or stretching due to the person's natural movement or motion (either intended or unintended) or pulsing when the blood flows through the person's body in connection with the heartbeat. In one implementation, the optical sensor module can detect a change in the returned light from a finger or palm due to the heartbeat/blood flow change and thus to detect whether there is a live heartbeat in the object presented as a finger or palm. The user authentication can be based on the combination of the both the optical sensing of the fingerprint/palm pattern and the positive determination of the presence of a live person to enhance the access control. For yet another example, the optical sensor module may include a sensing function for measuring a glucose level or a degree of oxygen saturation based on optical sensing in the returned light from a finger or palm. As yet another example, as a person touches the LCD display screen, a change in the touching force can be reflected in one or more ways, including fingerprint pattern deforming, a change in the contacting area between the finger and the screen surface, fingerprint ridge widening, or a blood flow dynamics change. Those and other changes can be measured by optical sensing based on the disclosed optical sensor technology and can be used to calculate the touch force. This touch force sensing can be used to add more functions to the optical sensor module beyond the fingerprint sensing.

With respect to useful operations or control features in connection with the touch sensing aspect of the LCD display screen, the disclosed optical sensor technology can provide triggering functions or additional functions based on one or more sensing results from the optical sensor module to perform certain operations in connection with the touch sensing control over the LCD display screen. For example, the optical property of a finger skin (e.g., the index of refraction) tends to be different from other artificial objects. Based on this, the optical sensor module may be designed to selectively receive and detect returned light that is caused by a finger in touch with the surface of the LCD display screen while returned light caused by other objects would not be detected by the optical sensor module. This object-selective optical detection can be used to provide useful user controls by touch sensing, such as waking up the smartphone or device only by a touch via a person's finger or palm while touches by other objects would not cause the device to wake up for energy efficient operations and to prolong the battery use. This operation can be implemented by a control based on the output of the optical sensor module to control the waking up circuitry operation of the LCD display screen which, the LCD pixels are put in a "sleep" mode by being turned off (and the LCD backlighting is also turned off) while one or more illumination light sources (e.g., LEDs) for the under-LCD panel optical sensor module are turned on in a flash mode to intermittently emit flash light to the screen surface for sensing any touch by a person's finger or palm. Under this design, the optical sensor module operates the one or more illumination light sources to produce the "sleep" mode wake-up sensing light flashes so that the optical sensor module can detect returned light of such wake-up sensing light caused by the finger touch on the LCD display screen and, upon a positive detection, the LCD backlighting and the LCD display screen are turned on or "woken up". In some implementations, the wake-up sensing light can be in the infrared invisible spectral range so a user will not experience any visual of a flash light. The LCD display screen operation can be controlled to provide an improved fingerprint sensing by eliminating background light for optical sensing of the fingerprint. In one implementation, for example, each display scan frame generates a frame of fingerprint signals. If, two frames of fingerprint signals with the display are generated in one frame when the LCD display screen is turned on and in the other frame when the LCD display screen is turned off, the subtraction between those two frames of signals can be used to reduce the ambient background light influence. By operating the fingerprint sensing frame rate is at one half of the display frame rate in some implementations, the background light noise in fingerprint sensing can be reduced.

An optical sensor module based on the disclosed optical sensor technology can be coupled to the backside of the LCD display screen without requiring creation of a designated area on the surface side of the LCD display screen that would occupy a valuable device surface real estate in some electronic devices such as a smartphone, a tablet or a wearable device. This aspect of the disclosed technology can be used to provide certain advantages or benefits in both device designs and product integration or manufacturing.

In some implementations, an optical sensor module based on the disclosed optical sensor technology can be configured as a non-invasive module that can be easily integrated to a display screen without requiring changing the design of the LCD display screen for providing a desired optical sensing function such as fingerprint sensing. In this regard, an optical sensor module based on the disclosed optical sensor technology can be independent from the design of a particular LCD display screen design due to the nature of the optical sensor module: the optical sensing of such an optical sensor module is by detecting the light that is emitted by the one or more illumination light sources of the optical sensor module and is returned from the top surface of the display area, and the disclosed optical sensor module is coupled to the backside of the LCD display screen as a under-screen optical sensor module for receiving the returned light from the top surface of the display area and thus does not require a special sensing port or sensing area that is separate from the display screen area. Accordingly, such a under-screen optical sensor module can be used to combine with a LCD display screen to provide optical fingerprint sensing and other sensor functions on an LCD display screen without using a specially designed LCD display screen with hardware especially designed for providing such optical sensing. This aspect of the disclosed optical sensor technology enables a wide range of LCD display screens in smartphones, tablets or other electronic devices with enhanced functions from the optical sensing of the disclosed optical sensor technology.

For example, for an existing phone assembly design that does not provide a separate fingerprint sensor as in certain Apple iPhones or Samsung Galaxy smartphones, such an existing phone assembly design can integrate the under-screen optical sensor module as disclosed herein without changing the touch sensing-display screen assembly to provide an added on-screen fingerprint sensing function. Because the disclosed optical sensing does not require a separate designated sensing area or port as in the case of certain Apple iPhones/Samsung Galaxy phones with a front fingerprint sensor outside the display screen area, or some smartphones with a designated rear fingerprint sensor on the backside like in some models by Huawei, Xiaomi, Google or Lenovo, the integration of the on-screen fingerprint sensing disclosed herein does not require a substantial change to the existing phone assembly design or the touch sensing display module that has both the touch sensing layers and the display layers. Based on the disclosed optical sensing technology in this document, no external sensing port and no extern hardware button are needed on the exterior of a device are needed for adding the disclosed optical sensor module for fingerprint sensing. The added optical sensor module and the related circuitry are under the display screen inside the phone housing and the fingerprint sensing can be conveniently performed on the same touch sensing surface for the touch screen.

For another example, due to the above described nature of the optical sensor module for fingerprint sensing, a smartphone that integrates such an optical sensor module can be updated with improved designs, functions and integration mechanism without affecting or burdening the design or manufacturing of the LCD display screens to provide desired flexibility to device manufacturing and improvements/upgrades in product cycles while maintaining the availability of newer versions of optical sensing functions to smartphones, tablets or other electronic devices using LCD display screens. Specifically, the touch sensing layers or the LCD display layers may be updated in the next product release without adding any significant hardware change for the fingerprint sensing feature using the disclosed under-screen optical sensor module. Also, improved on-screen optical sensing for fingerprint sensing or other optical sensing functions by such an optical sensor module can be added to a new product release by using a new version of the under-screen optical sensor module without requiring significant changes to the phone assembly designs, including adding additional optical sensing functions.

The above and other features of the disclosed optical sensor technology can be implemented to provide a new generation of electronic devices with improved fingerprint sensing and other sensing functions, especially for smartphones, tablets and other electronic devices with LCD display screens to provide various touch sensing operations and functions and to enhance the user experience in such devices. The features for optical sensor modules disclosed in this patent document may be applicable to various display panels based on different technologies including both LCD and OLED displays. The specific examples below are directed to LCD display panels and optical sensor modules placed under LCD display panels.

In implementations of the disclosed technical features, additional sensing functions or sensing modules, such as a biomedical sensor, e.g., a heartbeat sensor in wearable devices like wrist band devices or watches, may be provided. In general, different sensors can be provided in electronic devices or systems to achieve different sensing operations and functions.

The disclosed technology can be implemented to provide devices, systems, and techniques that perform optical sensing of human fingerprints and authentication for authenticating an access attempt to a locked computer-controlled device such as a mobile device or a computer-controlled system, that is equipped with a fingerprint detection module. The disclosed technology can be used for securing access to various electronic devices and systems, including portable or mobile computing devices such as laptops, tablets, smartphones, and gaming devices, and other electronic devices or systems such as electronic databases, automobiles, bank ATMs, etc.

Figure 3A:
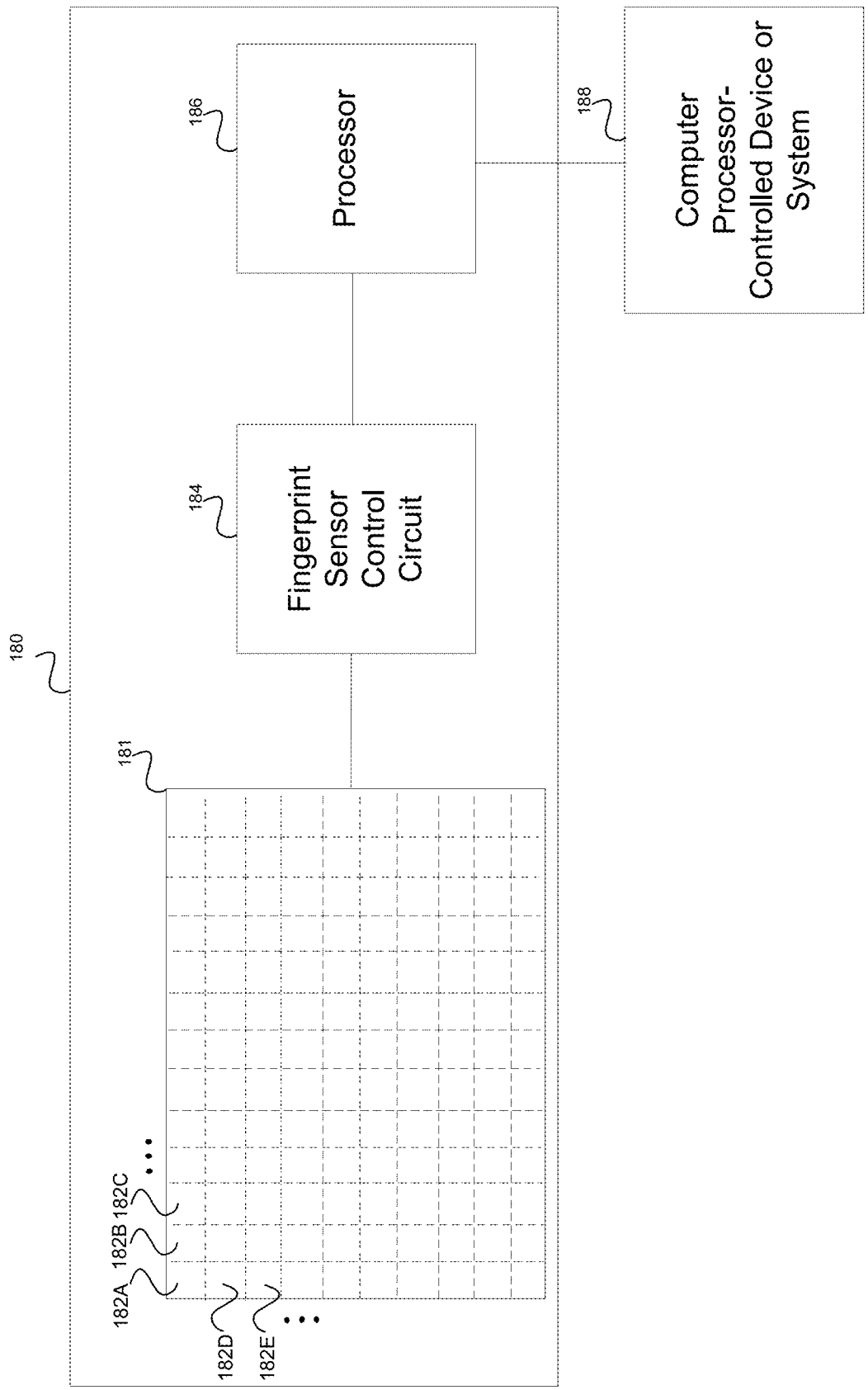
FIG. 3A is a block diagram of an example of a system with a fingerprint sensing module which can be implemented to include an optical fingerprint sensor disclosed in this document.

FIG. 3A is a block diagram of an example of a system 180 with a fingerprint sensing module 180 including a fingerprint sensor 181 which can be implemented to include an optical fingerprint sensor based on the optical sensing of fingerprints as disclosed in this document. The system 180 includes a fingerprint sensor control circuit 184, and a digital processor 186 which may include one or more processors for processing fingerprint patterns and determining whether an input fingerprint pattern is one for an authorized user. The fingerprint sensing system 180 uses the fingerprint sensor 181 to obtain a fingerprint and compares the obtained fingerprint to a stored fingerprint to enable or disable functionality in a device or system 188 that is secured by the fingerprint sensing system 180. In operation, the access to the device 188 is controlled by the fingerprint processing processor 186 based on whether the captured user fingerprint is from an authorized user. As illustrated, the fingerprint sensor 181 may include multiple fingerprint sensing pixels such as pixels 182A-182E that collectively represent at least a portion of a fingerprint. For example, the fingerprint sensing system 180 may be implemented at an ATM as the system 188 to determine the fingerprint of a customer requesting to access funds or other transactions. Based on a comparison of the customer's fingerprint obtained from the fingerprint sensor 181 to one or more stored fingerprints, the fingerprint sensing system 180 may, upon a positive identification, cause the ATM system 188 to grant the requested access to the user account, or, upon a negative identification, may deny the access. For another example, the device or system 188 may be a smartphone or a portable device and the fingerprint sensing system 180 is a module integrated to the device 188. For another example, the device or system 188 may be a gate or secured entrance to a facility or home that uses the fingerprint sensor 181 to grant or deny entrance. For yet another example, the device or system 188 may be an automobile or other vehicle that uses the fingerprint sensor 181 to link to the start of the engine and to identify whether a person is authorized to operate the automobile or vehicle.

Figure 3B:
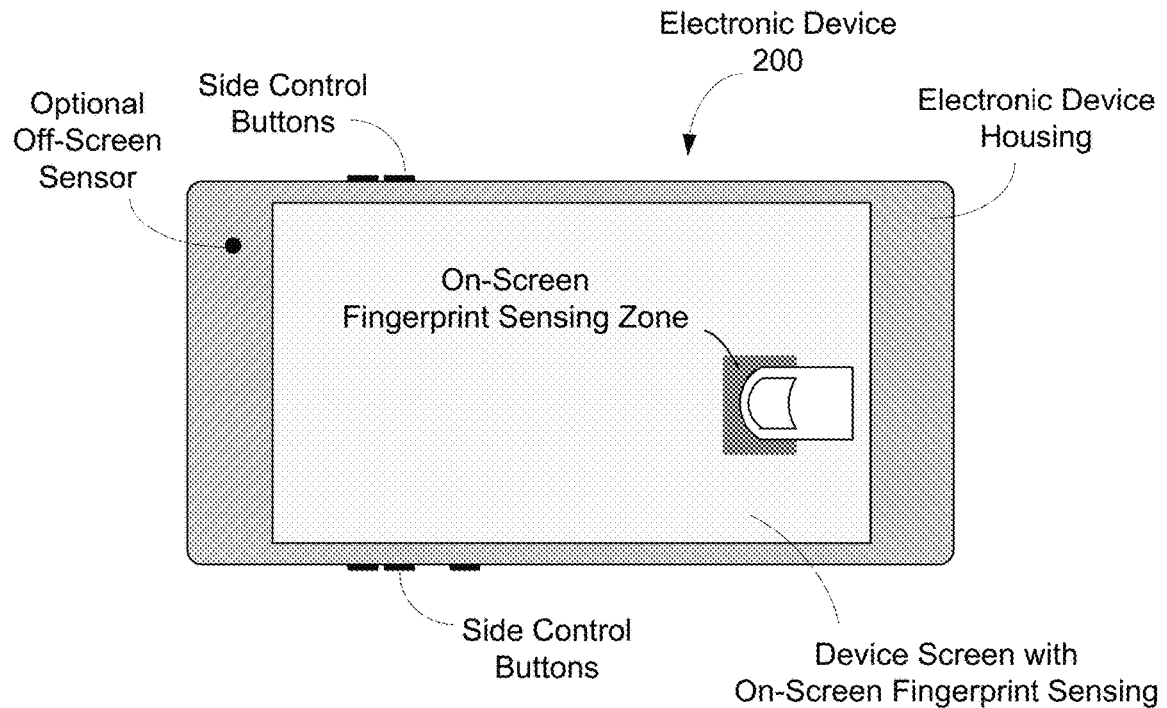
FIGS. 3B and 3C illustrate one exemplary implementation of an electronic device 200 having a touch sensing display screen assembly and an optical sensor module positioned underneath the touch sensing display screen assembly.
Figure 3C:
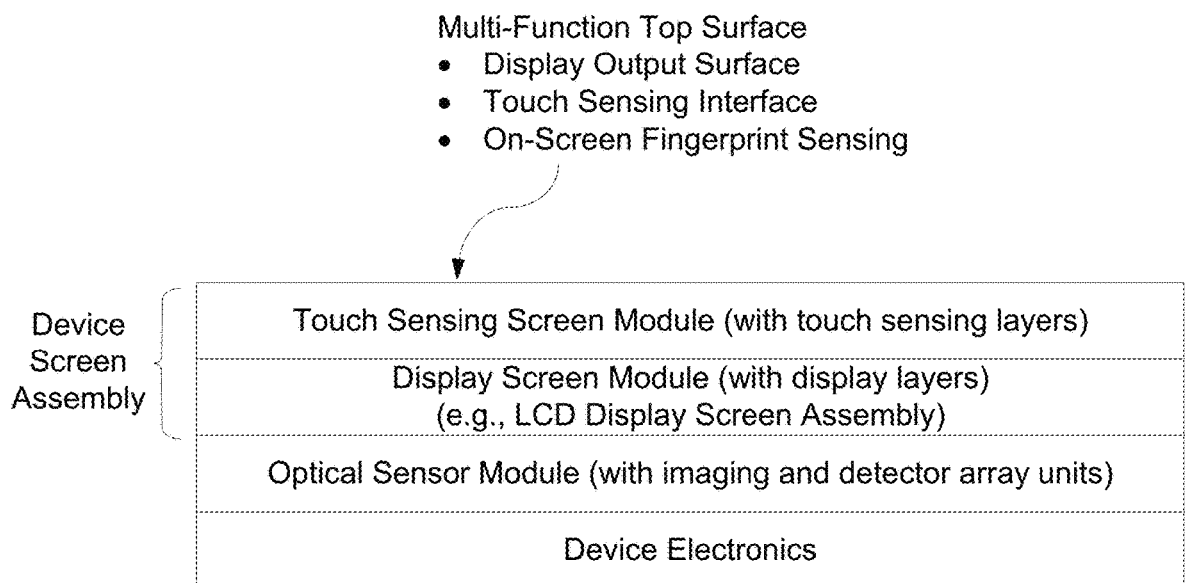

As a specific example, FIGS. 3B and 3C illustrate one exemplary implementation of an electronic device 200 having a touch sensing display screen assembly and an optical sensor module positioned underneath the touch sensing display screen assembly. In this particular example, the display technology can be implemented by a LCD display screen with backlight for optically illuminating the LCD pixels or another display screen having light emitting display pixels without using backlight (e.g., an OLED display screen). The electronic device 200 can be a portable device such as a smartphone or a tablet and can be the device 188 as shown in FIG. 3A.

FIG. 3B shows the front side of the device 200 which may resemble some features in some existing smartphones or tablets. The device screen is on the front side of the device 200 occupying either entirety, a majority or a significant portion of the front side space and the fingerprint sensing function is provided on the device screen, e.g., one or more sensing areas for receiving a finger on the device screen. As an example, FIG. 3B shows a fingerprint sensing zone in the device screen for a finger to touch which may be illuminated as a visibly identifiable zone or area for a user to place a finger for fingerprint sensing. Such a fingerprint sensing zone can function like the rest of the device screen for displaying images. As illustrated, the device housing of the device 200 may have, in various implementations, side facets that support side control buttons that are common in various smartphones on the market today. Also, one or more optional sensors may be provided on the front side of the device 200 outside the device screen as illustrated by one example on the left upper corner of the device housing in FIG. 3B.

FIG. 3C shows an example of the structural construction of the modules in the device 200 relevant to the optical fingerprint sensing disclosed in this document. The device screen assembly shown in FIG. 3C includes, e.g., the touch sensing screen module with touch sensing layers on the top, and a display screen module with display layers located underneath the touch sensing screen module. An optical sensor module is coupled to, and located underneath, the display screen assembly module to receive and capture the returned light from the top surface of the touch sensing screen module and to guide and image the returned light onto an optical detector array of optical sensing pixels or photodetectors which convert the optical image in the returned light into pixel signals for further processing. Underneath the optical sensor module is the device electronics structure containing certain electronic circuits for the optical sensor module and other parts in the device 200. The device electronics may be arranged inside the device housing and may include a part that is under the optical sensor module as shown in FIG. 3C.

In implementations, the top surface of the device screen assembly can be a surface of an optically transparent layer serving as a user touch sensing surface to provide multiple functions, such as (1) a display output surface through which the light carrying the display images passes through to reach a viewer's eyes, (2) a touch sensing interface to receive a user's touches for the touch sensing operations by the touch sensing screen module, and (3) an optical interface for on-screen fingerprint sensing (and possibly one or more other optical sensing functions). This optically transparent layer can be a rigid layer such as a glass or crystal layer or a flexible layer.

One example of a display screen is an LCD display having LCD layers and a thin film transistor (TFT) structure or substrate. A LCD display panel is a multi-layer liquid crystal display (LCD) module that includes LCD display backlighting light sources (e.g., LED lights) emitting LCD illumination light for LCD pixels, a light waveguide layer to guide the backlighting light, and LCD structure layers which can include, e.g., a layer of liquid crystal (LC) cells, LCD electrodes, transparent conductive ITO layer, an optical polarizer layer, a color filter layer, and a touch sensing layer. The LCD module also includes a backlighting diffuser underneath the LCD structure layers and above the light waveguide layer to spatially spread the backlighting light for illuminating the LCD display pixels, and an optical reflector film layer underneath the light waveguide layer to recycle backlighting light towards the LCD structure layers for improved light use efficiency and the display brightness.

Referring to FIG. 3C, the optical sensor module in this example is placed under the LCD display panel to capture the returned light from the top touch sensing surface and to acquire high resolution images of fingerprint patterns when user's finger is in touch with a sensing area on the top surface. In other implementations, the disclosed under-screen optical sensor module for fingerprint sensing may be implemented on a device without the touch sensing feature. In addition, a suitable display panel may be in various screen designs different from OLED displays.

Figure 3D:
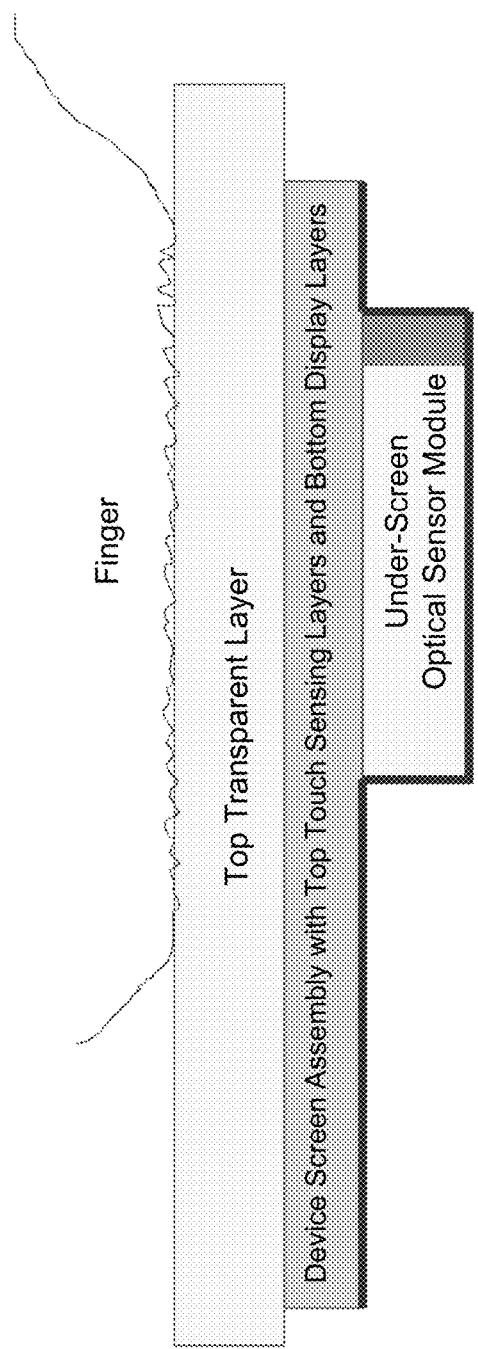
FIGS. 3D and 3E illustrate an example of a device that implements the optical sensor module in FIGS. 3B and 3C.
Figure 3E:
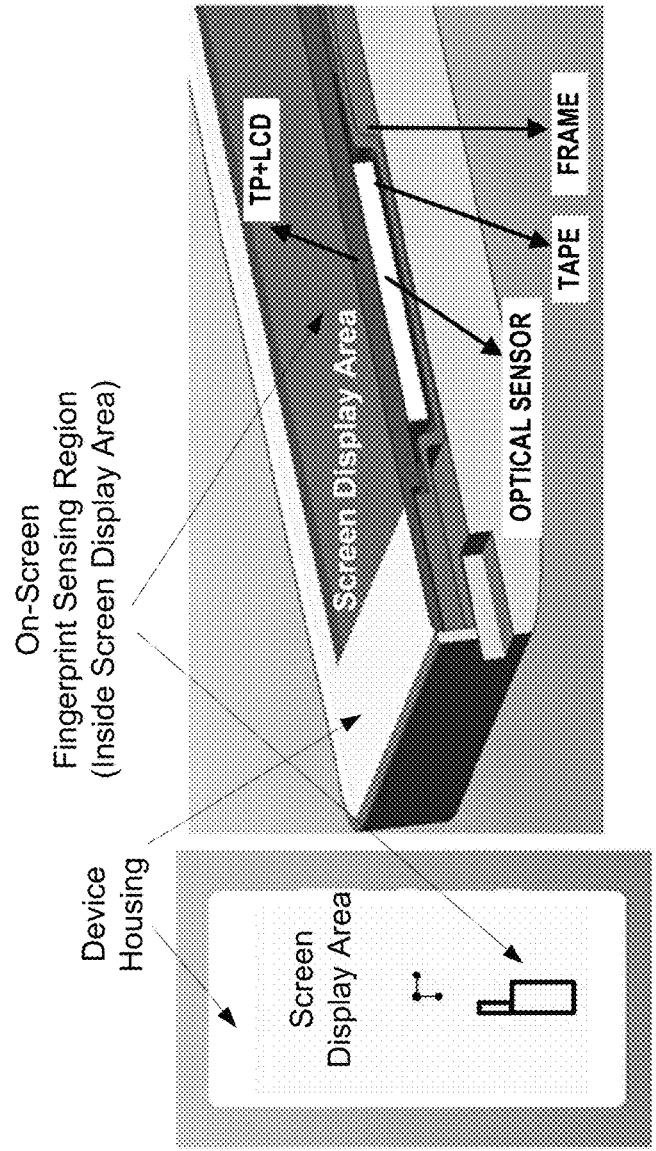

FIGS. 3D and 3E illustrate an example of a device that implements the optical sensor module in FIGS. 3B and 3C. FIG. 3D shows a cross sectional view of a portion of the device containing the under-screen optical sensor module. FIG. 3D shows, on the left, a view of the front side of the device with the touch sensing display indicating a fingerprint sensing area on the lower part of the display screen, and on the right, a perspective view of a part of the device containing the optical sensor module that is under the device display screen assembly. FIG. 3D also shows an example of the layout of the flexible tape with circuit elements.

In the design examples in FIGS. 3B, 3C, 3D and 3E, the optical fingerprint sensor design is different from some other fingerprint sensor designs using a separate fingerprint sensor structure from the display screen with a physical demarcation between the display screen and the fingerprint sensor (e.g., a button like structure in an opening of the top glass cover in some mobile phone designs) on the surface of the mobile device. In the illustrated designs here, the optical fingerprint sensor for detecting fingerprint sensing and other optical signals are located under the top cover glass or layer (e.g., FIG. 3D) so that the top surface of the cover glass serves as the top surface of the mobile device as a contiguous and uniform glass surface across both the display screen layers and the optical detector sensor that are vertically stacked and vertically overlap. This design for integrating optical fingerprint sensing and the touch sensitive display screen under a common and uniform surface provides benefits, including improved device integration, enhanced device packaging, enhanced device resistance to exterior elements, failure and wear and tear, and enhanced user experience over the ownership period of the device.

Referring back to FIGS. 3B and 3C, the illustrated under-screen optical sensor module for on-screen fingerprint sensing may be implemented in various configurations.

In one implementation, a device based on the above design can be structured to include a device screen that provides touch sensing operations and includes a LCD display panel structure for forming a display image, a top transparent layer formed over the device screen as an interface for being touched by a user for the touch sensing operations and for transmitting the light from the display structure to display images to a user, and an optical sensor module located below the display panel structure to receive light that returns from the top transparent layer to detect a fingerprint.

This device and other devices disclosed in this document can be further configured to include various features.

For example, a device electronic control module can be included in the device to grant a user's access to the device if a detected fingerprint matches a fingerprint an authorized user. In addition, the optical sensor module is configured to, in addition to detecting fingerprints, also detect a biometric parameter different form a fingerprint by optical sensing to indicate whether a touch at the top transparent layer associated with a detected fingerprint is from a live person, and the device electronic control module is configured to grant a user's access to the device if both (1) a detected fingerprint matches a fingerprint an authorized user and (2) the detected biometric parameter indicates the detected fingerprint is from a live person. The biometric parameter can include, e.g., whether the finger contains a blood flow, or a heartbeat of a person.

For example, the device can include a device electronic control module coupled to the display panel structure to supply power to the light emitting display pixels and to control image display by the display panel structure, and, in a fingerprint sensing operation, the device electronic control module operates to turn off the light emitting display pixels in one frame to and turn on the light emitting display pixels in a next frame to allow the optical detector array to capture two fingerprint images with and without the illumination by the light emitting display pixels to reduce background light in fingerprint sensing.

For another example, a device electronic control module may be coupled to the display panel structure to supply power to the LCD display panel and to turn off power to the backlighting of the LCD display panel in a sleep mode, and the device electronic control module may be configured to wake up the display panel structure from the sleep mode when the optical sensor module detects the presence of a person's skin at the designated fingerprint sensing region of the top transparent layer. More specifically, in some implementations, the device electronic control module can be configured to operate one or more illumination light sources in the optical sensor module to intermittently emit light, while turning off power to the LCD display panel (in the sleep mode), to direct the intermittently emitted illumination light to the designated fingerprint sensing region of the top transparent layer for monitoring whether there is a person's skin in contact with the designated fingerprint sensing region for waking up the device from the sleep mode.

For another example, the device can include a device electronic control module coupled to the optical sensor module to receive information on multiple detected fingerprints obtained from sensing a touch of a finger and the device electronic control module is operated to measure a change in the multiple detected fingerprints and determines a touch force that causes the measured change. For instance, the change may include a change in the fingerprint image due to the touch force, a change in the touch area due to the touch force, or a change in spacing of fingerprint ridges.

For another example, the top transparent layer can include a designated fingerprint sensing region for a user to touch with a finger for fingerprint sensing and the optical sensor module below the display panel structure can include a transparent block in contact with the display panel substrate to receive light that is emitted from the display panel structure and returned from the top transparent layer, an optical detector array that receives the light and an optical imaging module that images the received light in the transparent block onto the optical detector array. The optical sensor module can be positioned relative to the designated fingerprint sensing region and structured to selectively receive returned light via total internal reflection at the top surface of the top transparent layer when in contact with a person's skin while not receiving the returned light from the designated fingerprint sensing region in absence of a contact by a person's skin.

For yet another example, the optical sensor module can be structured to include an optical wedge located below the display panel structure to modify a total reflection condition on a bottom surface of the display panel structure that interfaces with the optical wedge to permit extraction of light out of the display panel structure through the bottom surface, an optical detector array that receives the light from the optical wedge extracted from the display panel structure, and an optical imaging module located between the optical wedge and the optical detector array to image the light from the optical wedge onto the optical detector array.

Specific examples of under-screen optical sensor modules for on-screen fingerprint sensing are provided below.

Figure 4A:
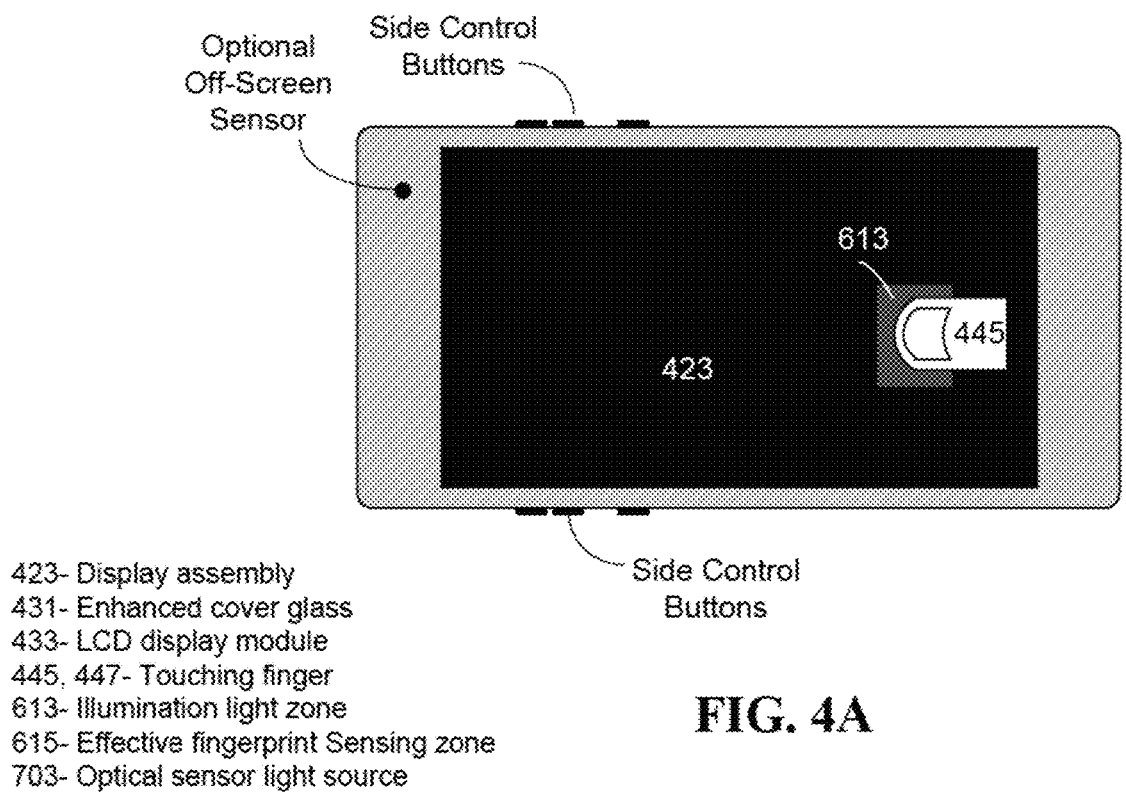
FIGS. 4A and 4B show an example of one implementation of an optical sensor module under the display screen assembly for implementing the design in FIGS. 3B and 3C.
Figure 4B:
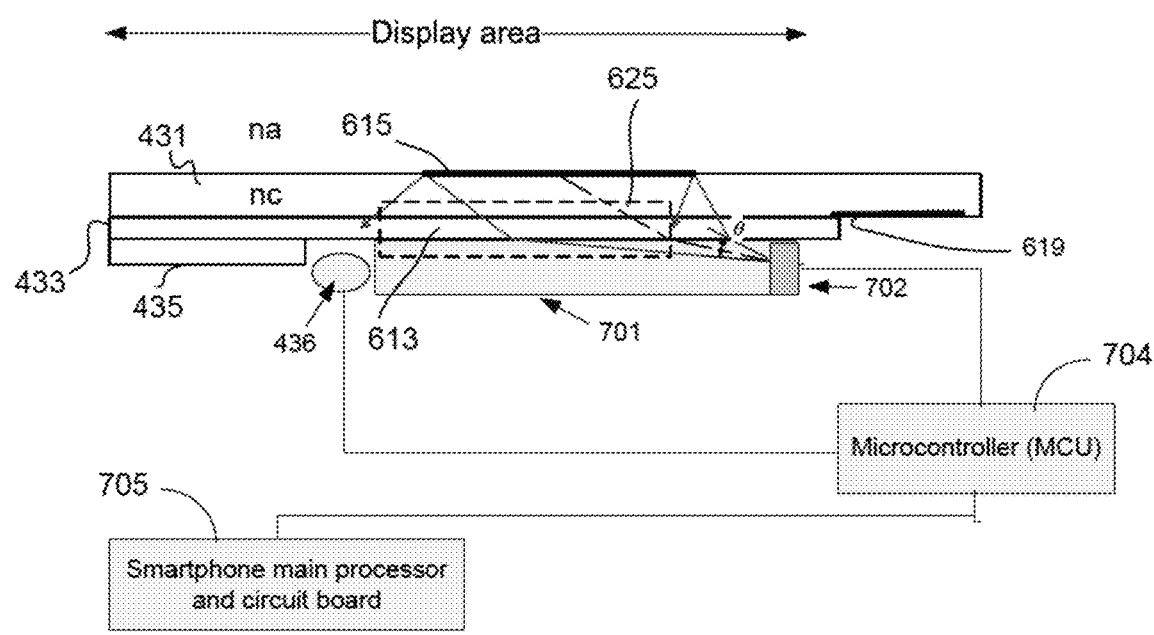

FIG. 4A and FIG. 4B show an example of one implementation of an optical sensor module under the display screen assembly for implementing the design in FIGS. 3B and 3C. The device in FIGS. 4A-4B includes a display assembly 423 with a top transparent layer 431 formed over the device screen assembly 423 as an interface for being touched by a user for the touch sensing operations and for transmitting the light from the display structure to display images to a user. This top transparent layer 431 can be a cover glass or a crystal material in some implementations. The device screen assembly 423 can include a LCD display module 433 under the top transparent layer 431. The LCD display layers allow partial optical transmission so light from the top surface can partially transmit through the LCD display layers to reach the under-LCD optical sensor module. For example, LCD display layers include electrodes and wiring structure optically acting as an array of holes and light scattering objects. A device circuit module 435 may be provided under the LCD display panel to control operations of the device and perform functions for the user to operate the device.

The optical sensor module 702 in this particular implementation example is placed under LCD display module 433. One or more illumination light sources, e.g., an illumination light source 436 under the LCD display module 433 or/and another one or more illumination light sources located under the top cover glass 431 with a color coating 619 at a peripheral region outside the LCD display module 433, are provided for providing the illumination light or probe light for the optical sensing by the optical sensor module 702 and can be controlled to emit light to at least partially pass through the LCD display module 433 to illuminate the fingerprint sensing zone 615 on the top transparent layer 431 within the device screen area for a user to place a finger therein for fingerprint identification. The illumination light from the one or more illumination light sources 436 can be directed to the fingerprint sensing area 615 on the top surface as if such illumination light is from a fingerprint illumination light zone 613. Another one or more illumination light sources located under the top cover glass 431 may be placed adjacent to the fingerprint sensing area 615 on the top surface to direct produced illumination light to reach the top cover glass 433 without passing through the LCD display module 433. As illustrated, a finger 445 is placed in the illuminated fingerprint sensing zone 615 as the effective sensing zone for fingerprint sensing. A portion of the reflected or scattered light in the zone 615 is directed into the optical sensor module underneath the LCD display module 433 and a photodetector sensing array inside the optical sensor module receives such light and captures the fingerprint pattern information carried by the received light.

In this design of using one or more illumination light sources (e.g., 436) to provide the illumination light for optical fingerprint sensing, each illumination light source 436 maybe controlled in some implementations to turn on intermittently with a relatively low cycle to reduce the power used for the optical sensing operations. The fingerprint sensing operation can be implemented in a 2-step process in some implementations: first, the one or more illumination light sources 436 are turned on in a flashing mode without turning on the LCD display panel to use the flashing light to sense whether a finger touches the sensing zone 615 and, once a touch in the zone 615 is detected, the optical sensing module is operated to perform the fingerprint sensing based on optical sensing and the LCD display panel may be turned on.

In the example in FIG. 4B, the under-screen optical sensor module includes a transparent block 701 that is coupled to the display panel to receive the returned light from the top surface of the device assembly, and an optical imaging block 702 that performs the optical imaging and imaging capturing. Light from the illumination light source 436, after reaching the cover top surface, e.g., the cover top surface at the sensing area 615 where a user finger touches, is reflected or scattered back from the cover top surface. When fingerprint ridges in close contact of the cover top surface in the sensing area 615, the light reflection under the fingerprint ridges is different, due to the presence of the skin or tissue of the finger in contact at that location, from the light reflection at another location under the fingerprint valley, where the skin or tissue of the finger is absent. This difference in light reflection conditions at the locations of the ridges and valleys in the touched finger area on the cover top surface forms an image representing an image or spatial distribution of the ridges and valleys of the touched section of the finger. The reflection light is directed back towards the LCD display module 433, and, after passing through the small holes of the LCD display module 433, reaches the interface with the low index optically transparent block 701 of the optical sensor module. The low index optically transparent block 701 is constructed to have a refractive index less than a refractive index of the LCD display panel so that the returned light can be extracted out of the LCD display panel into the optically transparent block 701. Once the returned light is received inside the optically transparent block 701, such received light enters the optical imaging unit as part of the imaging sensing block 702 and is imaged onto the photodetector sensing array or optical sensing array inside the block 702. The light reflection differences between fingerprint ridges and valleys create the contrast of the fingerprint image. As shown in FIG. 4B, a control circuit 704 (e.g., a microcontroller or MCU) is coupled to the imaging sensing block 702 and to other circuitry such as the device main processor 705 on a main circuit board.

In this particular example, the optical light path design is such the light ray enters the cover top surface within the total reflect angles on the top surface between the substrate and air interface will get collected most effectively by the imaging optics and imaging sensor array in the block 702. In this design the image of the fingerprint ridge/valley area exhibits a maximum contrast. Such an imaging system may have undesired optical distortions that would adversely affect the fingerprint sensing. Accordingly, the acquired image may be further corrected by a distortion correction during the imaging reconstruction in processing the output signals of the optical detector array in the block 702 based on the optical distortion profile along the light paths of the returned light at the optical detector array. The distortion correction coefficients can be generated by images captured at each photodetector pixel by scanning a test image pattern one line pixel at a time, through the whole sensing area in both X direction lines and Y direction lines. This correction process can also use images from tuning each individual pixel on one at a time, and scanning through the whole image area of the photodetector array. This correction coefficients only need to be generated one time after assembly of the sensor.

The background light from environment (e.g., sun light or room light) may enter the image sensor through the LCD panel top surface, through holes in the LCD display assembly 433. Such background light can create a background baseline in the interested images from fingers and is undesirable. Different methods can be used to reduce this baseline intensity. One example is to tune on and off the illumination light source 436 at a certain frequency f and the image sensor accordingly acquires the received images at the same frequency by phase synchronizing the light source driving pulse and image sensor frame. Under this operation, only one of the image phases contain light from the light source. By subtracting even and odd frames, it is possible to obtain an image which most consists of light emitted from the modulated illumination light source. Based on this design, each display scan frame generates a frame of fingerprint signals. If two sequential frames of signals by turning on the illumination light in one frame and off in the other frame are subtracted, the ambient background light influence can be minimized or substantially eliminated. In implementations, the fingerprint sensing frame rate can be one half of the display frame rate.

A portion of the light from the illumination light source 436 may also go through the cover top surface and enter the finger tissues. This part of light power is scattered around and a part of this scattered light may be eventually collected by the imaging sensor array in the optical sensor module. The light intensity of this scattered light depends on the finger's skin color, the blood concentration in the finger tissue and this information carried by this scattered light on the finger is useful for fingerprint sensing and can be detected as part of the fingerprint sensing operation. For example, by integrating the intensity of a region of user's finger image, it is possible to observe the blood concentration increase/decrease depends on the phase of the user's heart-beat. This signature can be used to determine the user's heart beat rate, to determine if the user's finger is a live finger, or to provide a spoof device with a fabricated fingerprint pattern.

The one or more illumination light sources 436 in FIG. 4B can be designed to emit light of different colors or wavelengths and the optical sensor module can capture returned light from a person's finger at the different colors or wavelengths. By recording the corresponding measured intensity of the returned light at the different colors or wavelengths, information associated with the user's skin color can be determined. As an example, when a user registers a finger for fingerprint authentication operation, the optical fingerprint sensor also measures intensity of the scatter light from finger at color A, and B, as intensity Ia, Ib. The ratio of Ia/Ib could be recorded to compare with later measurement when user's finger is placed on the sensing area to measure fingerprint. This method can help reject the spoof device which may not match user's skin color.

The one or more illumination light sources 436 can be controlled by the same electronics 704 (e.g., MCU) for controlling the image sensor array in the block 702. The one or more illumination light sources 436 can be pulsed for a short time, at a low duty cycle, to emit light intermittently and to provide pulse light for image sensing. The image sensor array can be operated to monitor the light pattern at the same pulse duty cycle. If there is a human finger touching the sensing area 615 on the screen, the image that is captured at the imaging sensing array in the block 702 can be used to detect the touching event. The control electronics or MCU 704 connected to the image sensor array in the block 702 can be operated to determine if the touch is by a human finger touch. If it is confirmed that it is a human finger touch event, the MCU 704 can be operated to wake up the smartphone system, turn on the illumination light source 436 for performing the optical fingerprint sensing), and use the normal mode to acquire a full fingerprint image. The image sensor array in the block 702 will send the acquired fingerprint image to the smartphone main processor 705 which can be operated to match the captured fingerprint image to the registered fingerprint database. If there is a match, the smartphone will unlock the phone, and start the normal operation. If the captured image is not matched, the smartphone will feedback to user that the authentication is failed. User may try again, or input passcode.

In the example in FIGS. 4A and 4B, the under-screen optical sensor module uses the optically transparent block 701 and the imaging sensing block 702 with the photodetector sensing array to optically image the fingerprint pattern of a touching finger in contact with the top surface of the display screen onto the photodetector sensing array. The optical imaging axis or detection axis 625 from the sensing zone 615 to the photodetector array in the block 702 is illustrated in FIG. 4B. The optically transparent block 701 and the front end of the imaging sensing block 702 before the photodetector sensing array forma a bulk imaging module to achieve proper imaging for the optical fingerprint sensing. Due to the optical distortions in this imaging process, a distortion correction can be used, as explained above, to achieve the desired imaging operation.

Figure 5A:
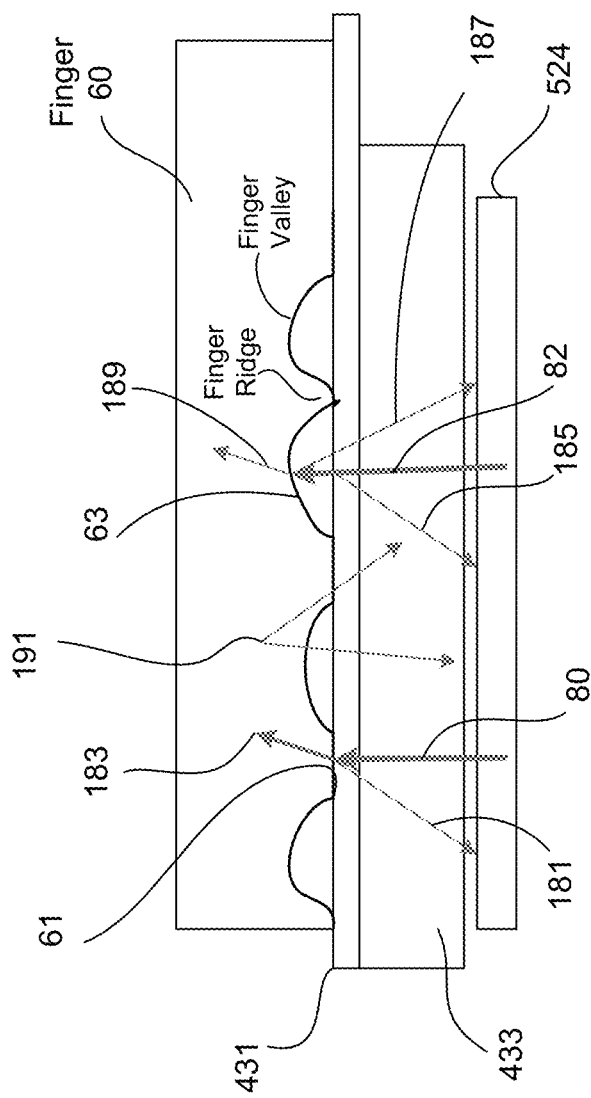
FIGS. 5A, 5B and 5C illustrate signal generation for the returned light from the sensing zone on the top sensing surface under two different optical conditions to facilitate the understanding of the operation of the under-screen optical sensor module.
Figure 5B:
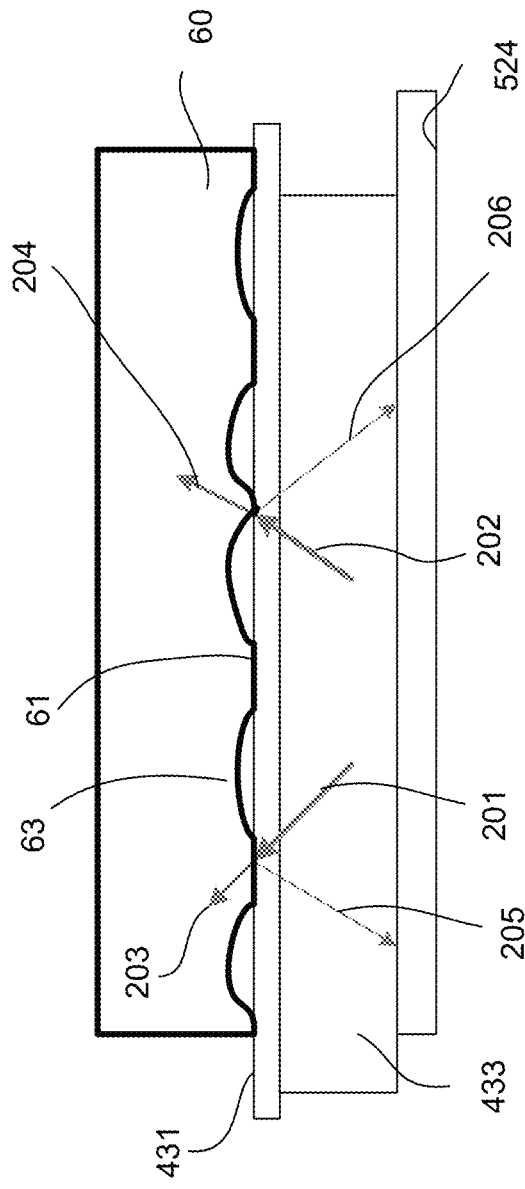
Figure 5C:
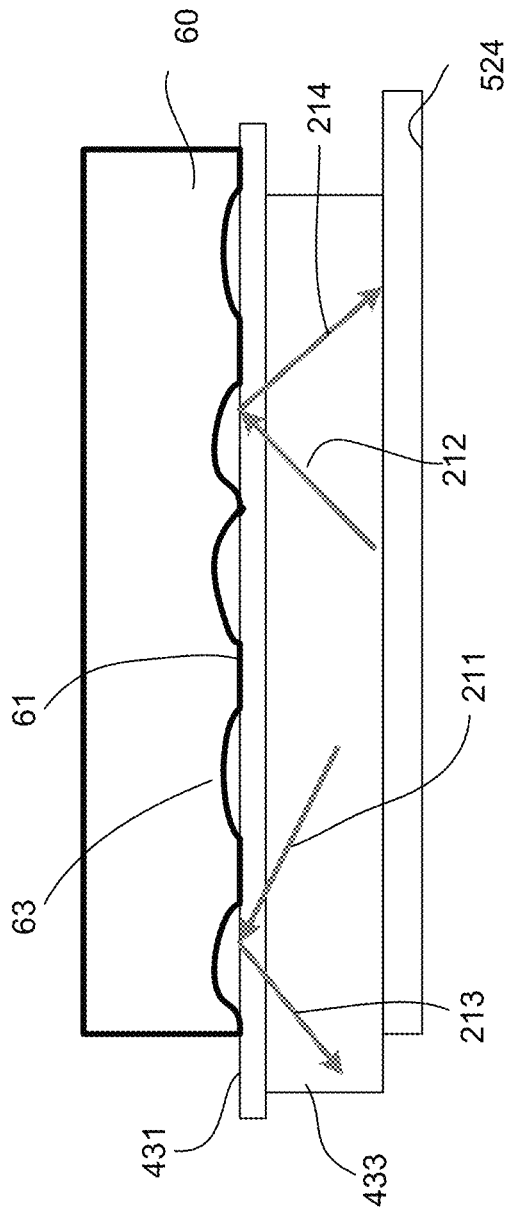

In the optical sensing by the under-screen optical sensor module in FIGS. 4A and 4B and other designs disclosed herein, the optical signal from the sensing zone 615 on the top transparent layer 431 to the under-screen optical sensor module include different light components. FIGS. 5A, 5B and 5C illustrate signal generation for the returned light from the sensing zone 615 under different optical conditions to facilitate the understanding of the operation of the under-screen optical sensor module.

FIG. 5A shows an example of how illumination light from the illumination light source 436 propagates through the OLED display module 433, after transmitting through the top transparent layer 431, and generates different returned light signals including light signals that carry fingerprint pattern information to the under-screen optical sensor module. For simplicity, two illumination rays 80 and 82 at two different locations are directed to the top transparent layer 431 without experiencing total reflection at the interfaces of the top transparent layer 431. Specifically, the illumination light rays 80 and 82 are perpendicular or nearly perpendicular to the top layer 431. A finger 60 is in contact with the sensing zone 615 on the e top transparent layer 431. As illustrated, the illumination light beam 80 reaches to a finger ridge in contact with the top transparent layer 431 after transmitting through the top transparent layer 431 to generate the light beam 183 in the finger tissue and another light beam 181 back towards the LCD display module 433. The illumination light beam 82 reaches to a finger valley located above the top transparent layer 431 after transmitting through the top transparent layer 431 to generate the reflected light beam 185 from the interface with the top transparent layer 431 back towards the LCD display module 433, a second light beam 189 that enters the finger tissue and a third light beam 187 reflected by the finger valley.

In the example in FIG. 5A, it is assumed that the finger skin's equivalent index of refraction is about 1.44 at 550 nm and the cover glass index of refraction is about 1.51 for the top transparent layer 431. The finger ridge-cover glass interface reflects part of the beam 80 as reflected light 181 to bottom layers 524 below the LCD display module 433. The reflectance can be low, e.g., about 0.1% in some LCD panels. The majority of the light beam 80 becomes the beam 183 that transmits into the finger tissue 60 which causes scattering of the light 183 to produce the returned scattered light 191 towards the LCD display module 433 and the bottom layers 524. The scattering of the transmitted light beam 189 from the LCD pixel 73 in the finger tissue also contributes to the returned scattered light 191.

The beam 82 at the finger skin valley location 63 is reflected by the cover glass surface (e.g., about 3.5% as the reflected light 185 towards bottom layers 524, and the finger valley surface reflects about 3.3% of the incident light power (light 187) to bottom layers 524. The total reflection may be about 6.8%. The majority light 189 is transmitted into the finger tissues 60. Part of the light power in the transmitted light 189 in the figure tissue is scattered by the tissue to contribute to the scattered light 191 towards and into the bottom layers 524.

Therefore, the light reflections from various interface or surfaces at finger valleys and finger ridges of a touching finger are different and the reflection ratio difference carries the fingerprint map information and can be measured to extract the fingerprint pattern of the portion that is in contact with the top transparent layer 431 and is illuminated the OLED light.

FIGS. 5B and 5C illustrate optical paths of two additional types of illumination light rays at the top surface under different conditions and at different positions relative to valleys or ridges of a finger, including under a total reflection condition at the interface with the top transparent layer 431. The illustrated illumination light rays generate different returned light signals including light signals that carry fingerprint pattern information to the under-screen optical sensor module. It is assumed that the cover glass 431 and the LCD display module 433 are glued together without any air gap in between so that illumination light with a large incident angle to the cover glass 431 will be totally reflected at the cover glass-air interface. FIGS. 5A, 5B and 5C illustrate examples of three different groups divergent light beams: (1) central beams 82 with small incident angles to the cover glass 431 without the total reflection (FIG. 5A), (2) high contrast beams 201, 202, 211, 212 that are totally reflected at the cover glass 431 when nothing touches the cover glass surface and can be coupled into finger tissues when a finger touches the cover glass 431 (FIGS. 5B and 5C), and (3) escaping beams having very large incident angles that are totally reflected at the cover glass 431 even at a location where the finger issue is in contact.

For the central light beams 82, the cover glass surface reflects about 0.1%~3.5% to light beam 185 that is transmitted into bottom layers 524, the finger skin reflects about 0.1%~3.3% to light beam 187 that is also transmitted into bottom layers 524. The reflection difference is dependent on whether the light beams 82 meet with finger skin ridge 61 or valley 63. The rest light beam 189 is coupled into the finger tissues 60.

For high contrast light beams 201 and 202, the cover glass surface reflects nearly 100% to light beams 205 and 206 respectively if nothing touches the cover glass surface. When the finger skin ridges touch the cover glass surface and at light beams 201 and 202 positions, most of the light power is coupled into the finger tissues 60 by light beams 203 and 204.

For high contrast light beams 211 and 212, the cover glass surface reflects nearly 100% to light beams 213 and 214 respectively if nothing touches the cover glass surface. When the finger touches the cover glass surface and the finger skin valleys happen to be at light beams 211 and 212 positions, no light power is coupled into finger tissues 60.

As illustrated in FIG. 5A, light beams that are coupled into finger tissues 60 will experience random scattering by the figure tissues to form low-contrast light 191 and part of such low-contrast light 191 will pass through the LCD display module 433 to reach to the optical sensor module.

Therefore, in high contrast light beams illuminated area, finger skin ridges and valleys cause different optical reflections and the reflection difference pattern carries the fingerprint pattern information. The high contrast fingerprint signals can be achieved by comparing the difference.

The disclosed under-screen optical sensing technology can be in various configurations to optically capture fingerprints based on the design in FIGS. 3B and 3C.

For example, the specific implementation in FIG. 4B based on optical imaging by using a bulk imaging module in the optical sensing module can be implemented in various configurations. FIGS. 6A-6C, 7, 8A-8B, 9, 10A-10B, 11 and 12 illustrate examples of various implementations and additional features and operations of the under-screen optical sensor module designs for optical fingerprint sensing.

Figure 6A:
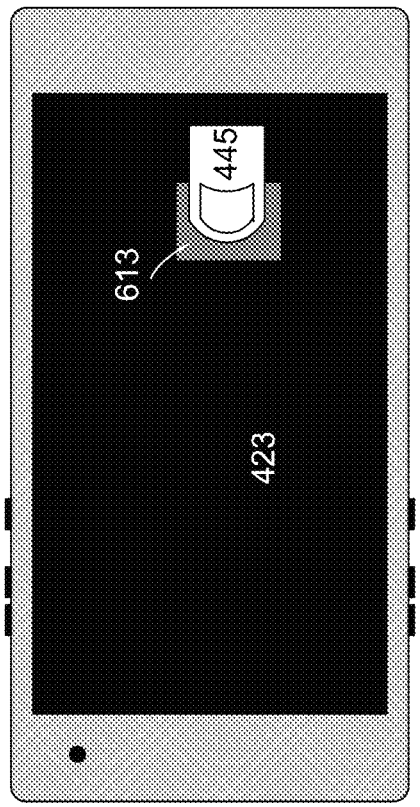

FIG. 6A, FIG. 6B and FIG. 6C show an example of a under-screen optical sensor module based on optical imaging via a lens for capturing a fingerprint from a finger 445 pressing on the display cover glass 423. FIG. 6C is an enlarged view of the optical sensor module part shown in FIG. 6B. The under-screen optical sensor module as shown in FIG. 6B is placed under the LCD display module 433 includes an optically transparent spacer 617 that is engaged to the bottom surface of the LCD display module 433 to receive the returned light from the sensing zone 615 on the top surface of the top transparent layer 431, an imaging lens 621 that is located between and spacer 617 and the photodetector array 623 to image the received returned light from the sensing zone 615 onto the photodetector array 623. Like the imaging system in the example in FIG. 4B, this imaging system in FIG. 6B for the optical sensor module can experience image distortions and a suitable optical correction calibration can be used to reduce such distortions, e.g., the distortion correction methods described for the system in FIG. 4B.

Similar to the assumptions in FIGS. 5A, 5B and 5C, it is assumed that the finger skin's equivalent index of refraction to be about 1.44 at 550 nm and a bare cover glass index of refraction to be about 1.51 for the cover glass 423. When the OLED display module 433 is glued onto the cover glass 431 without any air gap, the total inner reflection happens in large angles at or larger than the critical incident angle for the interface. The total reflection incident angle is about 41.8° if nothing is in contact with the cover glass top surface, and the total reflection angle is about 73.7° if the finger skin touches the cover glass top surface. The corresponding total reflection angle difference is about 31.9°.

In this design, the micro lens 621 and the photodiode array 623 define a viewing angle θ for capturing the image of a contact finger in the sensing zone 615. This viewing angle can be aligned properly by controlling the physical parameters or configurations in order to detect a desired part of the cover glass surface in the sensing zone 615. For example, the viewing angle may be aligned to detect the total inner reflection of the LCD display assembly. Specifically, the viewing angle θ is aligned to sense the effective sensing zone 615 on the cover glass surface. The effective sensing cover glass surface 615 may be viewed as a mirror so that the photodetector array effectively detects an image of the fingerprint illumination light zone 613 in the LCD display that is projected by the sensing cover glass surface 615 onto the photodetector array. The photodiode/photodetector array 623 can receive the image of the zone 613 that is reflected by the sensing cover glass surface 615. When a finger touches the sensing zone 615, some of the light can be coupled into the fingerprint's ridges and this will cause the photodetector array to receive light from the location of the ridges to appear as a darker image of the fingerprint. Because the geometrics of the optical detection path are known, the fingerprint image distortion caused in the optical path in the optical sensor module can be corrected.

Consider, as a specific example, that the distance H in FIG. 6B from the detection module central axis to the cover glass top surface is 2 mm. This design can directly cover 5 mm of an effective sensing zone 615 with a width Wc on the cover glass. Adjusting the spacer 617 thickness can adjust the detector position parameter H, and the effective sensing zone width Wc can be optimized. Because H includes the thickness of the cover glass 431 and the display module 433, the application design should take these layers into account. The spacer 617, the micro lens 621, and the photodiode array 623 can be integrated under the color coating 619 on the bottom surface of the top transparent layer 431.

Figure 7:
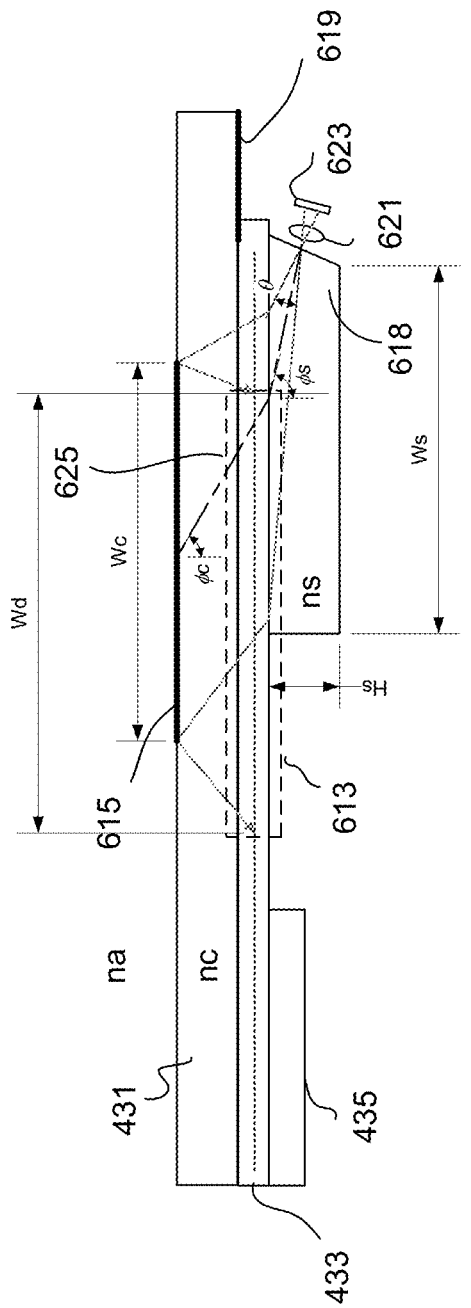

FIG. 7 shows an example of further design considerations of the optical imaging design for the optical sensor module shown in FIGS. 6A-6C by using a special spacer 618 to replace the spacer 617 in FIGS. 6B-6C to increase the size of the sensing area 615. The spacer 618 is designed with a width Ws and thickness is Hs to have a low refraction index (RI) ns, and is placed under the LCD display module 433, e.g., being attached (e.g., glued) to the bottom surface the LCD display module 433. The end facet of the spacer 618 is an angled or slanted facet that interfaces with the micro lens 621. This relative position of the spacer and the lens is different from FIGS. 6B-6C where the lens is placed underneath the spacer 617. The micro lens 621 and a photodiode array 623 are assembled into the optical detection module with a detection angle width θ. The detection axis 625 is bent due to optical refraction at the interface between the spacer 618 and display module 433 and at the interface between the cover glass 431 and the air. The local incident angle φ1 and φ2 are decided by the refractive indices RIs, ns, nc, and na of the materials for the components.

If nc is greater than ns, φ1 is greater than φ2. Thus, the refraction enlarges the sensing width Wc. For example, assuming the finger skin's equivalent RI is about 1.44 at 550 nm and the cover glass index RI is about 1.51, the total reflection incident angle is estimated to be about 41.8° if nothing touches the cover glass top surface, and the total reflection angle is about 73.7° if the finger skin touches the cover glass top surface. The corresponding total reflection angle difference is about 31.9°. If the spacer 618 is made of same material of the cover glass, and the distance from the detection module center to the cover glass top surface is 2 mm, if detection angle width is θ=31.9°, the effective sensing area width Wc is about 5 mm. The corresponding central axis's local incident angle is φ1=φ2=57.75°. If the material for the special spacer 618 has a refractive index ns about 1.4, and Hs is 1.2 mm and the detection module is tilted at φ1=70°. The effective sensing area width is increased to be greater than 6.5 mm. Under those parameters, the detection angle width in the cover glass is reduced to 19°. Therefore, the imaging system for the optical sensor module can be designed to desirably enlarge the size of the sensing area 615 on the top transparent layer 431.

When the RI of the special spacer 618 is designed to be sufficiently low (e.g., to use MgF2, CaF2, or even air to form the spacer), the width Wc of the effective sensing area 615 is no longer limited by the thickness of the cover glass 431 and the display module 433. This property provides desired design flexibility. In principle, if the detection module has a sufficient resolution, the effective sensing area may even be increased to cover the entire display screen.

Since the disclosed optical sensor technology can be used to provide a large sensing area for capturing a pattern, the disclosed under-screen optical sensor modules may be used to capture and detect not only a pattern of a finger but a larger size patter such a person's palm that is associated with a person for user authentication.

Figure 8A:
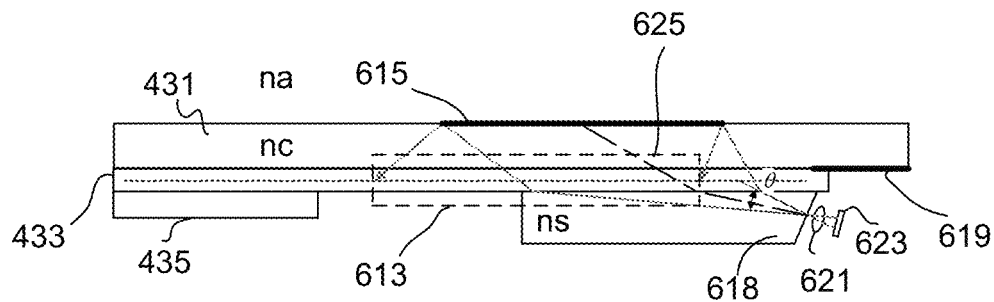
Figure 8B:
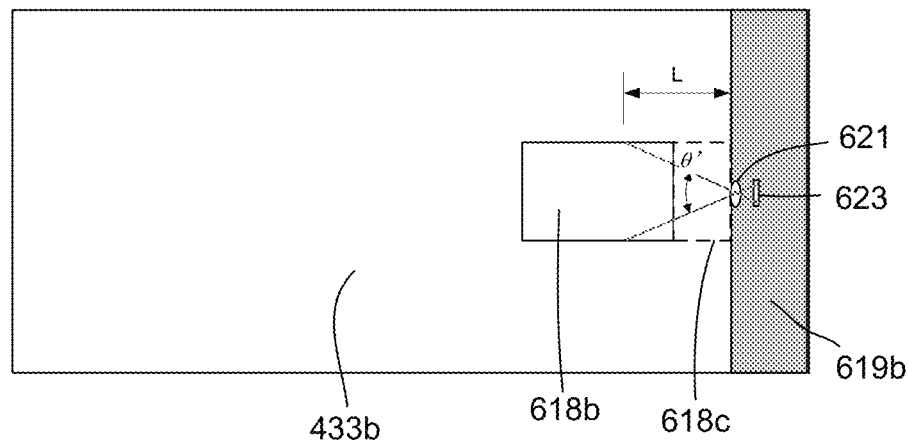

FIGS. 8A-8B show an example of further design considerations of the optical imaging design for the optical sensor module shown in FIG. 7 by setting the detection angle θ' of the photodetector array relative in the display screen surface and the distance L between the lens 621 and the spacer 618. FIG. 8A shows a cross-sectional view along the direction perpendicular to the display screen surface and FIG. 8B shows a view of the device from either the bottom or top of the displace screen. A filling material 618c can be used to fill the space between the lens 621 and the photodetector array 623. For example, the filling material 618c can be same material of the special spacer 618 or another different material. In some designs, the filling material 618c may be the air space.

Figure 9:
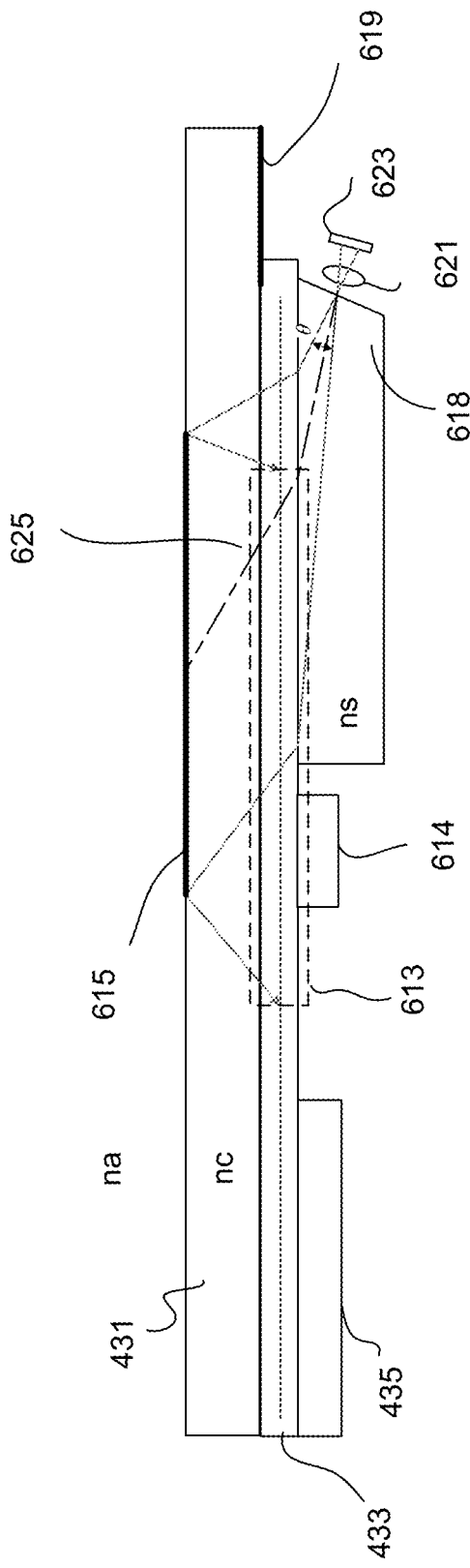

FIG. 9 shows another example of an under-screen optical sensor module based on the design in FIG. 7 where one or more illumination light sources 61 are provided to illuminate the top surface sensing zone 615 for optical fingerprint sensing. The illumination light sources 614 may be of an expanded type, or be a collimated type so that all the points within the effective sensing zone 615 is illuminated. The illumination light sources 614 may be a single element light source or an array of light sources.

Figure 10A:
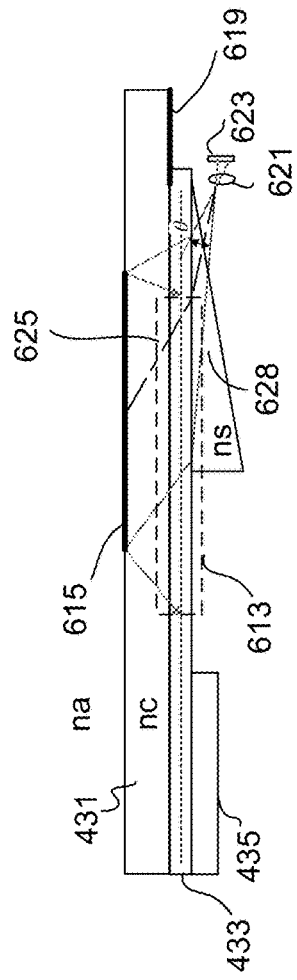
Figure 10B:
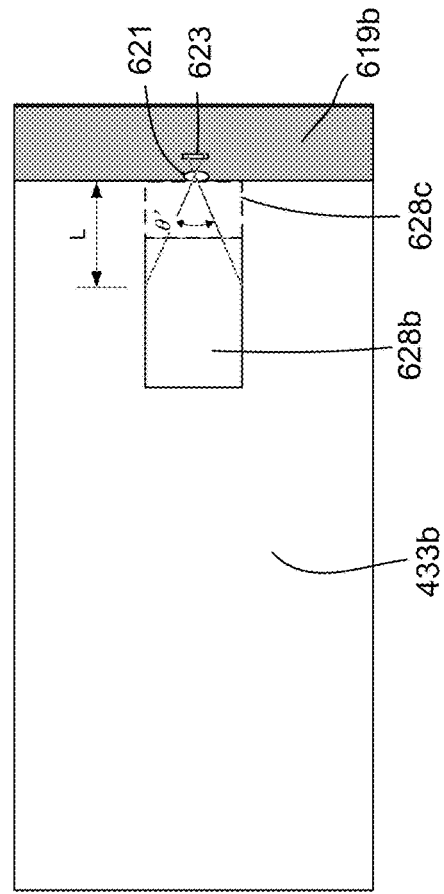

FIGS. 10A-10B show an example of an under-screen optical sensor module that uses an optical coupler 628 shaped as a thin wedge to improve the optical detection at the optical detector array 623. FIG. 10A shows a cross section of the device structure with an under-screen optical sensor module for fingerprint sensing and FIG. 10B shows a top view of the device screen. The optical wedge 628 (with a refractive index $n_s$) is located below the display panel structure to modify a total reflection condition on a bottom surface of the display panel structure that interfaces with the optical wedge 628 to permit extraction of light out of the display panel structure through the bottom surface. The optical detector array 623 receives the light from the optical wedge 628 extracted from the display panel structure and the optical imaging module 621 is located between the optical wedge 628 and the optical detector array 623 to image the light from the optical wedge 628 onto the optical detector array 623. In the illustrated example, the optical wedge 628 includes a slanted optical wedge surface facing the optical imaging module and the optical sensing array 623. Also, as shown, there is a free space between the optical wedge 628 and the optical imaging module 621.

If the light is totally reflected at the sensing surface of the cover glass 431, the reflectance is 100%, of the highest efficiency. However, the light will also be totally reflected at the LCD bottom surface 433b if it is parallel to the cover glass surfaces. The wedge coupler 628 is used to modify the local surface angle so that the light can be coupled out for the detection at the optical detector array 623. The micro holes in the LCD display module 433 provide the desired light propagation path for light to transmit through the LCD display module 433 for the under-screen optical sensing. The actual light transmission efficiency may gradually be reduced if the light transmission angle becomes too large or when the TFT layer becomes too thick. When the angle is close to the total reflection angle, namely about 41.8° when the cover glass refractive index is 1.5, the fingerprint image looks good. Accordingly, the wedge angle of the wedge coupler 628 may be adjusted to be of a couple of degrees so that the detection efficiency can be increased or optimized. If the cover glass' refractive index is selected to be higher, the total reflection angle becomes smaller. For example, if the cover glass is made of Sapphire which refractive index is about 1,76, the total reflection angle is about 34.62°. The detection light transmission efficiency in the display is also improved. Therefore, this design of using a thin wedge to set the detection angle to be higher than the total reflection angle, and/or to use high refractive index cover glass material to improve the detection efficiency.

In the under-screen optical sensor module designs in FIGS. 6A-10B, the sensing area 615 on the top transparent surface is not vertical or perpendicular to the detection axis 625 of the optical sensor module so that the image plane of the sensing area is also not vertical or perpendicular to the detection axis 625. Accordingly, the plane of the photodetector array 523 can be tilted relative the detection axis 625 to achieve high quality imaging at the photodetector array 623.

Figure 11:
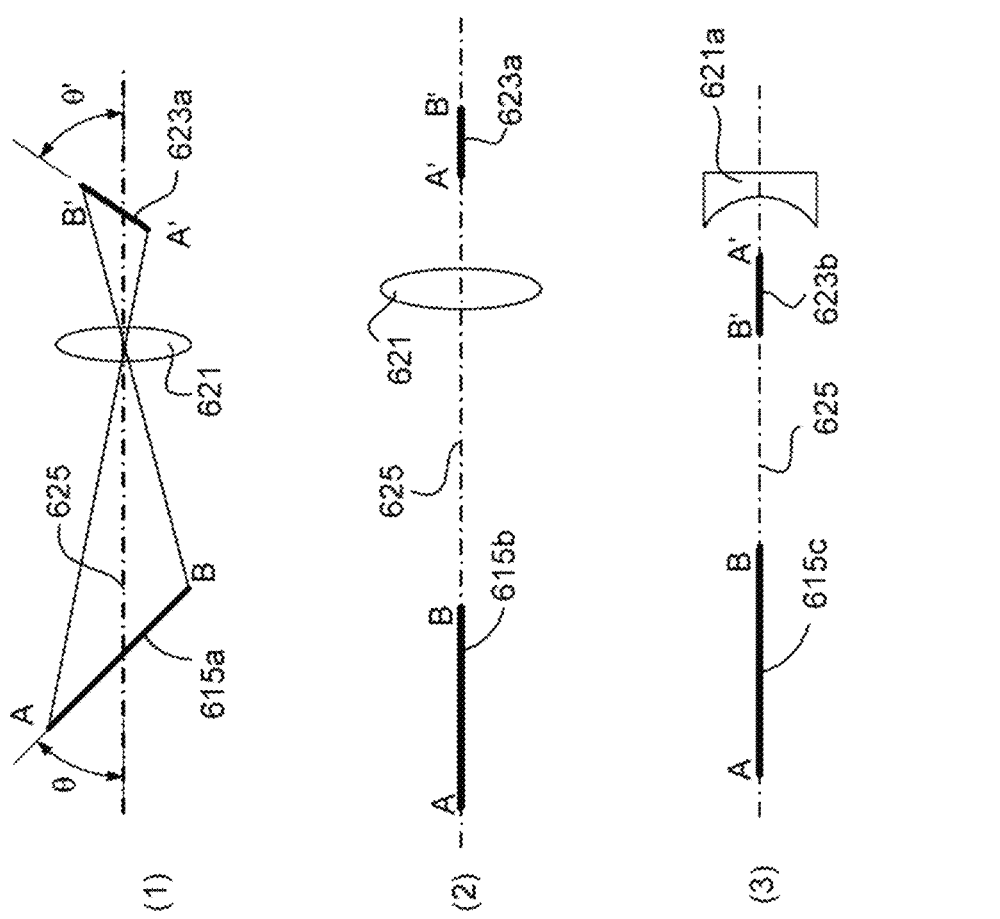
FIG. 11 shows imaging of the fingerprint sensing area on the top transparent layer via an imaging module under different tiling conditions where an imaging device images the fingerprint sensing area onto an optical detector array and the imaging device may be optically transmissive or optically reflective.

FIG. 11 shows three example configurations for this tiling. FIG. 11 (1) shows the sensing area 615a is tilted and is not perpendicular the detection axis 625 where the image 623a of the sensing area 615a by the lens 621 is a tilted image 623a. In a specified case shown in (2), the sensing area 615b is aligned to be on the detection axis 625, its image plane 623a on the other side of the lens 621 will also be located on the detection axis 625. In practice, the lens 621 can be partially cut off so as to simplify the package. In various implementations, the micro lens 621 can also be of transmission type or reflection type. For example, a specified approach is illustrated in FIG. 11 (3). The sensing area 615c is imaged as the image 623b by an imaging mirror 621a. A photodiode array 623b is aligned to detect the signals.

In the above designs where the lens 621 is used, the lens 621 can be designed to have an effective aperture that is larger than the aperture of the holes in the LCD display layers that allow transmission of light through the LCD display module for optical fingerprint sensing. This design can reduce the undesired influence of the wiring structures and other scattering objects in the LCD display module.

Figure 12:
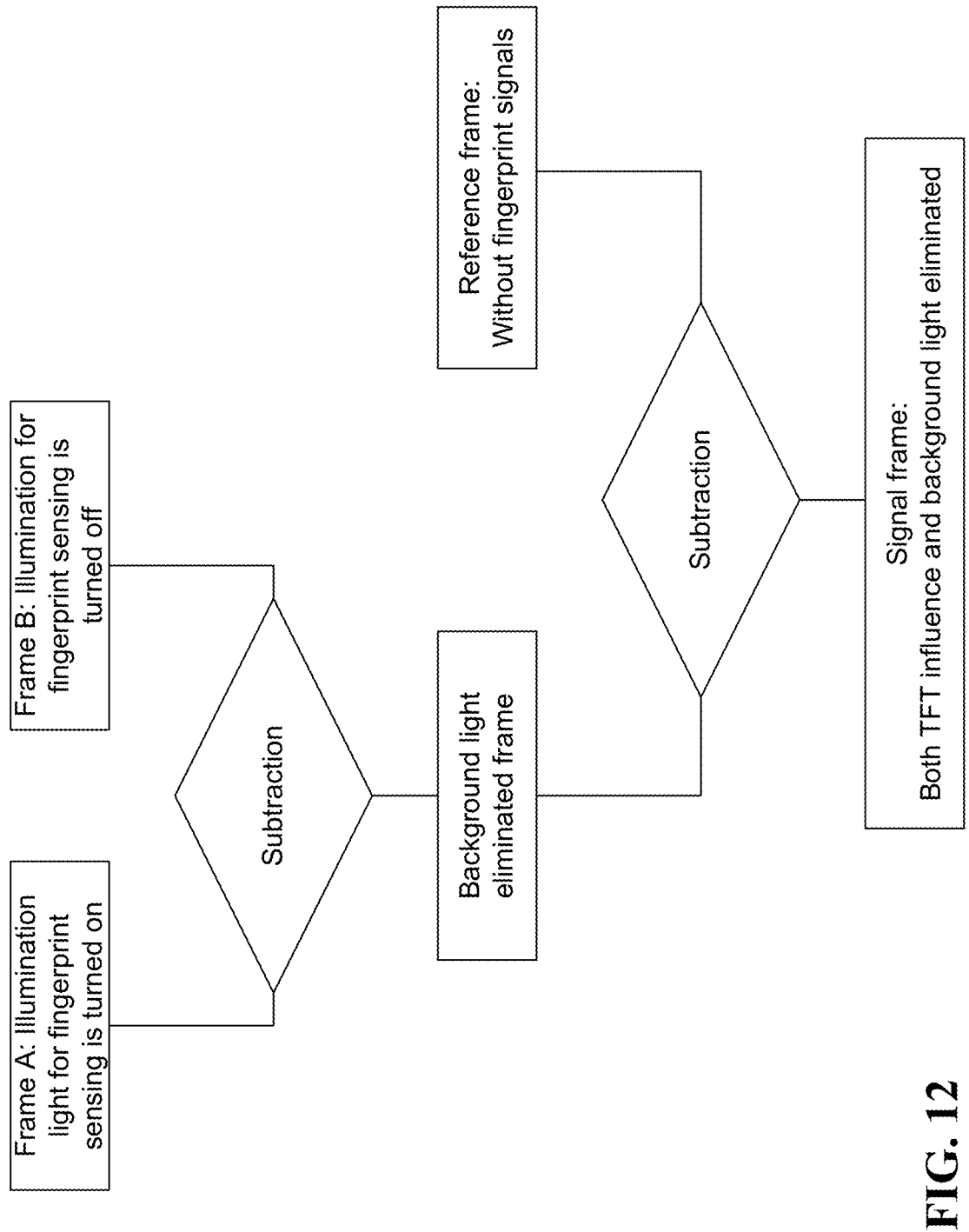
FIG. 12 shows an example of an operation of the fingerprint sensor for reducing or eliminating undesired contributions from the background light in fingerprint sensing.

FIG. 12 shows an example of an operation of the fingerprint sensor for reducing or eliminating undesired contributions from the background light in fingerprint sensing. The optical detector array can be used to capture various frames and the captured frames can be used to perform differential and averaging operations among multiple frames to reduce the influence of the background light. For example, in frame A, the illumination light source for optical fingerprint sensing is turned on to illuminate the finger touching area, in frame B the illumination is changed or turned off. Subtraction of the signals of frame B from the signals of frame A can be used in the image processing to reduce the undesired background light influence.

The undesired background light in the fingerprint sensing may also be reduced by providing proper optical filtering in the light path. One or more optical filters may be used to reject the environment light wavelengths, such as near IR and partial of the red light etc. In some implementation, such optical filter coatings may be made on the surfaces of the optical parts, including the display bottom surface, prism surfaces, sensor surface etc. For example, human fingers absorb most of the energy of the wavelengths under ~580 nm, if one or more optical filters or optical filtering coatings can be designed to reject light in wavelengths from 580 nm to infrared, undesired contributions to the optical detection in fingerprint sensing from the environment light may be greatly reduced.

Figure 13:
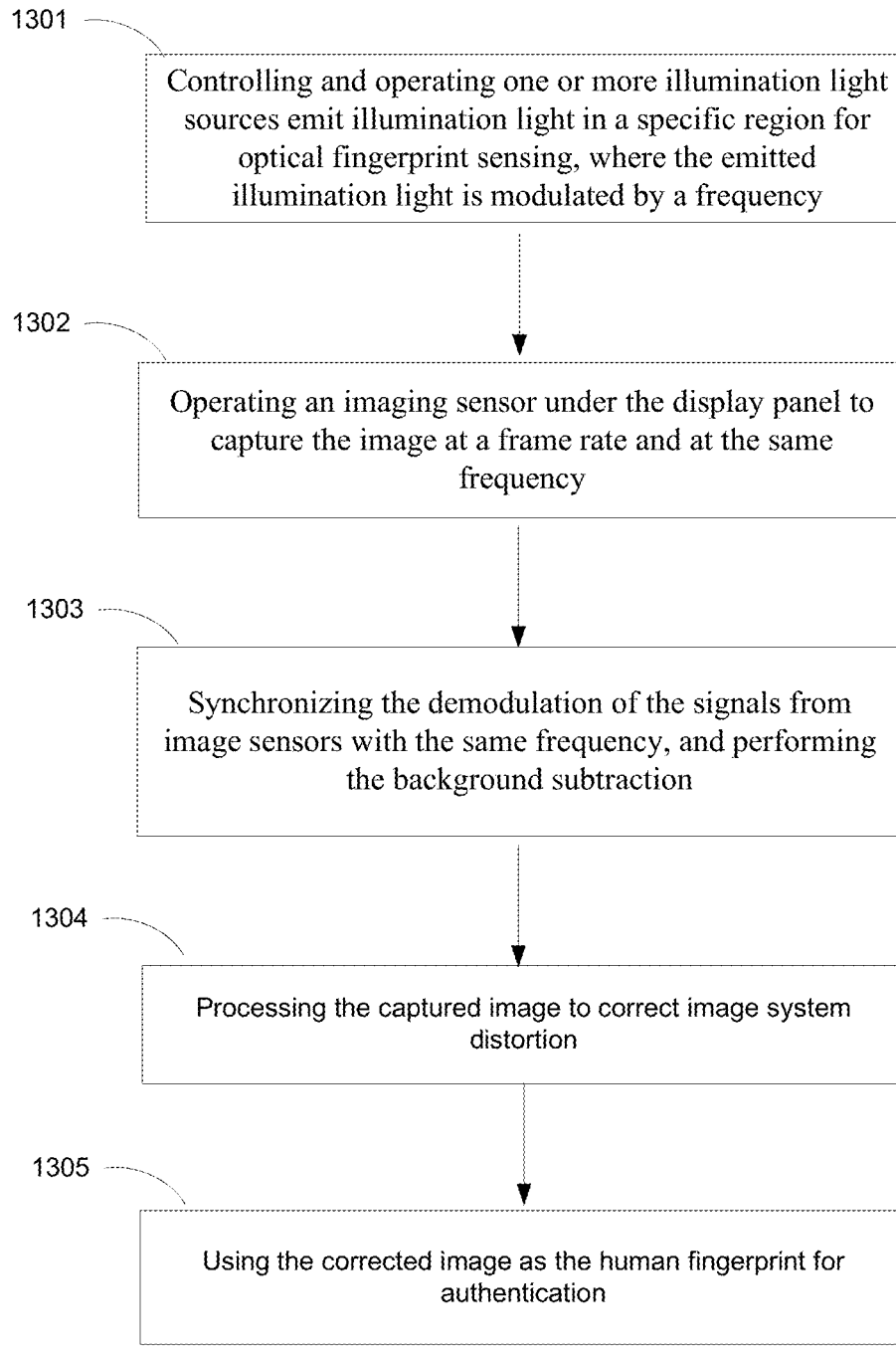
FIG. 13 shows a process for operating an under-screen optical sensor module for capturing a fingerprint pattern.

FIG. 13 shows an example of an operation process for correcting the image distortion in the optical sensor module. At step 1301, the one or more illumination light sources are controlled and operated to emit light in a specific region, and the light emission of such pixels is modulated by a frequency F. Ate step 1302, an imaging sensor under the display panel is operated to capture the image at frame rate at same frequency F. In the optical fingerprint sensing operation, a finger is placed on top of the display panel cover substrate and the presence of the finger modulates the light reflection intensity of the display panel cover substrate top surface. The imaging sensor under the display captures the fingerprint modulated reflection light pattern. At step 1303, the demodulation of the signals from image sensors is synchronized with the frequency F, and the background subtraction is performed. The resultant image has a reduced background light effect and includes images from pixel emitting lights. At step 1304, the capture image is processed and calibrated to correct image system distortions. At step 1305, the corrected image is used as a human fingerprint image for user authentication.

The same optical sensors used for capturing the fingerprint of a user can be used also to capture the scattered light from the illuminated finger as shown by the back scattered light 191 in FIG. 5A. The detector signals from the back scattered light 191 in FIG. 5A in a region of interest can be integrated to produce an intensity signal. The intensity variation of this intensity signal is evaluated to determine the heart rate of the user.

The above fingerprint sensor may be hacked by malicious individuals who can obtain the authorized user's fingerprint, and copy the stolen fingerprint pattern on a carrier object that resembles a human finger. Such unauthorized fingerprint patterns may be used on the fingerprint sensor to unlock the targeted device. Hence, a fingerprint pattern, although a unique biometric identifier, may not be by itself a completely reliable or secure identification. The under-screen optical sensor module can also be used to as an optical anti-spoofing sensor for sensing whether an input object with fingerprint patterns is a finger from a living person and for determining whether a fingerprint input is a fingerprint spoofing attack. This optical anti-spoofing sensing function can be provided without using a separate optical sensor. The optical anti-spoofing can provide high-speed responses without compromising the overall response speed of the fingerprint sensing operation.

Figure 14:
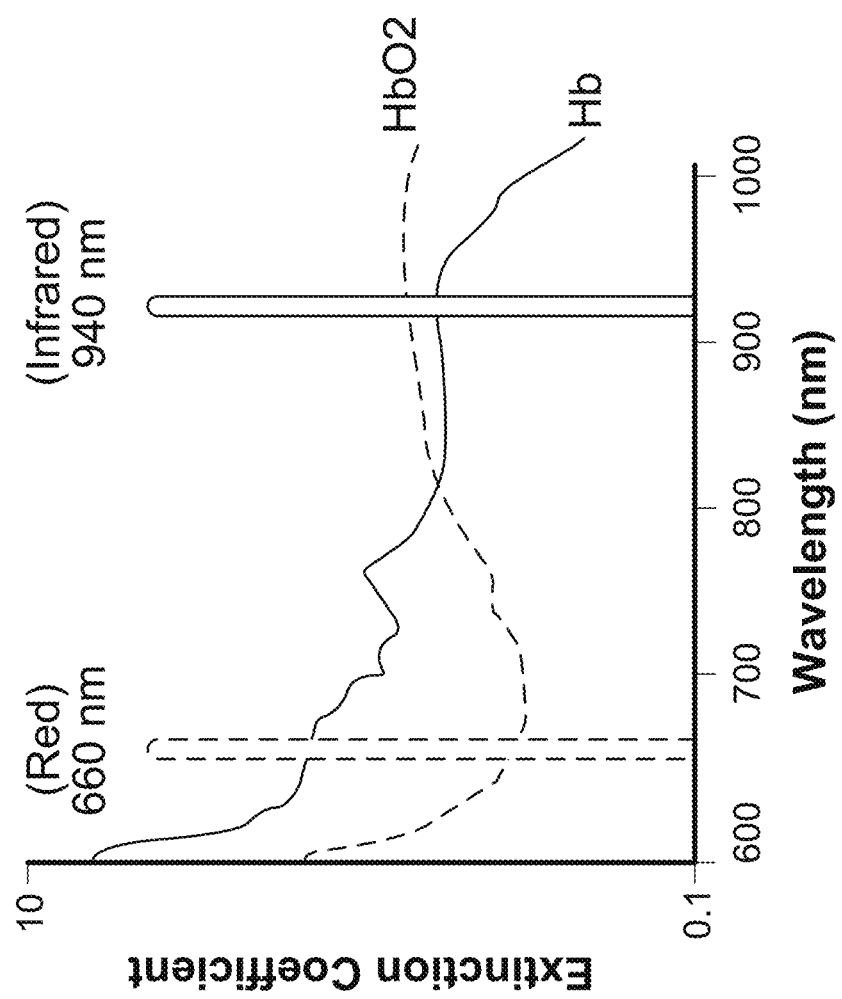
FIGS. 14, 15 and FIG. 16 show an example of an operation process for determining whether an object in contact with the LCD display screen is part of a finger of a live person by illuminating the finger with light in two different light colors.

FIG. 14 shows exemplary optical extinction coefficients of materials being monitored in blood where the optical absorptions are different between the visible spectral range e.g., red light at 660 nm and the infrared range, e.g., IR light at 940 nm. By using probe light to illuminate a finger at a first visible wavelength (Color A) and a second different wavelength such as an IR wavelength (Color B), the differences in the optical absorption of the input object can be captured determine whether the touched object is a finger from a live person. The one or more illumination light sources for providing the illumination for optical sensing can be used to emit light of different colors to emit probe or illumination light at least two different optical wavelengths to use the different optical absorption behaviors of the blood for live finger detection. When a person' heart beats, the pulse pressure pumps the blood to flow in the arteries, so the extinction ratio of the materials being monitored in the blood changes with the pulse. The received signal carries the pulse signals. These properties of the blood can be used to detect whether the monitored material is a live-fingerprint or a fake fingerprint.

Figure 15:
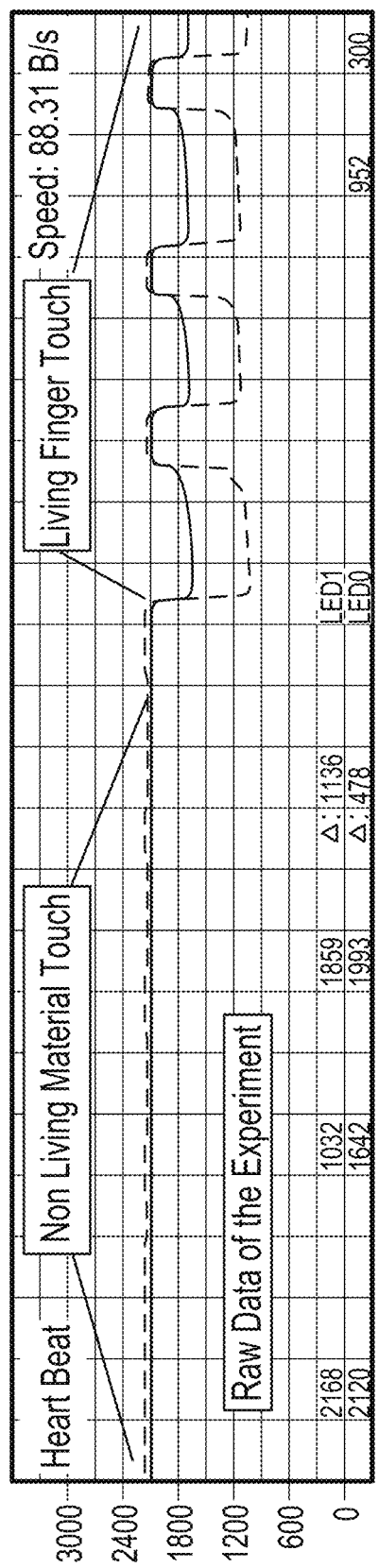

FIG. 15 shows a comparison between optical signal behaviors in the reflected light from a nonliving material (e.g., a fake finger) and a live finger. The optical fingerprint sensor can also operate as a heartbeat sensor to monitor a living organism. When two or more wavelengths of the probe light are detected, the extinction ratio difference can be used to quickly determine whether the monitored material is a living organism, such as live fingerprint. In the example shown in FIG. 15, probe light at different wavelengths were used, one at a visible wavelength and another a IR wavelength as illustrated in FIG. 14.

When a nonliving material touches the top cover glass above the fingerprint sensor module, the received signal reveals strength levels that are correlated to the surface pattern of the nonliving material and the received signal does not contain signal components associated with a finger of a living person. However, when a finger of a living person touches the top cover glass, the received signal reveals signal characteristics associated with a living person, including obviously different strength levels because the extinction ratios are different for different wavelengths. This method does not take long time to determine whether the touching material is a part of a living person. In FIG. 15, the pulse-shaped signal reflects multiple touches instead of blood pulse. Similar multiple touches with a nonliving material does not show the difference caused by a living finger.

This optical sensing of different optical absorption behaviors of the blood at different optical wavelengths can be performed in a short period for live finger detection and can be faster than optical detection of a person's heart beat using the same optical sensor.

In LCD displays, the LCD backlighting illumination light is white light and thus contains light at both the visible and IR spectral ranges for performing the above live finger detection at the optical sensor module. The LCD color filters in the LCD display module can be used to allow the optical sensor module to obtain measurements in FIGS. 14 and 15.

In addition, the designated light sources 436 for producing the illumination light for optical sensing can be operated to emit probe light at the selected visible wavelength and IR wavelength at different times and the reflected probe light at the two different wavelengths is captured by the optical detector array 621 to determine whether touched object is a live finger based on the above operations shown in FIGS. 14 and 15. Notably, although the reflected probe light at the selected visible wavelength and IR wavelength at different times may reflect different optical absorption properties of the blood, the fingerprint image is always captured by both the probe light the selected visible wavelength and the probe light at the IR wavelength at different times. Therefore, the fingerprint sensing can be made at both the visible wavelength and IR wavelength.

Figure 16:
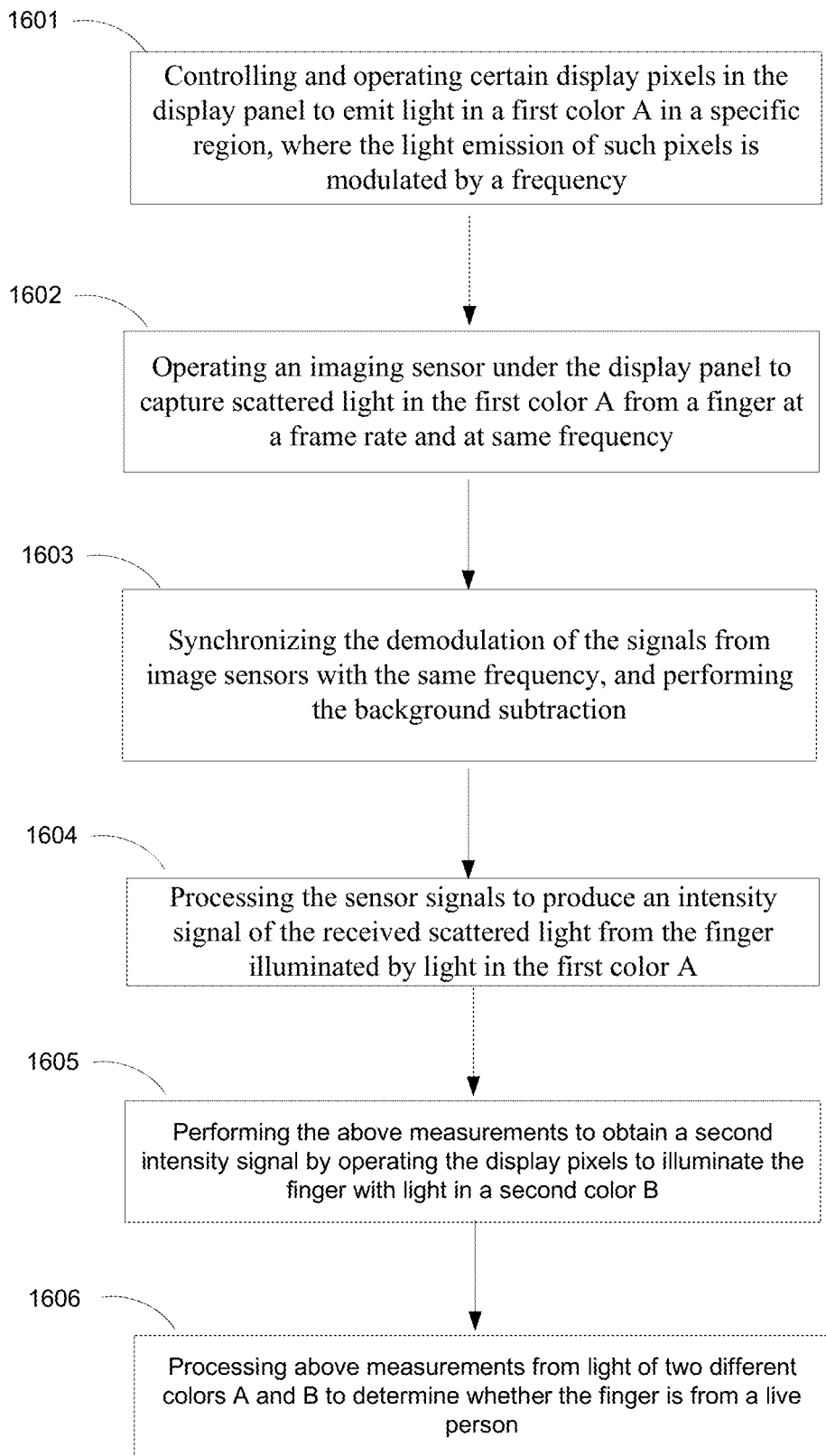

FIG. 16 shows an example of an operation process for determining whether an object in contact with the LCD display screen is part of a finger of a live person by operating the one or more illumination light sources for optical sensing to illuminate the finger with light in two different light colors.

For yet another example, the disclosed optical sensor technology can be used to detect whether the captured or detected pattern of a fingerprint or palm is from a live person's hand by a "live finger" detection mechanism by other mechanisms other than the above described different optical absorptions of blood at different optical wavelengths. For example, a live person's finger tends to be moving or stretching due to the person's natural movement or motion (either intended or unintended) or pulsing when the blood flows through the person's body in connection with the heartbeat. In one implementation, the optical sensor module can detect a change in the returned light from a finger or palm due to the heartbeat/blood flow change and thus to detect whether there is a live heartbeat in the object presented as a finger or palm. The user authentication can be based on the combination of the both the optical sensing of the fingerprint/palm pattern and the positive determination of the presence of a live person to enhance the access control. For yet another example, as a person touches the LCD display screen, a change in the touching force can be reflected in one or more ways, including fingerprint pattern deforming, a change in the contacting area between the finger and the screen surface, fingerprint ridge widening, or a blood flow dynamics change. Those and other changes can be measured by optical sensing based on the disclosed optical sensor technology and can be used to calculate the touch force. This touch force sensing can be used to add more functions to the optical sensor module beyond the fingerprint sensing.

In the above examples where the fingerprint pattern is captured on the optical detector array via an imaging module as in FIG. 4B and FIG. 6B, optical distortions tend to degrade the image sensing fidelity. Such optical distortions can be corrected in various ways. For example, a known pattern can be used to generate an optical image at the optical detector array and the image coordinates in the know pattern can be correlated to the generated optical image with distortions at the optical detector array for calibrating the imaging sensing signals output by the optical detector array for fingerprint sensing. The fingerprint sensing module calibrates the output coordinates referencing on the image of the standard pattern.

In light of the disclosure in this patent document, various implementations can be made for the optical sensor module as disclosed.

For example, a display panel can be constructed in which each pixel emitting lights, and can be controlled individually; the display panel includes an at least partially transparent substrate; and a cover substrate, which is substantially transparent. An optical sensor module is placed under the display panel to sense the images form on the top of the display panel surface. The optical sensor module can be used to sense the images form from light emitting from display panel pixels. The optical sensor module can include a transparent block with refractive index lower than the display panel substrate, and an imaging sensor block with an imaging sensor array and an optical imaging lens. In some implementations, the low refractive index block has refractive index in the range of 1.35 to 1.46 or 1 to 1.35.

For another example, a method can be provided for fingerprint sensing, where light emitting from a display panel is reflected off the cover substrate, a finger placed on top of the cover substrate interacts with the light to modulate the light reflection pattern by the fingerprint. An imaging sensing module under the display panel is used to sense the reflected light pattern image and reconstruct fingerprint image. In one implementation, the emitting light from the display panel is modulated in time domain, and the imaging sensor is synchronized with the modulation of the emitting pixels, where a demodulation process will reject most of the background light (light not from pixels being targeted).

Various design considerations for the disclosed under-screen optical sensor module for optical fingerprint sensing are further described in Attachment 3 entitled "MULTI-FUNCTION FINGERPRINT SENSOR AND PACKAGING" (41 pages in text and 26 sheets of drawings) as part of U.S. Provisional Patent Application No. 62/289,328, and U.S. Provisional Patent Application No. 62/330,833, and International Patent Application No. PCT/US2016/038445, filed on Jun. 20, 2016 (claiming priority from U.S. Provisional Patent Application No. 62/181,718, filed on Jun. 18, 2015, and published under No. WO 2016/205832 on Dec. 22, 2016), and International Patent Application No. PCT/CN2016/104354, filed on Nov. 2, 2016 (claiming priority from U.S. Provisional Patent Application No. 62/249,832, filed on Nov. 2, 2015, and published under No. WO 2017/076292 on May 11, 2017). The entire disclosures of the above-mentioned patent applications are incorporated by reference as part of the disclosure of this patent document.

In various implementations of the under-screen optical sensor module technology for fingerprint sensing disclosed herein, the optical imaging of the illuminated touched portion of a finger to the optical detector array in the under-screen optical sensor module can be achieved without using an imagine module such as a lens by imaging the returned light from the touched portion of the finger under optical illumination. One technical challenge for optical fingerprint sensing without an imaging module is how to control the spreading of the returned light that may spatially scramble returned light from different locations on the touched portion of the finger at the optical detector array so that the spatial information of different locations may be lost when such returned light reaches the optical detector array. This challenge can be addressed by using optical collimators or an array of pinholes to replace the optical imaging module in the under-screen optical sensor module for detecting a fingerprint by optical sensing. A device for implementing such optical fingerprint sending can include a device screen that provides touch sensing operations and includes a display panel structure having light emitting display pixels, each pixel operable to emit light for forming a portion of a display image; a top transparent layer formed over the device screen as an interface for being touched by a user for the touch sensing operations and for transmitting the light from the display structure to display images to a user; and an optical sensor module located below the display panel structure to receive light that is emitted by at least a portion of the light emitting display pixels of the display structure and is returned from the top transparent layer to detect a fingerprint, the optical sensor module including an optical detector array that receives the returned light and an array of optical collimators or pinholes located in a path of the returned light to the optical detector array. The array of optical collimators is used to collect the returned light from the display panel structure and to separate light from different locations in the top transparent layer while directing the collected returned light to the optical detector array.

The imaging by using collimators relies on using different collimators at different locations to spatially separate light from different regions of a fingerprint to different optical detectors in the optical detector array. The thickness or length of each collimator along the collimator can be designed to control the narrow field of optical view of each collimator, e.g., the light from only a small area on the illuminated finger is captured by each collimator and is projected onto a few adjacent optical detectors in the optical detector array. As an example, the thickness or length of each collimator along the collimator can be designed to be large, e.g., a few hundred microns, so that the field of optical view of each collimator may allow the collimator to deliver imaging light to a small area on the optical detector array, e.g., one optical detector or a few adjacent optical detectors in the optical detector array (e.g., an area of tens of microns on each side on the optical detector array in some cases).

The following sections explain how an array of optical collimators or pinholes can be used for under-screen optical fingerprint sensing by the examples for using optical collimators in optical fingerprint sensing in hybrid sensing pixels each having a capacitive sensor for capturing fingerprint information and an optical sensor for capturing fingerprint information.

Figure 17A:
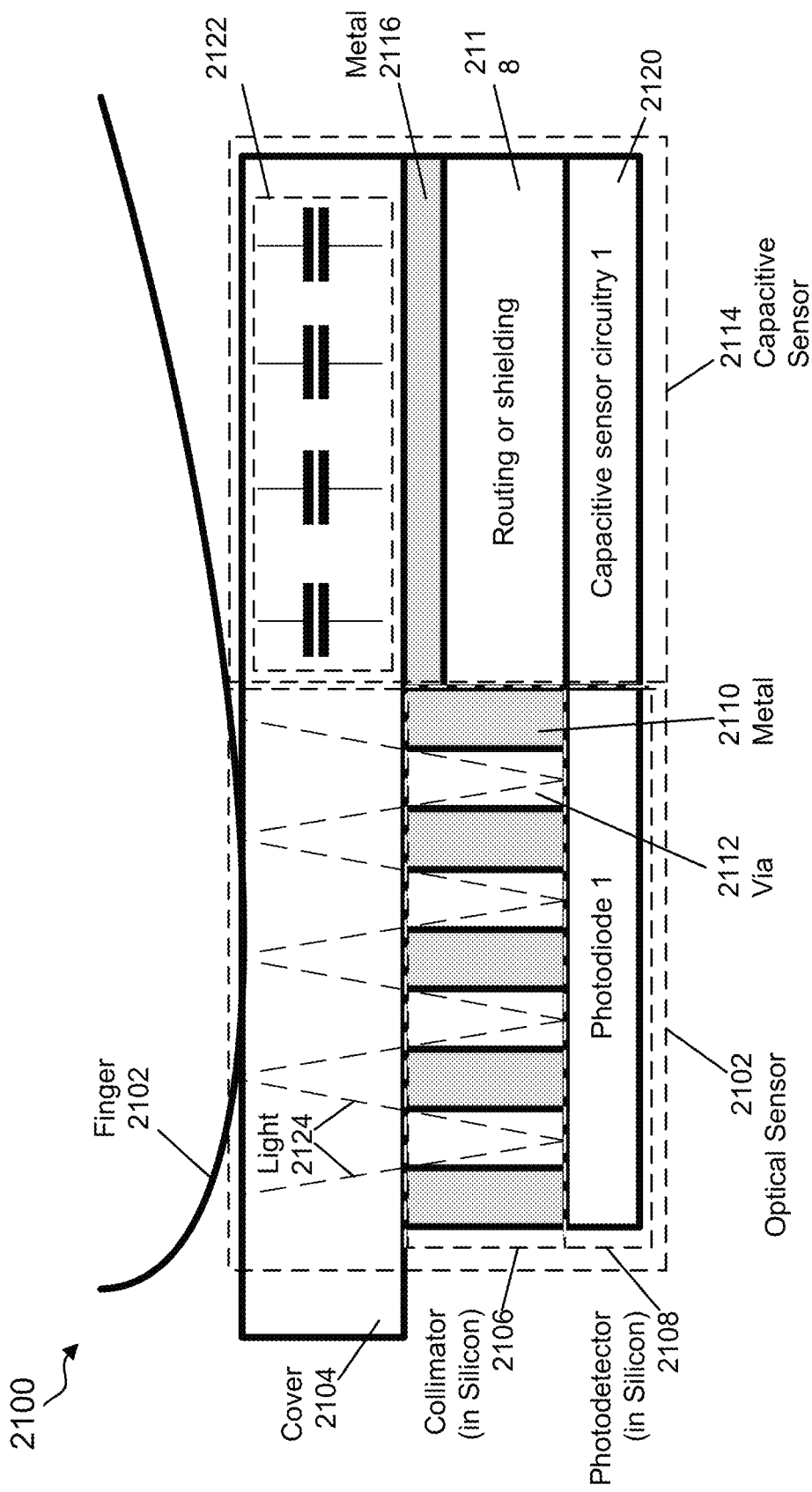
FIGS. 17A-17B, 18 and 19A-19C show optical collimator designs for optical fingerprint sensing suitable for implementing the disclosed under-screen optical sensor module technology.
Figure 17B:
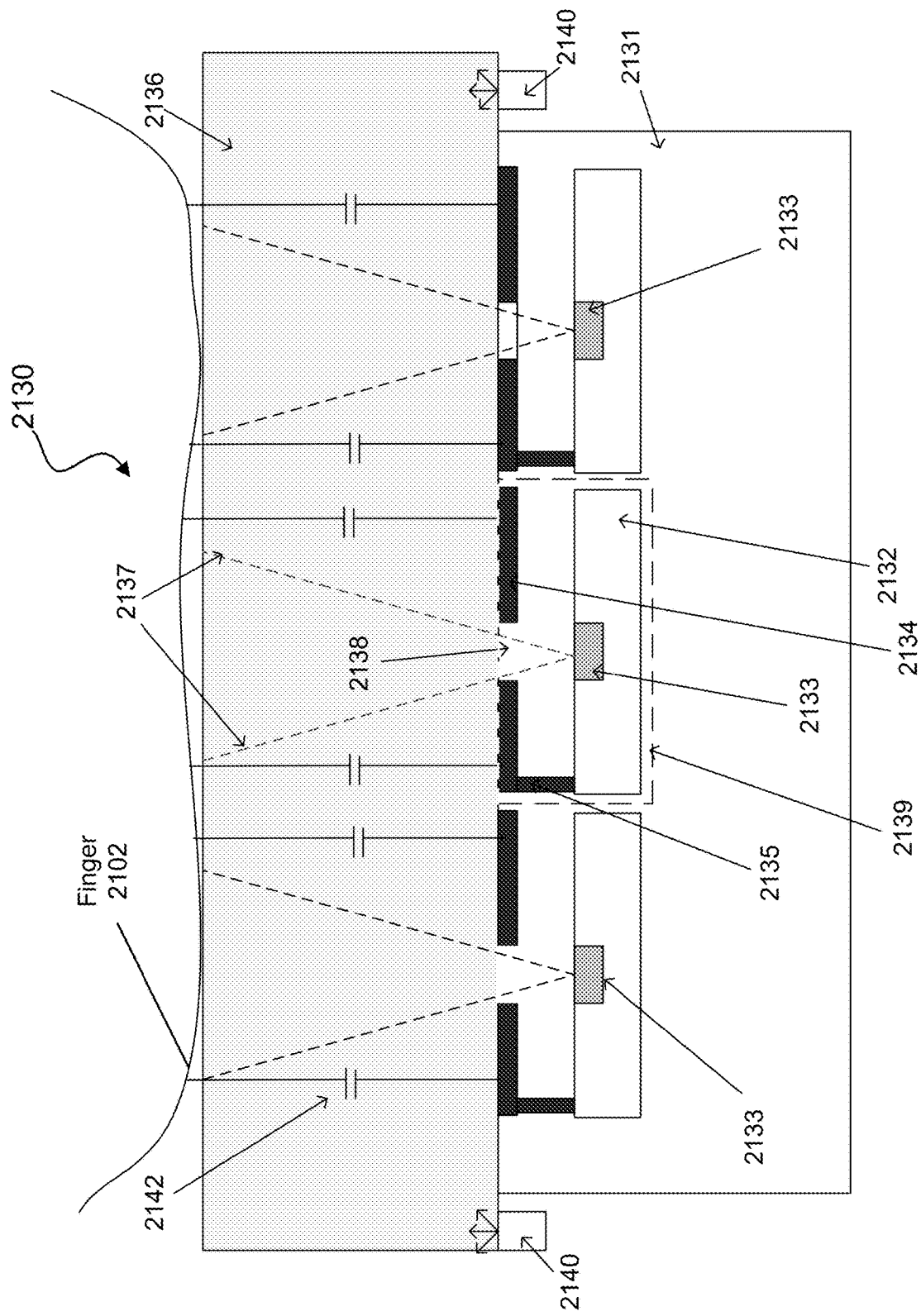

FIGS. 17A and 17B show two examples of hybrid sensing pixel designs that combine capacitive sensing and optical sensing within the same sensing pixel.

FIG. 17A shows an example of a fingerprint sensor device 2100 that incorporates a capacitive sensor in addition to an optical sensor for each sensor pixel of an array of sensor pixels in capturing fingerprint information. By combining both capacitive sensors and optical sensors, fingerprint images obtained with the optical sensors can be used to better resolve the 3D fingerprint structure obtained with the capacitive sensors. For illustrative purposes, the structure shown in FIG. 17A represents one sensor pixel in an array of sensor pixels and each sensor pixel includes an optical sensor 2102 and a capacitive sensor 2114 that are disposed next to each other within the same pixel.

The optical sensor 2102 includes a photodetector 2108 and a collimator 2106 disposed over the photodetector 2108 to narrow or focus reflected light 2124 from finger 2102 toward the photodetector 2108. One or more light sources, such as LEDs (not shown) can be disposed around the collimator 2106 to emit light, which is reflected off the finger as reflected light 2124 and is directed or focused toward the corresponding photodetector 2108 to capture a part of the fingerprint image of the finger 2102. The collimator 2106 can be implemented using an optical fiber bundle or one or more metal layer(s) with holes or openings. This use of multiple optical collimators above the optical detector array may be used as a lensless optical design for capturing the fingerprint image with a desired spatial resolution for reliable optical fingerprints sensing. FIG. 17A shows the collimator 2106 implemented using one or more metal layers 2110 with holes or openings 2112. The collimator 2106 in the layer between the top structure or layer 2104 and the photodetectors 2108 in FIG. 17A includes multiple individual optical collimators formed by optical fibers or by holes or openings in one or more layers (e.g., silicon or metal) and each of such individual optical collimators receives light ray 2124 in a direction along the longitudinal direction of each optical collimator or within a small angle range that can be captured by the top opening of each opening or hole and by the tubular structure as shown so that light rays incident in large angles from the longitudinal direction of each optical collimator are rejected by each collimator from reaching the optical photodiode on the other end of the optical collimator.

In the capacitive sensing part of each sensing pixel, the capacitive sensor 2114 includes a capacitive sensor plate 2116 that is electromagnetically coupled to a portion of a finger that is either nearby or in contact with the sensing pixel to perform the capacitive sensing. More specifically, the capacitive sensor plate 2116 and the finger 2102 interact as two plates of one or more capacitive elements 2122 when the finger 2102 is in contact with or substantially near the optional cover 2104 or a cover on a mobile device that implements the fingerprint sensor device 2100. The number of capacitive sensor plates 2116 can vary based on the design of the capacitive sensor 2114. The capacitive sensor plate 2116 can be implemented using one or more metal layers. The capacitive sensor plate 2116 is communicatively coupled to capacitive sensor circuitry 2120 so that the capacitive sensor circuitry 2120 can process the signals from the capacitive sensor plate 2116 to obtain data representing the 3D fingerprint structure. A routing or shielding material can be disposed between the capacitive sensor plate 2116 and the capacitive sensor circuitry to electrically shield the metal plate 2116. The capacitive sensor circuitry 2120 can be communicatively coupled to both the capacitive sensor plate 2116 and the photodetector 2108 to process both the signal from the capacitive sensor plate 2116 and the signal from the photodetector 2108. In FIG. 17A, the capacitive sensor and the optical sensor within each hybrid sensing pixel are adjacent to and displaced from each other without being spatially overlapped.

In implementations, the optical sensing features in the hybrid sensor design in FIG. 17A such as the optical collimator design can be used in a under-screen optical sensor module. Therefore, the optical sensing with the optical collimator feature in FIG. 17A may be implemented in a mobile device or an electronic device is capable of detecting a fingerprint by optical sensing to include a display screen structure; a top transparent layer formed over the display screen structure as an interface for being touched by a user and for transmitting the light from the display screen structure to display images to a user; and an optical sensor module located below the display screen structure to receive light that is returned from the top transparent layer to detect a fingerprint. The optical sensor module includes an optical detector array of photodetectors that receive the returned light and an array of optical collimators to collect the returned light from the top transparent layer via the display screen structure and to separate light from different locations in the top transparent layer while directing the collected returned light through the optical collimators to the photodetectors of the optical detector array.

FIG. 17B illustrates another example of a fingerprint sensor device 2130 that structurally integrates an optical sensor and a capacitive sensor in each hybrid sensor pixel in a spatially overlap configuration in an array of sensor pixels to reduce the footprint of each hybrid sensing pixel. The fingerprint sensor device 2130 includes a semiconductor substrate 2131, such as silicon. Over the substrate 2131, multiple sensing elements or sensing pixels 2139 are disposed. Each sensing element or sensing pixel 2139 includes active electronics circuitry area 2132 including CMOS switches, amplifier, resistors and capacitors for processing sensor signals. Each sensing pixel or sensing element 2139 includes a photodetector 2133 disposed or embedded in the active electronics circuitry area 2132. A capacitive sensor plate or a top electrode 2134 of the capacitive sensor for capacitive sensing is disposed over a photodetector 2133 and includes a hole or opening 2138 on the sensor plate 2134 to function also as a collimator of light for directing light onto the photodetector 2133. A via 2135 filled with conductive material is disposed to electrically connect the top electrode 2134 to the active circuit elements 2132. By adjusting the opening or the hole and the distance of the top electrode 2134 with the photodetector 2133, the light collecting angle 2137 of the photodetector (e.g., photodiode) 2133 can be adjusted. The fingerprint sensor device 2130 is covered by a protective cover 2136, which includes hard materials, such as sapphire, glass etc. Photodetector 2133 light collection angle 2137 can be designed to preserve the spatial resolution of the image collected by the photodiode arrays. A light source 2140, such as an LED, is placed under the cover, on the side of fingerprint sensor device 2130 to emit light, which is reflected off the finger and directed toward the photodetector 2133 to capture the fingerprint image. When a finger touches or comes substantially near the protective cover, the finger and the sensing top electrode 2134 in combination form a capacitive coupling (e.g., capacitor 2142) between the human body and sensing top electrode 2134. The fingerprint sensor device 2130 that includes both optical and capacitive sensors can acquire images of both a light reflection image of fingerprint and also a capacitive coupling image. The sensing top electrode 2134 serves dual purpose: 1) for capacitive sensing, and 2) as a collimator (by fabricating one or more holes on the sensing top electrode 2134) to direct, narrow or focus reflected light from the finger toward the photodetector 2133. Reusing the sensing top electrode 2134 eliminates the need for additional metal layer or optical fiber bundle, and thus reduces each pixel size and accordingly the overall size of the fingerprint sensor device 2130.

In FIG. 17B, the optical sensing design uses the holes or openings 2138 formed between the top layer 2136 and the bottom array of photodetectors 2133 as an optical collimators to select only light rays within certain angles 2137 to preserve the spatial resolution of the image collected by the photodetectors 2133 in the photodetector array as illustrated. Similar to the fiber or other tubular shaped optical collimators in FIG. 17A, the holes or openings 2138 formed between the top layer 2136 and the bottom array of photodetectors 2133 constitute optical collimators to collect the returned light from the top transparent layer via the display screen structure and to separate light from different locations in the top transparent layer while directing the collected returned light through the optical collimators to the photodetectors 2133.

Figure 18:
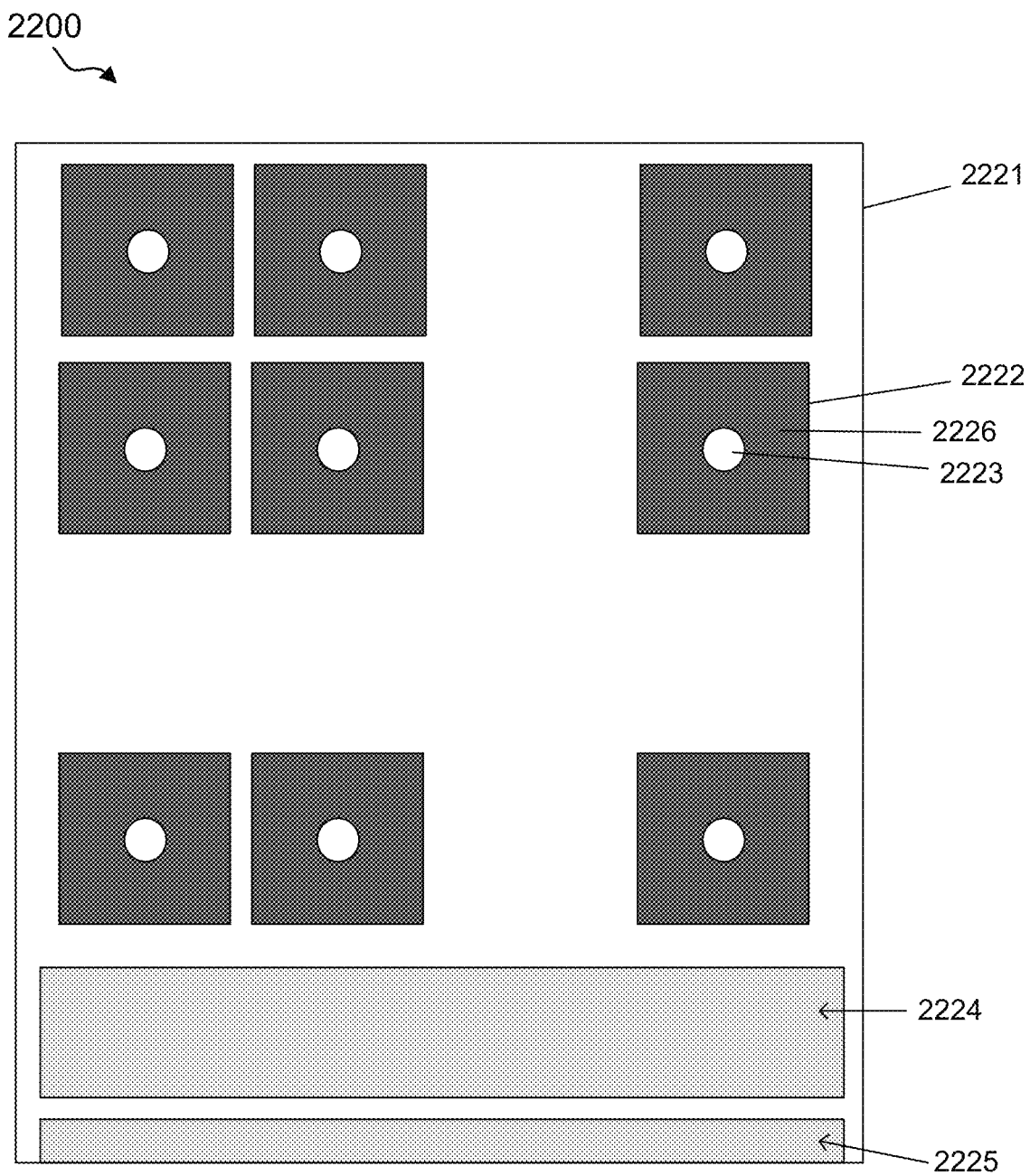

FIG. 18 is a top-down view of an exemplary hybrid fingerprint sensor device 2200 incorporating both an optical sensor and a capacitive sensor in each hybrid sensing pixel. The fingerprint sensor device 2200 is implemented as a CMOS silicon chip 2221 that includes an array of hybrid (incorporating both an optical sensor and a capacitive sensor) sensing elements or pixels 2222. Alternatively, the optical layout in FIG. 18 can also be for all optical sensing designs disclosed in this document where the openings or holes 2223 represent the optical collimators in FIG. 17A or 17B. The size or dimension of the sensing elements can be in the range of 25 μm to 250 μm, for example. The hybrid sensor device 2200 can include an array of support circuitry including amplifiers, ADCs, and buffer memory in a side region 2224. In addition, the hybrid sensor device 2200 can include an area for wire bonding or bump bonding 2225. A top layer 2226 of the hybrid sensor element 2222 can include a metal electrode for capacitive sensing. One or more openings or holes 2223 can be fabricated on each top metal electrode 23 to structurally serve as a collimator for directing light in a vertical direction to shine on a photodetector under the top electrode. Thus, the top layer 2226 structure can serve dual purposes of optical and capacitive sensing. A sensor device processor can be provided to process the pixel output signals from hybrid sensing pixels to extract the fingerprint information.

In addition to sharing the same structure for capacitive sensing and for focusing light in the vertical direction as a collimator, one instance of sensor signal detection circuitry can be shared between the optical and capacitive sensors to detect the sensor signals from both a photodetector and a capacitive sensor plate.

Figure 19A:
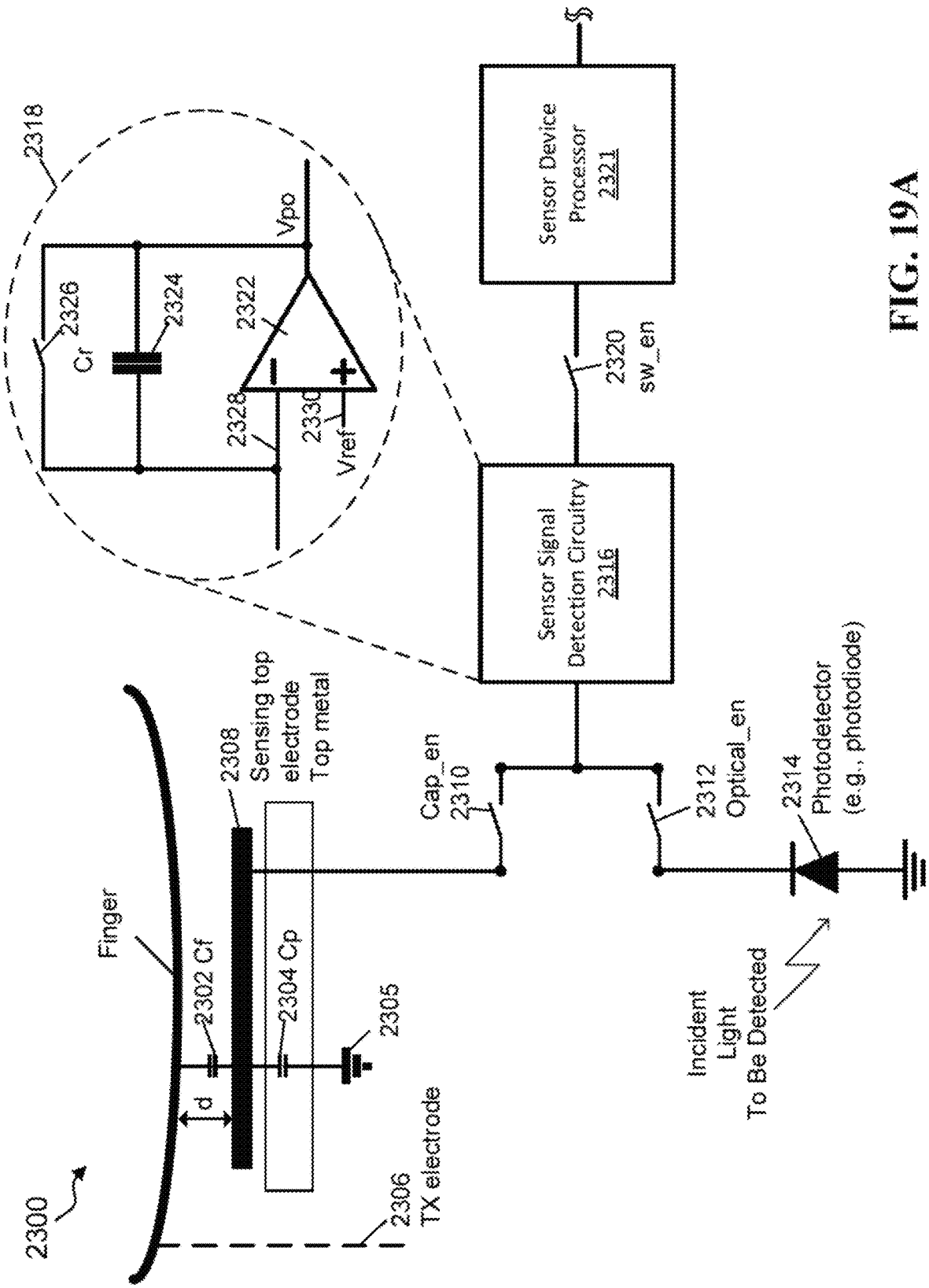

FIG. 19A illustrates a circuit diagram for an exemplary hybrid fingerprint sensing element or pixel 2300 having both capacitive sensing and optical sensing functions for fingerprints. The exemplary sensor pixel 2300 includes sensor signal detection circuitry 2316 to selectively switch between detecting or acquiring sensor signals from a sensing top electrode (e.g., a top metal layer) 2308 based on capacitive sensing and a photodetector (e.g., a photodiode) 2314 based on optical sensing to acquire both a reflective optical image from the photodetector 2314 and a capacitive coupled image from the capacitive sensor electrode 2308 from a finger. In some implementations, the two images from the two sensing mechanisms in each hybrid sensing pixel can be serially processed by the sensor signal detection circuitry. In the illustrated example, switches 2310 and 2312 have first terminals that are electrically coupled to the sensing top electrode 2308 and the photodetector 2314, respectively, and second terminals that are coupled to a common input terminal of the sensor signal detection circuitry 2316 to provide corresponding optical detector signal from the photodetector 2314 and the corresponding capacitive sensing signal from the sensing top electrode 2308 to the sensor signal detection circuitry 2316. When the switch 2310 is turned off (CAP_EN=0) and the switch 2312 is turned on (Optical_en=1), the sensor signal detection circuitry 2316 acquires the optical detector signal representing the optical image of the scanned fingerprint received at the particular hybrid sensing pixel. The sensor signal detection circuitry 2316 can acquire the capacitive sensing signal representing the capacitive image of the scanned fingerprint when switch 2310 CAP_EN=1 and Optical_en=0. After both the optical and capacitive images are acquired, both images can be processed in downstream circuitry separately and in combination to identify the fingerprint characteristics.

With the two modalities of imaging by the above hybrid sensing pixels, the performance of the fingerprint identification can be enhanced by making use of the two types of the images in different ways. This enhanced fingerprint identification can be achieved by the sensor device processor, such as sensor device processor 2321, for processing the pixel output signals from the hybrid sensing pixels to extract the fingerprint information. For example, the capacitive image can provide a 3D image on the depth of the ridges and valleys of the fingerprint features. Complementing the 3D capacitive image, the optical image can provide a high resolution 2D information on the fingerprint characteristics. The optical 2D image having a higher spatial resolution can be used to recover the capacitive sensing image resolution because both images information on the same ridges of the fingerprint. In some implementations where the capacitive sensing method may be more sensitive and accurate on identifying the valleys of the fingerprint than the optical sensing method, the spatial resolution of images acquired using the capacitive sensing method can degrade based on the thickness of the cover. This aspect of the capacitive sensing can be supplemented by the optical sensing. In operation, the sensor response may be fixed and the point spread function of the capacitive sensor may be fixed for all sensor positions. The higher resolution optical sensing can be used as a resolution recovery method and can be applied on the capacitive sensing image to enhance the 3D image. A partial high resolution image from optical sensing can be available to help with the recovering method. Thus, the 3D capacitive image can be enhanced to provide more information on the valleys and ridges by interpolating or recovering based on the high resolution 2D image.

The enhanced 3D image can provide an improved fingerprint recognition and matching. In another example, the optical and capacitive images can be stored together to provide two comparisons each time a fingerprint recognition or matching is performed. The use of two types of images for comparison enhances the accuracy and security of the fingerprint sensing system.

The sensor signal detection circuitry 2316 can be implemented in various ways using a number different circuitry designs. In one example, integrator sensing circuitry 2318 can be implemented to store the electric charges caused by ridges and valleys touching or being substantially near the cover of the fingerprint sensor device of the cover of the mobile device. The inclusion of the integrator circuitry 2318 enhances the signal-to-noise ratio (SNR). The integrator sensing circuitry includes an operational amplifier 2322 to amplify a sensor signal, such as a capacitance related or optical related signal (e.g., voltage signal), detected by the sensing top electrode 2308 or the photodetector 2314 of the exemplary sensor pixel 2300. The sensing top electrode 2308 that include a conductive material, such as one of a variety of metals is electrically connected to a negative or inverting terminal 2328 of the amplifier 2322 through the switch 2310. The sensing top electrode 2108 and a local surface of the finger 2302 function as opposing plates of a capacitor Cf 2302. The capacitance of the capacitor Cf 2302 varies based on a distance 'd' between the local surface of the finger and the sensing top electrode 2308, the distance between the two plates of the capacitor Cf 2302. The capacitance of capacitor Cf 2302 is inversely proportional to the distance 'd' between the two plates of the capacitor Cf 2302. The capacitance of capacitor Cf 2302 is larger when the sensing top electrode 2308 is opposite a ridge of the finger than when opposite a valley of the finger.

In addition, various parasitic or other capacitors can be formed between different conductive elements in the exemplary sensor pixel 2300. For example, a parasitic capacitor CP 2304 can form between the sensing top electrode 2308 and a device ground terminal 2305. Device ground is coupled to earth ground closely. Another capacitor Cr 2324 can form between an output conductor of the amplifier 2322 and the negative or inverting terminal 2328 of the amplifier 2322 and functions as a feedback capacitor to the amplifier 2322. Also, a switch 2326 can be coupled between the output of the amplifier 2322 and the negative or inverting terminal 2328 of the amplifier 2322 to reset the integrator circuitry 2318.

The positive terminal of the amplifier 2322 is electrically connected to an excitation signal Vref. The excitation signal Vref can be directly provided to the positive terminal of a dedicated amplifier in each sensor pixel. By providing the excitation signal Vref directly to the positive terminal of the amplifier 2322, the exemplary sensor pixel 2100 becomes an active sensor pixel. In addition, providing the excitation signal Vref directly to the positive terminal of the amplifier 2322 eliminates the need to include an excitation electrode, common to all sensor pixels, which reduces a conductive (e.g., metal) layer from the semiconductor structure of the sensor chip. In some implementations, an optional excitation electrode 2306 can be implemented to enhance the SNR based on the design of the sensor pixel. In addition, by providing the excitation signal Vref 2330 directly to the amplifier 2322, the excitation signal Vref 2322 is not applied directly to the finger to avoid potentially irritating or injuring the finger. Moreover, when the excitation electrode for applying the excitation signal directly to the finger is not used, all components of the fingerprint sensor device can be integrated into a single packaged device, and the entire fingerprint sensor device can be disposed under the protective cover glass. With the entire fingerprint sensor device disposed under the protective cover glass, the fingerprint sensor device is protected from the finger and other external elements that can potentially damage the fingerprint sensor.

In FIG. 19A, the output signal (optical and capacitive) of the sensor signal detection circuitry 2316 (e.g., Vpo of the amplifiers 2322) in the sensor pixels 2300 is electrically coupled to a switch 2320 to selectively output the output signal Vpo from the sensor pixel 2300 to a signal processing circuitry including a filter. The switch 2320 can be implemented using a transistor or other switching mechanisms and electrically coupled to a controller to control the switching of the switch 2320. By controlling the switches 2320, 2310 and 2312, the sensor pixels in an array of sensor pixels can be selectively switched between acquiring the optical signals and the capacitive signals. In one implementation, the optical or capacitive signal can be acquired for each line, row or column of sensor pixels in the array and then switched to acquire the other type of signal for the line, row or column. The switching between the optical and capacitive signal acquisition can be performed line-by-line. In another implementation, one type of signal (capacitive or optical) can be acquired for all sensor pixels or elements in the array and then switched to acquire the other type of signal for all of the sensor pixels or elements. Thus, the switching between acquisition of different signal types can occur for the entire array. Other variations of switching between acquisition of the two types of sensor signals can be implemented.

Figure 19B:
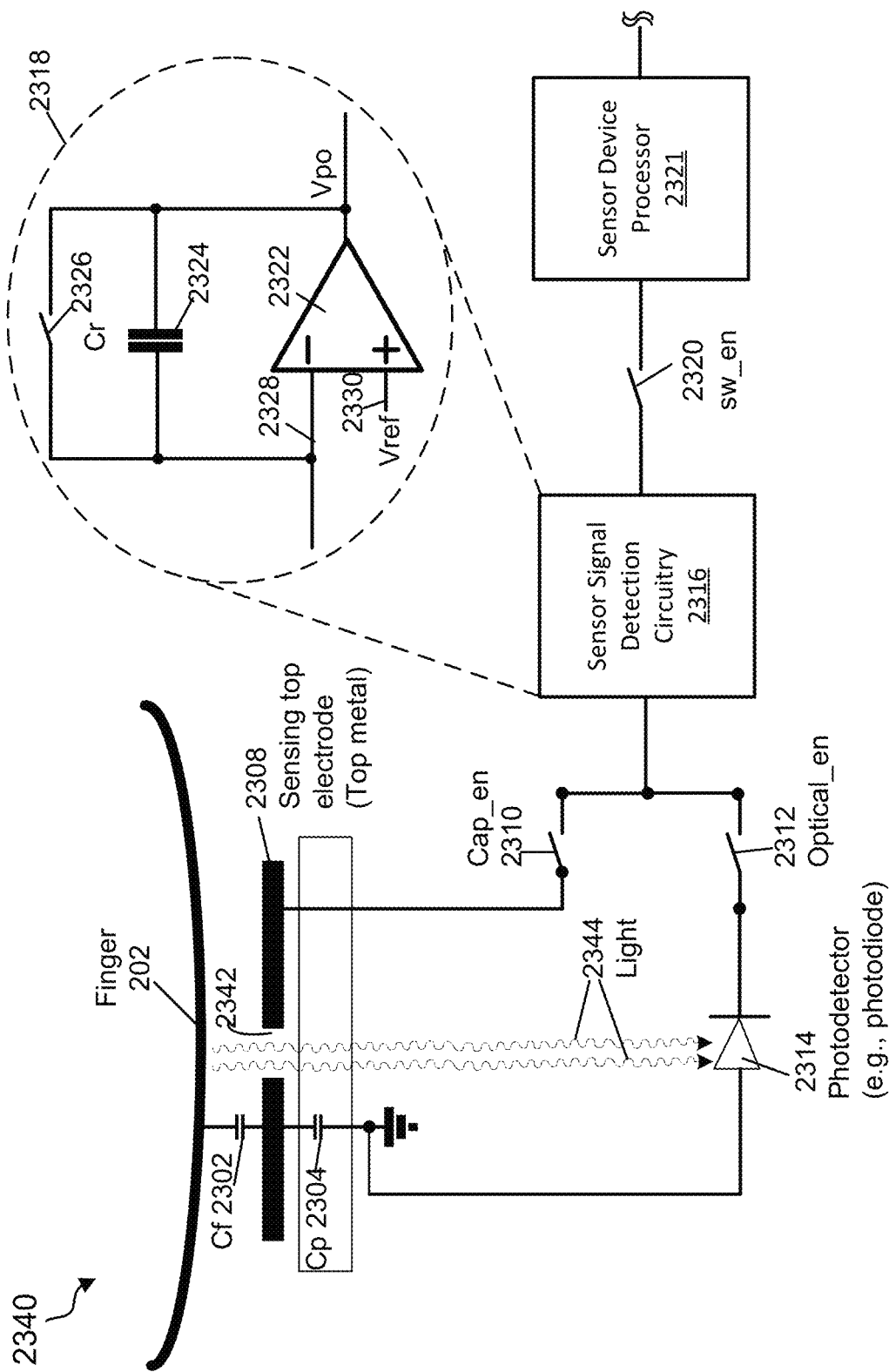

FIG. 19B illustrates a circuit diagram for another exemplary hybrid fingerprint sensing element or pixel 2340. The hybrid fingerprint sensing element or pixel 2340 is substantially the same as the hybrid fingerprint sensing element or pixel 2300 with respect to the components having the same reference number. For descriptions of the common components having the same reference number, refer to the description of FIG. 19A.

The hybrid fingerprint sensing element or pixel 2340 implements the sensing top electrode 2308 to include a hole or opening 2342 that functions as a collimator to focus or narrow the reflected light 2344 toward the photodetector 2314 (e.g., photodiode). The photodetector 2314 can be positioned or disposed below the collimator implemented using the sensing top electrode 2308 to capture the reflected light 2344 focused by the collimator 2308.

In some implementations, separate instances of sensor signal detection circuitry can be included for the optical and capacitive sensors to detect in parallel the sensor signals from both a photodetector and a capacitive sensor plate.

Figure 19C:
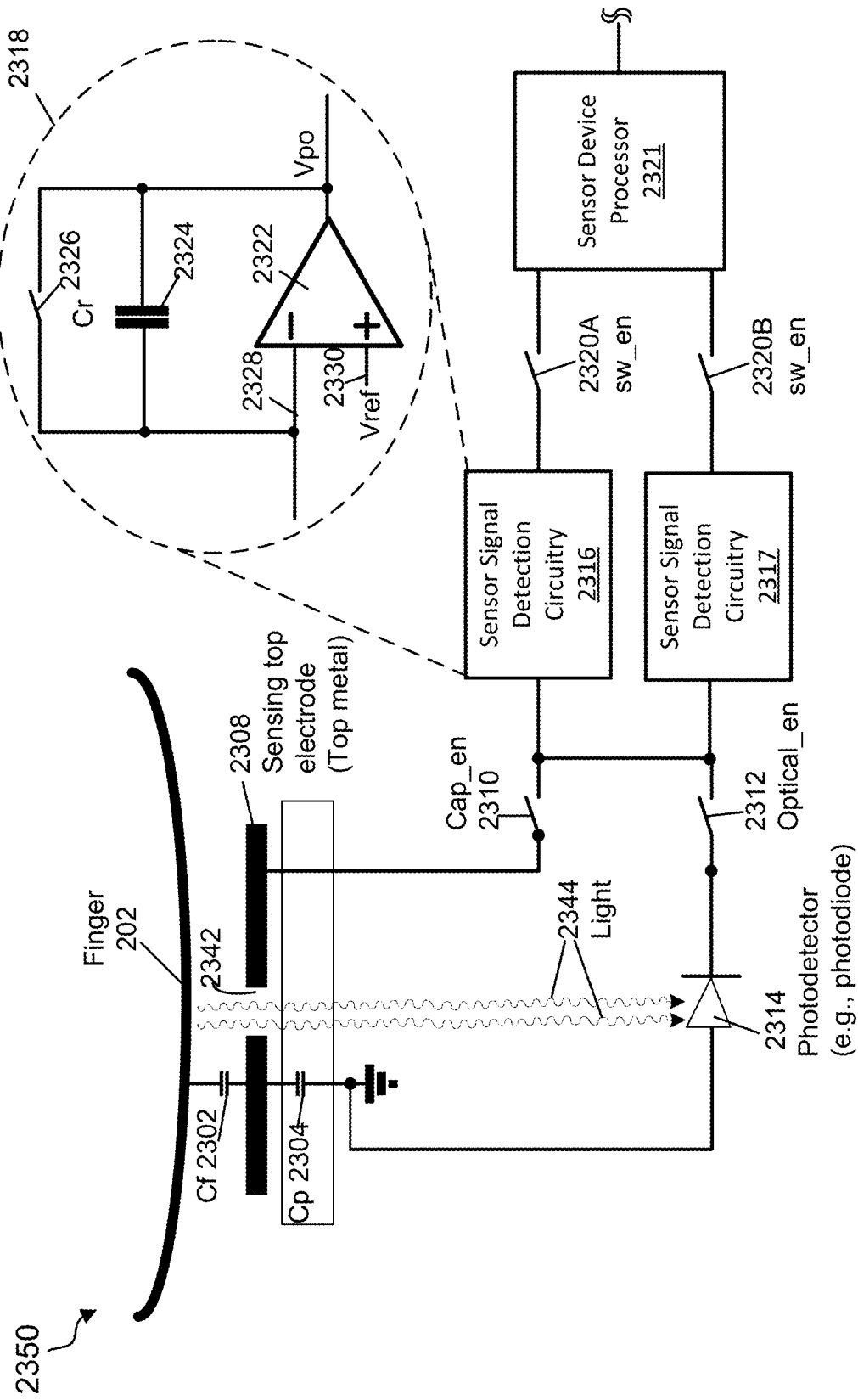

FIG. 19C illustrates a circuit diagram of an exemplary hybrid fingerprint sensing element or pixel 2350 for performing parallel detection of sensor signals from the photodetector and the capacitive sensor plate. The hybrid fingerprint sensing element or pixel 2350 is substantially the same as the hybrid fingerprint sensing element or pixel 2340 with respect to the components having the same reference number. For descriptions of the common components having the same reference number, refer to the description of FIG. 19A.

To perform sensor signal detection from both the capacitive plate and the photodetector in parallel, the hybrid fingerprint sensing element or pixel 2350 includes separate sensor signal detection circuitry 2316 and 2317 communicatively coupled to the sensing top electrode 2308 and the photodetector 2324 respectively. Sensor signal detection circuitry 2317 can be implemented to be substantially similar to sensor signal detection circuitry 2316. In some implementations, switches 2310 and 2312 can be disposed to have first terminals that are electrically coupled to the sensing top electrode 2308 and the photodetector 2314, respectively, and second terminals that are coupled to respective sensor signal detection circuitry 2316 and 2317 to provide the optical detector signal from the photodetector 2314 and the capacitive sensing signal from the sensing top electrode 2308 to the sensor signal detection circuitry 2316 and 2317 respectively When the switches 2310 and 2312 are turned on and off together, the sensor signal detection circuitry 2316 and 2317 can perform sensor signal detection from the capacitive plate 2308 and the photodetector 2314 in parallel. When the switches 2310 and 2312 are turned on and off out of phase with each other, the sensor signal detection circuitry 2316 and 2317 can perform sensor signal detection from the capacitive plate 2308 and the photodetector 2314 in series. In addition, the sensor device processor 2321 can be communicatively coupled to the sensor signal detection circuitry 2316 and 2317 either directly or indirectly through switches 2320A and 2320B to process the detected sensor signals from the capacitive plate 2308 and the photodetector 2314 in parallel or in series.

In another aspect of the disclosed technology, the optical sensor described with respect to FIGS. 17A, 17B, 18, 19A and 19B can be used to measure human heart beat by measuring the reflected light intensity change with time caused by blood flow variations in fingers due to the heart beat and pumping actions of the heart. This information is contained in the received light that is reflected, scattered or diffused by the finger and is carried by the optical detector signal. Thus, the optical sensor can serve multiple functions including acquiring an optical image of the fingerprint and to measure human heart beat. In implementations, a sensor device processor is used to process one or more optical detector signals to extract the heart beat information. This sensor device processor may be the same sensor device processor that processes the pixel output signals from optical sensing pixels or hybrid sensing pixels to extract the fingerprint information.

The following sections describe examples of various designs for fingerprint sensing using an under-screen optical sensor module using an array of optical collimators or pinholes for directing signal light carrying fingerprint information to the optical detector array. Such optical collimators or pinholes are placed between the LCD display screen and the optical detector array in the under-screen optical sensor module to couple desired returned light from the display panel while filtering out background light in the optical detection by the optical detector array. Implementation of such optical collimators or pinholes can simplify the optical designs of the optical detection by the optical detector array, e.g., without using complex optical imaging designs in other designs disclosed in this patent document, such as the imaging designs in FIGS. 6B, 7, 10A, and 11. In addition, implementation of such optical collimators or pinholes can simplify the optical alignment of the overall optical layout to the optical detector array and improve reliability and performance of the optical detection by the optical detector array. Furthermore, such optical collimators or pinholes can significantly simplify the fabrication and reduce the overall cost of the under-screen optical sensor module.

FIG. 20 shows an example of a smartphone having a liquid crystal display (LCD) display and an under-screen optical sensor module that includes an optical collimator array for collecting and directing light to an optical detector array for optical fingerprint sensing. The LCD-based touch sensing display system 423 implements an optical sensing module with a photo detector array 621 under the LCD display system 423.

The touch sensing display system 423 is placed under a top cover glass 431 which serves as a user interface surface for various user interfacing operations, including, e.g., touch sensing operations by the user, displaying images to the user, and an optical sensing interface to receive a finger for optical fingerprint sensing and other optical sensing operations where probe light is directed from inside the device to the top cover glass 431 to illuminate the finger. When the LCD cells in the sensing window are turned on, most of the LCD structure layers 433*a* become partially transparent although the micro structure may extinct partial of the probe light energy. The light diffuser 433*b*, the light waveguide 433*c*, the reflector film 433*d*, and the LCD module frame are treated to hold the fingerprint sensor and provide transparent or partially transparent sensing light path so that a portion of the reflected light from the top surface of the cover glass 431 can reach a photo detector array 621 within an under-LCD-screen optical sensor module for fingerprint sensing and other optical sensing operations. As illustrated, this particular example of an optical sensor module under the LCD screen includes various fingerprint sensor parts, e.g., an optical collimator array 617 for collimating and directing reflected probe light to the photo detector array 621, and an optical sensor circuit module 623 that receives and conditions the detector output signals from the photo detector array 621. The optical collimator array 617 can include optical collimators and may be a waveguide based image transmitter, an optical fiber array, a micro lens array, or a pinhole array. The optical collimators operate to limit the numeral aperture (NA) of the sampling image and to form corresponding image elements. Each optical collimator unit gets a part of the image of the touched portion of a target finger on the top glass cover 431. The transmitted light beams of all the collimators collectively form a full image of the target at the photo detector array 621. The photodiode array 621 may be a CMOS sensor of CMOS sensing pixels, a CCD sensor array or a suitable optical detector array that is sensitive to light.

The example illustrates includes an electronics module 435 for the LCD display and touch sensing operations, one or more other sensors 425 such as an optical sensor for monitoring the light level of the surroundings, optional side buttons 427 and 429 for controls of certain smartphone operations.

In the example in FIG. 20, the light sources in the illustrated example include the display back lighting light sources 434 and the extra designated probe light sources 436. The light beams 442*a* from extra designated probe light sources 436 and the light beams 442*b* from the display light sources 434 can be used as the sensor probe light for illuminating a finger in contact with the top glass cover 431 to generate the desired reflected probe light carrying the fingerprint pattern and other information to the optical sensor module.

When the LCD cells in the sensing window are turned on, most of the LCD structure layers 433*a* (include liquid crystal cells, electrodes, transparent ITO, polarizer, color filter, touch sensing layer etc.) become partially transparent although the micro structure may extinct partial of the probe light energy. The light diffuser 433*b*, the light waveguide 433*c*, the reflector film 433*d*, and the LCD module frame are treated to hold the fingerprint sensor and provide transparent or partially transparent sensing light path.

Figure 21A:
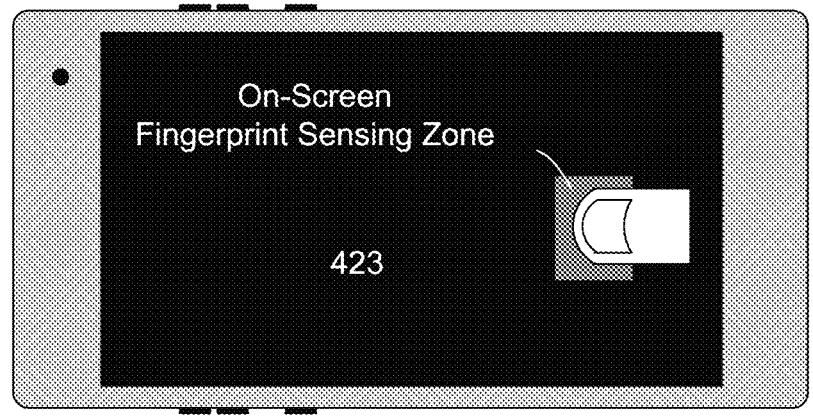
Figure 21B:
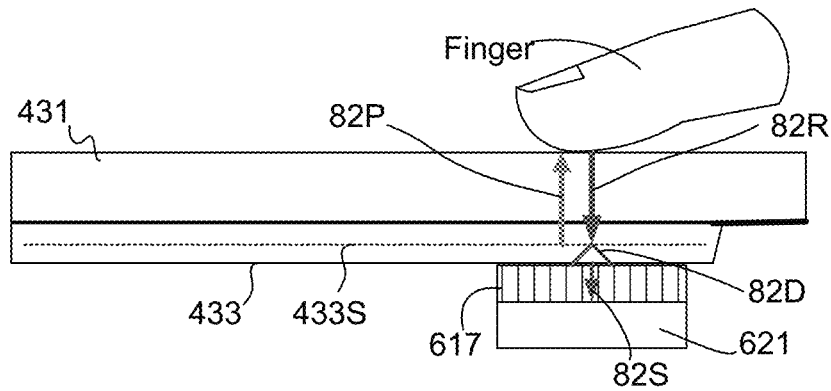

FIGS. 21A-21B further illustrate the operation of the under LCD screen optical sensor module in the above example in FIG. 20. On the top cover glass 431, a fingerprint sensing area or window is an area on the top surface of the top cover glass 431 that is right above or near the underlying optical sensor module. Since the optical sensor module is underneath the LCD structure, the sensing window is part of the contiguous top surface of the top cover glass 431 and is also part of the display area for the LCD display. Accordingly, there may be no visible physical demarcation on the top surface to indicate this sensing window. This sensing window may be indicated to a user via other means to assist the user to place a finger within the sensing window for fingerprint sensing and other optical sensing operations. For example, the extra designated probe light sources 436 may be used to illuminate the sensing window so that the area for the sensing window is distinctly different from the surrounding areas on the top cover glass and is readily visible to the user. This can be done when the LCD panel is turned off or when the LCD panel is turned on.

As shown in FIGS. 21A-21B, a user presses a finger on the sensing window and the probe light beam 82P illuminates the finger. The finger and the cover glass 431 reflect the probe light as a reflected signal light beam 82R. Various scattering interfaces 433S in the LCD module 433 diffuses the reflected signal light beam 82R to form diffused light beam 82D. Individual collimator units in the collimator array 617 select light component 82S and guide the selected light component 82S into corresponding photosensing detectors of the photodetector array 621. The photosensing detectors, e.g., photodiodes or CMOS sensing detectors, generate corresponding sensor signals that contain information on the fingerprint pattern. A portion of the source light may enter the fingerprint sensor module without first going through the finger sensing area on the top surface of the LCD panel. This part of light contributes background noise and can be eliminated by calibration. Each collimator unit of the collimator array 617 only selects the light be transmitted along its permitted direction at a relatively low optical loss to corresponding photo detectors in a part of the photodetector array 621. Accordingly, each collimator unit in the collimator array 617 and its corresponding photo detectors in the photodetector array 621 operate together to define the effective detecting optical numeral aperture NA. This NA directly defines the spatial resolution of the image produced by the optical sensor module.

Based on the disclosed under LCD screen optical sensing designs, a person's finger, either in direct touch with the LCD display screen or in a near proximity about the LCD display screen, can produce the returned light back into the LCD display screen while carrying information of a portion of the finger illuminated by the light output by the LCD display screen. Such information may include, e.g., the spatial pattern and locations of the ridges and valleys of the illuminated portion of the finger. Accordingly, the optical sensor module can be integrated to capture at least a portion of such returned light to detect the spatial pattern and locations of the ridges and valleys of the illuminated portion of the finger by optical imaging and optical detection operations. The detected spatial pattern and locations of the ridges and valleys of the illuminated portion of the finger can then be processed to construct a fingerprint pattern and to perform fingerprint identification, e.g., comparing with a stored authorized user fingerprint pattern to determine whether the detected fingerprint is a match as part of a user authentication and device access process. This optical sensing based fingerprint detection by using the disclosed optical sensor technology uses the LCD display screens as an optical sensing platform and can be used to replace existing capacitive fingerprint sensors or other fingerprint sensors that are basically self-contained sensors as "add-on" components without using light from display screens or using the display screens for fingerprint sensing for mobile phones, tablets and other electronic devices.

Notably, an optical sensor module based on the disclosed optical sensor technology can be coupled to the backside of the LCD display screen without requiring a designated area on the display surface side of the LCD display screen that would occupy a valuable device surface real estate in some electronic devices such as a smartphone, a tablet or a wearable device. Such an optical sensor module can be placed under the LCD display screen that vertically overlaps with the display screen area, and, from the user's perspective, the optical sensor module is hidden behind the display screen area. In addition, because the optical sensing of such an optical sensor module is by detecting the light from the LCD display screen and is returned from the top surface of the display area, the disclosed optical sensor module does not require a special sensing port or sensing area that is separate from the display screen area. Accordingly, different from fingerprint sensors in other designs, including, e.g., Apple's iPhone/iPad devices or Samsung Galaxy smartphone models where the fingerprint sensor is located at a particular fingerprint sensor area or port (e.g., the home button) on the same surface of the display screen but located in a designated non-displaying zone that is outside the display screen area, the optical sensor module based on the disclosed optical sensor technology can be implemented in ways that would allow fingerprint sensing to be performed at any location on the LCD display screen by using unique optical sensing designs by routing the returned light from the finger into an optical sensor and by providing proper optical imaging mechanism to achieve high resolution optical imaging sensing. In this regard, the disclosed optical sensor technology provides a unique on-screen fingerprint sensing configuration by using the same top touch sensing surface that displays images and provides the touch sensing operations without a separate fingerprint sensing area or port outside the display screen area.

In addition to fingerprint detection by optical sensing, the optical sensing may be used to measure other parameters. For example, the disclosed optical sensor technology can measure a pattern of a palm of a person given the large touch area available over the entire LCD display screen (in contrast, some designated fingerprint sensors such as the fingerprint sensor in the home button of Apple's iPhone/iPad devices have a rather small and designated off-screen fingerprint sensing area that is highly limited in the sensing area size not suitable for sensing large patterns). For yet another example, the disclosed optical sensor technology can be used not only to use optical sensing to capture and detect a pattern of a finger or palm that is associated with a person, but also to use optical sensing or other sensing mechanisms to detect whether the captured or detected pattern of a fingerprint or palm is from a live person's hand by a "live finger" detection mechanism based on the fact that a live person's finger tends to be moving or stretching due to the person's natural movement or motion (either intended or unintended) or pulsing when the blood flows through the person's body in connection with the heartbeat. In one implementation, the optical sensor module can detect a change in the returned light from a finger or palm due to the heartbeat/blood flow change and thus to detect whether there is a live heartbeat in the object presented as a finger or palm. The user authentication can be based on the combination of the both the optical sensing of the fingerprint/palm pattern and the positive determination of the presence of a live person to enhance the access control. For yet another example, the optical sensor module may include a sensing function for measuring a glucose level or a degree of oxygen saturation based on optical sensing in the returned light from a finger or palm. As yet another example, as a person touches the LCD display screen, a change in the touching force can be reflected in one or more ways, including fingerprint pattern deforming, a change in the contacting area between the finger and the screen surface, fingerprint ridge widening, or a blood flow dynamics change. Such changes can be measured by optical sensing based on the disclosed optical sensor technology and can be used to calculate the touch force. This touch force sensing adds more functions to the optical sensor module beyond the fingerprint sensing.

With respect to useful operation or control features in connection with the touch sensing aspect of the LCD display screen, the disclosed optical sensor technology can provide triggering functions or additional functions based on one or more sensing results from the optical sensor module to perform certain operations in connection with the touch sensing control over the LCD display screen. For example, the optical property of a finger skin (e.g., the index of refraction) tends to be different from other artificial objects. Based on this, the optical sensor module may be designed to selectively receive and detect returned light that is caused by a finger in touch with the surface of the LCD display screen while returned light caused by other objects would not be detected by the optical sensor module. This object-selective optical detection can be used to provide useful user controls by touch sensing, such as waking up the smartphone or device only by a touch via a person's finger or palm while touches by other objects would not cause the device to wake up for energy efficient operations and to prolong the battery use. This operation can be implemented by a control based on the output of the optical sensor module to control the waking up circuitry operation of the LCD display screen which, for example, may include designed extra light sources for optical sensing and the designed extra light sources may turned on in a flash mode to intermittently emit flash light to the screen surface for sensing any touch by a person's finger or palm while the LCD display screen can be placed in a sleep mode to save power. In some implementations, the wake-up sensing light can be in the infrared invisible spectral range so a user will not experience any visual of a flash light.

An optical sensor module based on the disclosed optical sensor technology can be coupled to the backside of the LCD display screen without requiring creation of a designated area on the surface side of the LCD display screen that would occupy a valuable device surface real estate in some electronic devices such as a smartphone, a tablet or a wearable device. This aspect of the disclosed technology can be used to provide certain advantages or benefits in both device designs and product integration or manufacturing.

In some implementations, an optical sensor module based on the disclosed optical sensor technology can be configured as a non-invasive module that can be easily integrated to a LCD display screen without requiring changing the design of the LCD display screen for providing a desired optical sensing function such as fingerprint sensing. In this regard, an optical sensor module based on the disclosed optical sensor technology can be independent from the design of a particular LCD display screen design due to the nature of the optical sensor module: the optical sensing of such an optical sensor module is by detecting the light from the LCD display screen and is returned from the top surface of the display area, and the disclosed optical sensor module is coupled to the backside of the LCD display screen for receiving the returned light from the top surface of the display area and thus does not require a special sensing port or sensing area that is separate from the display screen area. Accordingly, such an optical sensor module can be used to combine with LCD display screens to provide optical fingerprint sensing and other sensor functions on a LCD display screen without using a specially designed LCD display screen with hardware especially designed for providing such optical sensing. This aspect of the disclosed optical sensor technology enables a wide range of LCD display screens to be used in smartphones, tablets or other electronic devices with enhanced functions from the optical sensing of the disclosed optical sensor technology.

For example, for an existing phone assembly design that does not provide a separate fingerprint sensor as in the Apple iPhones or Samsung models, such an existing phone assembly design can integrate the under-screen optical sensor module as disclosed herein without changing the touch sensing-display screen assembly to provide an added on-screen fingerprint sensing function. Because the disclosed optical sensing does not require a separate designated sensing area or port as in the case of the Apple iPhones/Samsung phones with a front fingerprint sensor outside the display screen area, or some smartphones with a designated rear fingerprint sensor on the backside like in some models by Huawei, Xiaomi, Google or Lenovo, the integration of the on-screen fingerprint sensing disclosed herein does not require a substantial change to the existing phone assembly design or the touch sensing display module that has both the touch sensing layers and the display layers. Thus, no external sensing port and no extern hardware button are needed on the exterior of a device are needed for adding the disclosed optical sensor module for fingerprint sensing. The added optical sensor module and the related circuitry are under the display screen inside the phone housing and the fingerprint sensing is conveniently performed on the same touch sensing surface for the touch screen.

For another example, due to the above described nature of the optical sensor module for fingerprint sensing, a smartphone that integrates such an optical sensor module can be updated with improved designs, functions and integration mechanism without affecting or burdening the design or manufacturing of the LCD display screens to provide desired flexibility to device manufacturing and improvements/upgrades in product cycles while maintain the availability of newer versions of optical sensing functions to smartphones, tablets or other electronic devices using LCD display screens. Specifically, the touch sensing layers or the LCD display layers may be updated in the next product release without adding any significant hardware change for the fingerprint sensing feature using the disclosed under-screen optical sensor module. Also, improved on-screen optical sensing for fingerprint sensing or other optical sensing functions by such an optical sensor module can be added to a new product release by using a new version of the under-screen optical sensor module without requiring significant changes to the phone assembly designs, including adding additional optical sensing functions.

The above and other features of the disclosed optical sensor technology can be implemented to provide a new generation of electronic devices with improved fingerprint sensing and other sensing functions, especially for smartphones, tablets and other electronic devices with LCD display screens to provide various touch sensing operations and functions and to enhance the user experience in such devices.

The optical sensor technology disclosed herein uses the light for displaying images in a display screen that is returned from the top surface of the device display assembly for fingerprint sensing and other sensing operations. The returned light carries information of an object in touch with the top surface (e.g., a finger) and the capturing and detecting this returned light constitute part of the design considerations in implementing a particular optical sensor module located underneath the display screen. Because the top surface of the touch screen assembly is used as a fingerprint sensing area, the optical image of this touched area should be captured by an optical imaging sensor array inside the optical sensor module with a high image fidelity to the original fingerprint for robust fingerprint sensing. The optical sensor module can be designed to achieve this desired optical imaging by properly configuring optical elements for capturing and detecting the returned light.

FIGS. 22A-22B show an exemplary implementation of the optical collimator design in FIGS. 20, 21A, and 21B. The optical collimator array 2001 in this example includes an array of optical collimators 903 and an optical absorption material 905 filled between the optical collimators 903 to absorb light to reduce cross talk between different optical collimators. Each collimator 903 of the collimator array 2001 may be channels that are extended or elongated along a direction perpendicular to the display panel and lets the light be transmitted along its axis with a low loss. The collimator array 2001 is designed to reduce optical crosstalk between different optical collimators and to maintain a desired spatial resolution in the optical sensing. In some implementations, one optical collimator may correspond to only one photodetector in the photodetector array 2002. In other implementations, one optical collimator may correspond to two or more photodetectors in the photodetector array 2002. As illustrated in FIG. 22B, the axis of each collimator unit may be perpendicular to the display screen surface in some designs and may be slanted with respect to the display surface. In operation, only the light that propagates along a collimator axis carries the image information. For example, the proper incident light 82P is reflected to form light 82R. Light 82R is then diffracted by the small holes of the TFT and expanded to light 82D. The light portion 82S is transmitted into the photodiode array 2002. The light portion 82E away from the axis is absorbed by the filling material. The reflectance on the cover glass surface 431 carries the fingerprint information. Light rays 901 at an angle with respect to the collimator unit axis and thus may be blocked. A part of the reflected light, such as 901E, transmits into a corresponding optical collimator to reach the photodetector array 2002.

The optical collimator array can be made by different techniques, including, e.g., etching holes through a flat substrate, forming a light waveguide array, forming a micro lens array matching with optical filters, using coreless optical fiber bundle, or printing collimators on a transparent sheet. The desired features for such a collimator array include: (1) sufficient transmission contrast between the light component that propagates along the axis and the component that propagates off the axis so that the collimators ensures the desired spatial resolution in the optical sensing of the fingerprint pattern at the photodetector array; (2) the permitted transmission numerical aperture be sufficiently small to realize a desired high spatial resolution for the optical sensing.

Various optical collimator array designs may be used. Each optical collimator in the optical collimator array is structured to perform spatial filtering by transmitting light in directions along or close to an axis of the optical collimator while blocking light in other directions and to have a small optical transmission numerical aperture to achieve a high spatial resolution by the array of optical collimators. The small optical transmission numerical aperture also reduces the amount of the background light that enters the optical detector array. The collimator element aperture and the pitch (i.e., the distance between two nearby collimator elements) can be designed to achieve a desired spatial resolution for the optical fingerprint sensing.

Figure 23:
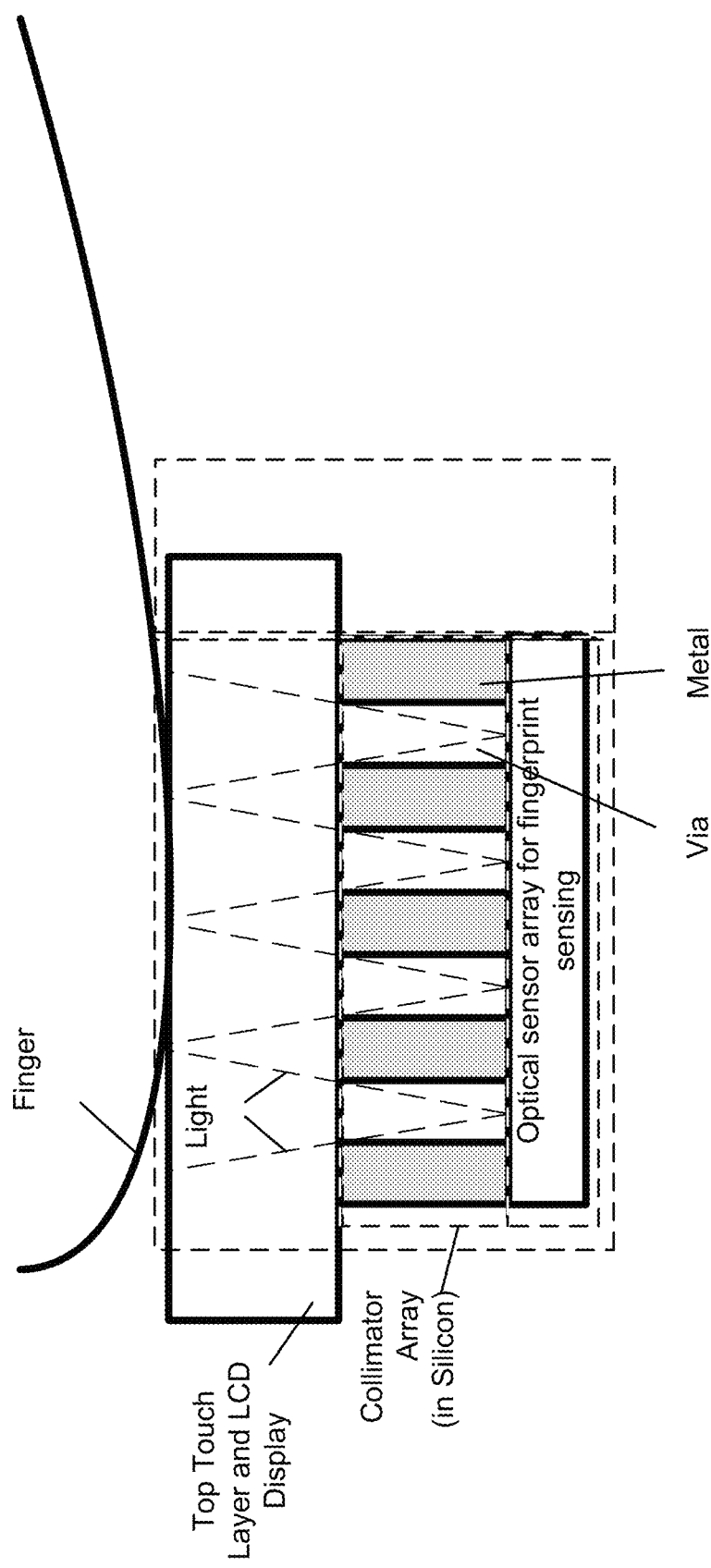
FIGS. 23 and 24 show examples of under-screen optical sensor modules with optical collimators.

FIG. 23 shows an example of a collimator design that is part of a CMOS structure by using aligned holes in two different metal layers in the CMOS structure. Each optical collimator in the array is an elongated channel along a direction that is perpendicular to the display panel in this particular example.

Figure 24:
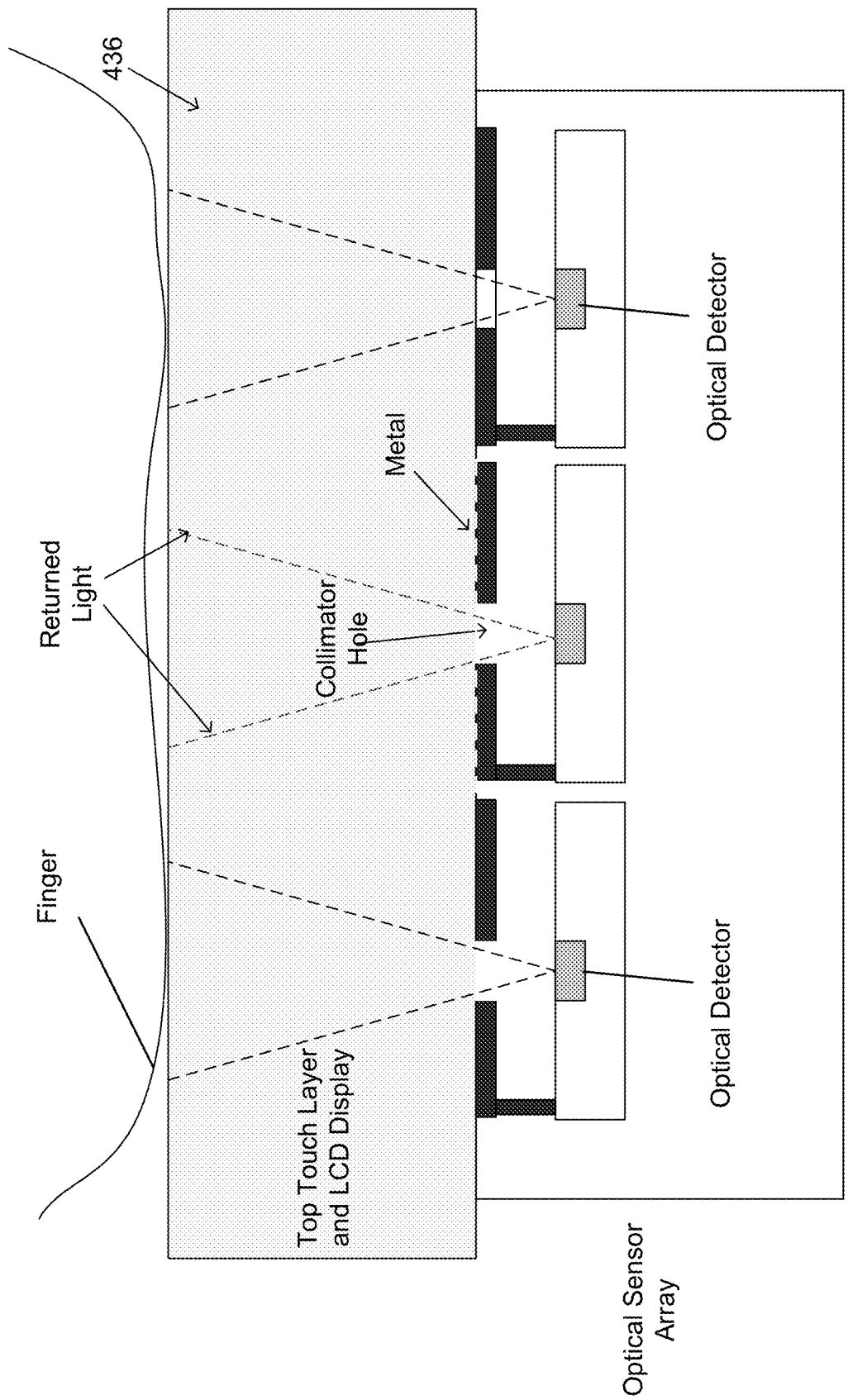

FIG. 24 shows an example of an optical fingerprint sensor module under a LCD display structure that incorporates an optical detector array and an integrated collimator array for each optical sensor pixel in capturing fingerprint information. The optical detector array includes an array of photodetectors and a collimator array is disposed over the photodetector array to include optically transparent vias as optical collimators and optically opaque metal structures between the vias as shown. Illumination light is directed to illuminate the touched portion of a finger and the light reflected off the finger is directed through the optical collimator array to reach the photodetector array which captures a part of the fingerprint image of the finger. The optical collimator array can be implemented using one or more metal layer(s) with holes or openings integrated via the CMOS process.

Such optical collimators in the under-screen optical sensor module can be structured to provide direct point to point imaging. For example, the dimensions of the optical collimator array and individual collimators can be designed to closely match the dimensions of the photodetector array and the dimensions of individual photodetectors, respectively, to achieve one to one imaging between optical collimators and photodetectors. The entire image carried by the light received by the optical sensor module can be captured by the photodetector array at individual photodetectors simultaneously without stitching.

The spatial filtering operation of the optical collimator array can advantageously reduce the amount of the background light that enters the photodetector array in the optical sensor module. In addition, one or more optical filters may be provided in the optical sensor module to filter out the background light and to reduce the amount of the background light at the photodetector array for improved optical sensing of the returned light from the fingerprint sensing area due to the illumination by emitted light from the OLED pixels. For example, the one or more optical filters can be configured, for example, as bandpass filters to allow transmission of the illumination light generated for optical sensing while blocking other light components such as the IR light in the sunlight. This optical filtering can be an effective in reducing the background light caused by sunlight when using the device outdoors. The one or more optical filters can be implemented as, for example, optical filter coatings formed on one or more interfaces along the optical path to the photodetector array in the optical sensor module or one or more discrete optical filters.

Figure 25:
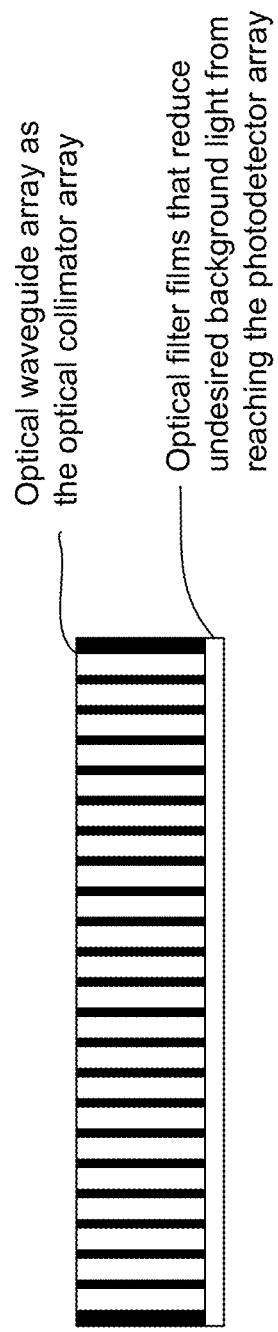
FIG. 25 shows an example an optical collimator array with optical filtering to reduce background light that reaches the photodetector array in the under-screen optical sensor module.

FIG. 25 shows an example an optical collimator array with optical filtering to reduce background light that reaches the photodetector array in the under-screen optical sensor module. This example uses an array of optical waveguides as the optical collimators and one or more optical filter films are coupled to the optical waveguide array to reduce undesired background light from reaching the photodetector array coupled to the optical waveguide array, e.g. the IR light from the sunlight while transmitting desired light in a predetermined spectral band for the probe light that is used to illuminate the finger. The optical waveguide can include a waveguide core with or without an outside waveguide cladding. The optical waveguide may also be formed by a coreless fiber bundle with different fibers where each unit collimator is a piece of fiber without a fiber core structure. When the coreless fibers are made into bundle, the filling material between the fibers may include a light absorbing material so as to increase the absorption of stray light that is not guided by the coreless fibers. The final collimator may be assembled with multiple layers of sub-collimator arrays.

The following sections provide examples of various optical collimator designs and their fabrication.

Figure 26A:
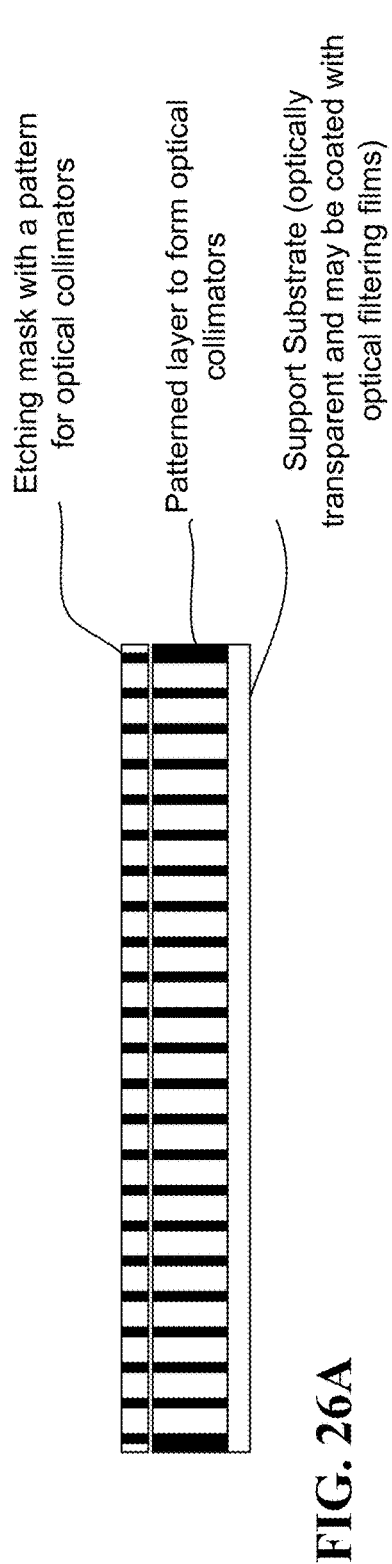
FIGS. 26A, 26B, 27 and 28 show examples of optical collimator designs for the optical sensing under the LCD display screen.
Figure 26B:
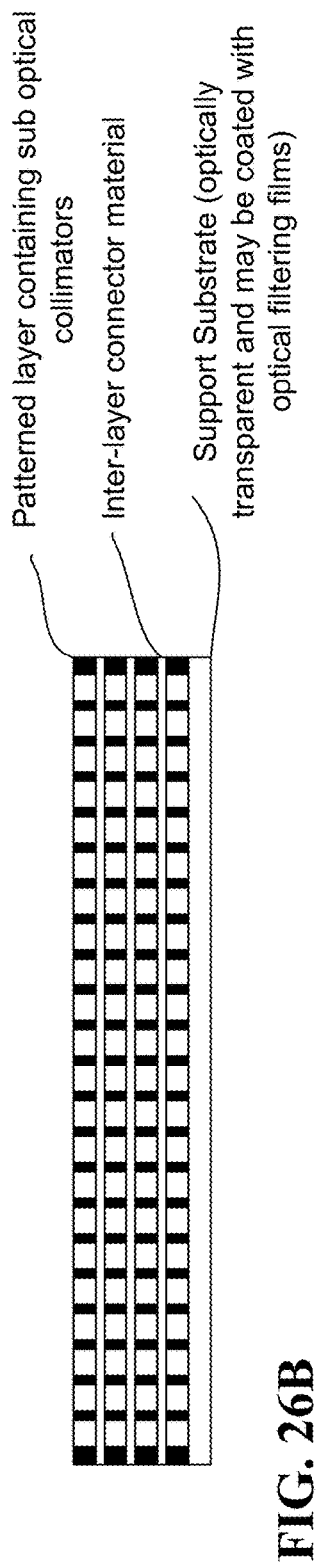

FIGS. 26A and 26B show examples of fabricating collimators by etching. In FIG. 26A, a layer of a suitable material for forming optical collimators in the collimator array is formed on or supported by a support substrate which is optically transparent. An etching mask is formed over the layer and has a pattern for etching the underlying layer to form the optical collimators. A suitable etching process is performed to form the optical collimators. The support substrate may be bound with the collimator array and may be formed from various optical transparent materials including, e.g., silicon oxide.

FIG. 26B shows an example of an optical collimator array that is assembled by stacking multiple layers of sub-collimator arrays via an inter-layer connector material which may be an adhesive, a glass, or a suitable optically transparent material. In some implementations, different layers of sub-collimator arrays may be stacked over one another without the inter-layer connector material. This stacking allows fabrication of optical collimators with desired lengths or depths along the collimator axis to achieve desired optical numerical apertures. The holes of the collimators geometrically limit the viewing angle. The transmitting numeral aperture is decided by the thickness of the collimator and the hole aperture. The holes may be filled with an optically transparent material in some applications and may be void in some designs.

In implementations, the support substrate may be coated with one or more optical filter films to reduce or eliminate background light such as the IR light from the sunlight while transmitting desired light in a predetermined spectral band for the probe light that is used to illuminate the finger.

Figure 27:
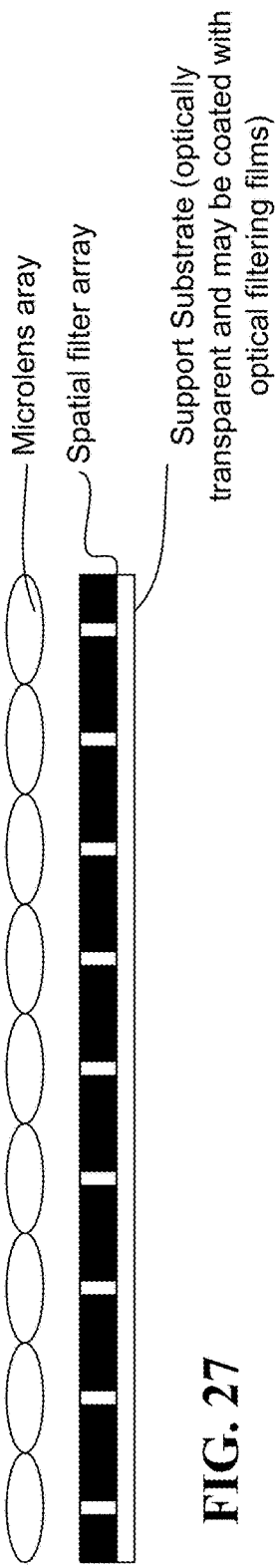

FIG. 27 shows an array of optical spatial filters coupled with micro lens array where each microlens is located with respect to a corresponding through hole of an optical spatial filter so that each unit collimator includes a micro lens and a micro spatial filter, such as a micro hole. Each micro lens is structured and positioned to focus received light to the corresponding micro spatial filter without imaging the received light. The micro hole limits the effective receiving numerical aperture. The spatial filter may be printed on an optically transparent substrate, or etched on a piece of silicon wafer. The micro lens array may be etched by MEMS processing or chemical processing. The micro lens may also be made of a gradient refractive index material, e.g., cutting a piece of gradient refractive index glass fiber to a quarter pitch of length. The focal length of the micro lenses and the diameter of the spatial filter hole can be used to control the transmitting numerical aperture of each unit. Like in other designs, the collimator board may be coated with filter films to reduce or eliminate the light band not used in the sensor such as the IR light from the sunlight.

Figure 28:
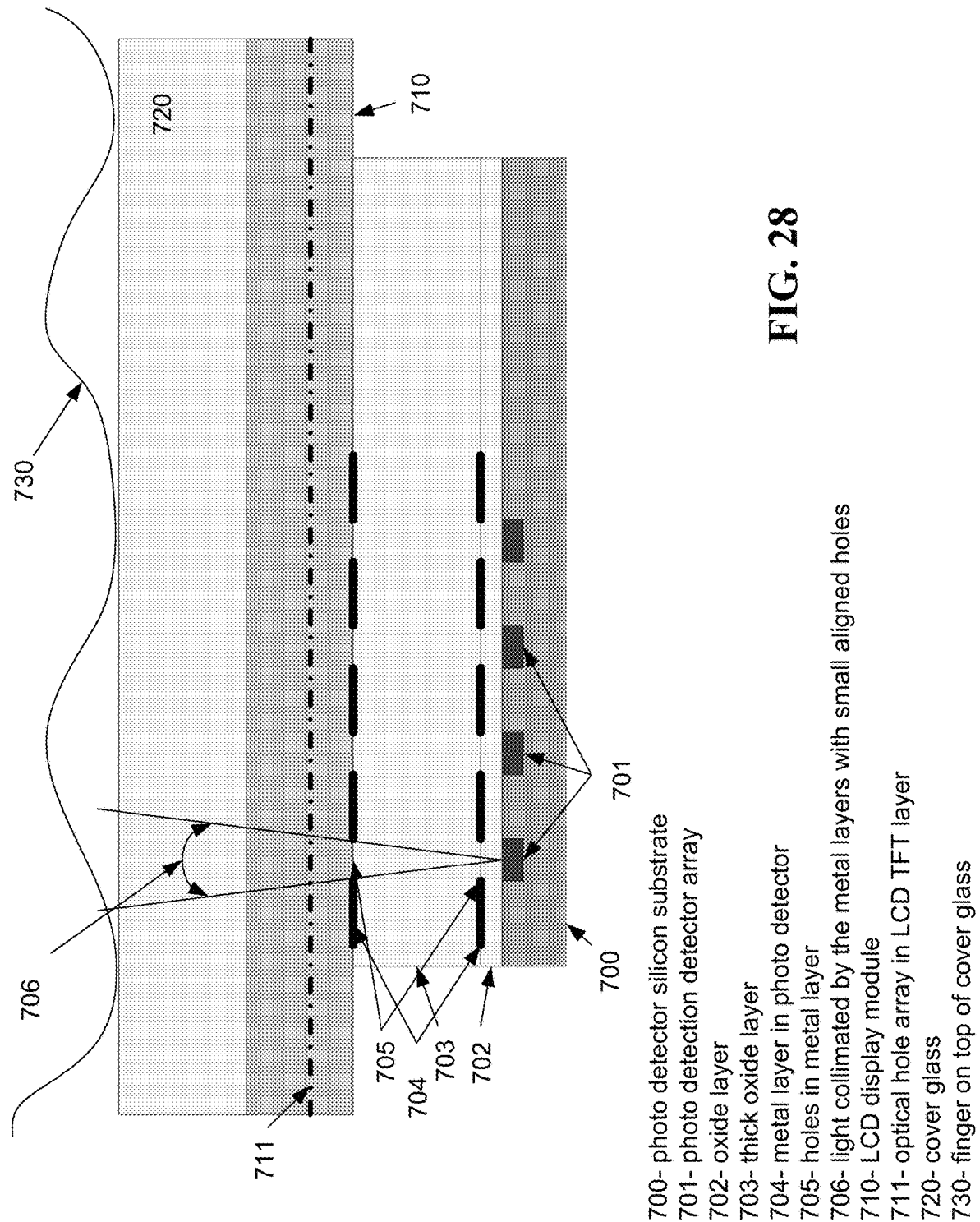

FIG. 28 shows an example of an integrated CMOS photo detection array sensor, with built-in collimation of light. The collimator is built by combing an array of aligned holes 705 in different metal layers 704 and oxide layers 702, 703 which are interleaved between metal layers to provide separation. These holes can be aligned with photo sensitive elements 701 in the optical detector array. Optical fingerprint imager is implemented with this integrated CMOS photo detection array sensor with built-in collimation of light under the LCD display module 710 and cover glass. The fingerprint of the user's finger in touch with the sensor window area of the cover glass can be imaged by detection of the light reflected off the fingerprint valley and ridges. The light from a fingerprint ridge area would be reduced, because the light is absorbed in fingerprint tissue at the ridge area while the light from the fingerprint valley area stronger by comparison. This difference in the light levels between the ridges and valleys of a fingerprint produces a fingerprint pattern at the optical detector array.

In the above optical sensor module designs based on collimators, the thickness or length of each collimator along the collimator can be designed to be large to deliver imaging light to a small area on the optical detector array or to be small to deliver imaging light to a large area on the optical detector array. When the thickness or length of each collimator along the collimator in a collimator array decreases to a certain point, e.g., tens of microns, the field of the optical view of each collimator may be relatively large to cover a patch of adjacent optical detectors on the optical detector array, e.g., an area of 1 mm by 1 mm. In some device designs, optical fingerprint sensing can be achieved by using an array of pinholes with each pinhole having a sufficiently large field of optical view to cover a patch of adjacent optical detectors in the optical detector array to achieve a high image resolution at the optical detector array in sensing a fingerprint. In comparison with a collimator design, a pinhole array can have a thinner dimension and a smaller number of pinholes to achieve a desired high imaging resolution without an imaging lens. Also, different from the imaging via optical collimators, imaging with the array of pinholes uses each pinhole as a pinhole camera to capture the image and the image reconstruction process based on the pinhole camera operation is different that by using the optical collimator array: each pinhole establishes a sub-image zone and the sub image zones by different pinholes in the array of pinholes are stitched together to construct the whole image. The image resolution by the optical sensor module with a pinhole array is related to the sensitive element size of the detector array and thus the sensing resolution can be adjusted or optimized by adjusting the detector dimensions.

A pinhole array can be relatively simple to fabricate based on various semiconductor patterning techniques or processes or other fabrication methods at relatively low costs. A pinhole array can also provide spatial filtering operation to advantageously reduce the amount of the background light that enters the photodetector array in the optical sensor module. Similar to designing the optical sensor modules with optical collimators, one or more optical filters may be provided in the optical sensor module with a pinhole array to filter out the background light and to reduce the amount of the background light at the photodetector array for improved optical sensing of the returned light from the fingerprint sensing area due to the illumination by the illumination light generated for optical sensing. For example, the one or more optical filters can be configured, for example, as bandpass filters to allow transmission of the illumination light for optical sensing while blocking other light components such as the IR light in the sunlight. This optical filtering can be an effective in reducing the background light caused by sunlight when using the device outdoors. The one or more optical filters can be implemented as, for example, optical filter coatings formed on one or more interfaces along the optical path to the photodetector array in the optical sensor module or one or more discrete optical filters.

Figure 29:
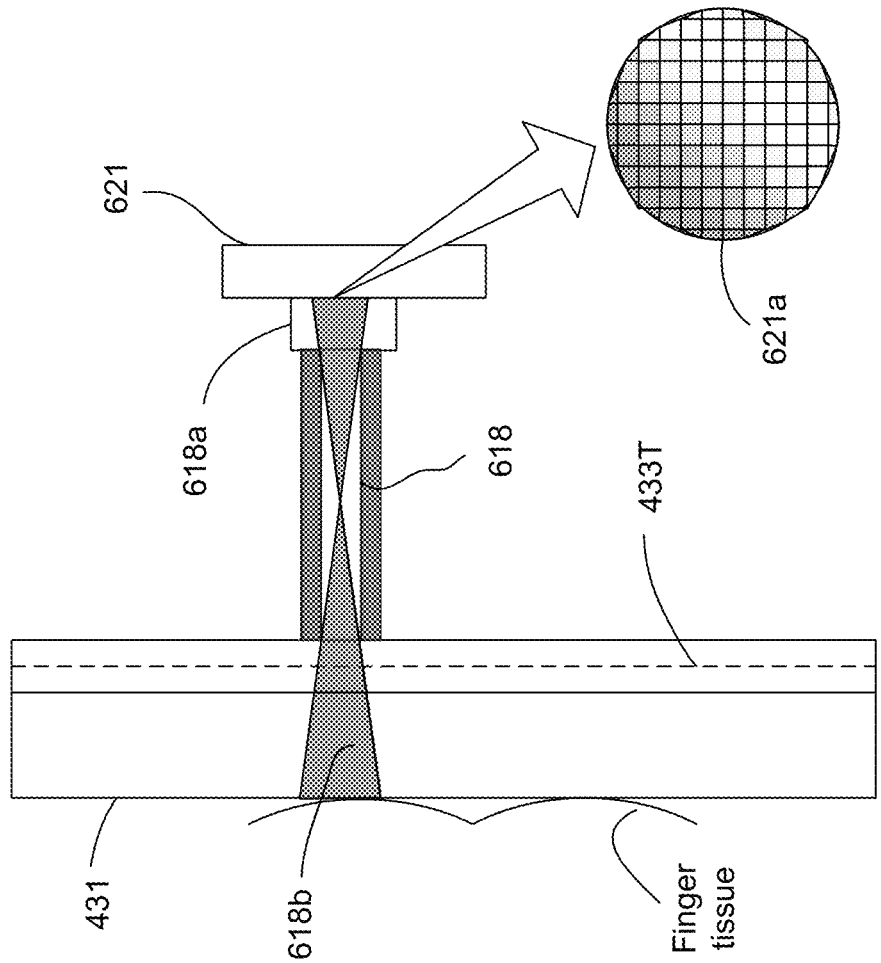
FIGS. 29, 30 and 31 illustrate improved optical imaging resolution based on a pinhole camera effect in designing the optical sensor module.

In an optical sensor module based on optical collimators, the optical imaging resolution at the optical detector array can be improved by configuring the optical collimators in a way to provide a pinhole camera effect. FIG. 29 shows an example of such a design.

In FIG. 29, a collimator unit 618 of an array of such optical collimators guides the light from the corresponding detection area unit to the photo detector array 621. The aperture of the collimator unit forms a small field of view (FOV) 618b. If the detector in the photo detector array 621 does not capture the details in each unit FOV, the imaging resolution is decided by the FOV of each collimator unit. To improve the detection resolution, the FOV of each collimator unit needs to be reduced. However, when a gap 618a is provided between each photo detector in the photo detector array 621 and the corresponding collimator 618, the small aperture of the collimator unit acts as a pinhole. This pinhole camera effect provides a higher imaging resolution in the image of each unit of FOV. When there are multiple detector elements in a unit FOV, such as shown in the insert 621a, the images details in the unit FOV can be recognized. This means that the detection resolution is improved. In implementations, such a gap can be provided in various ways, including, e.g., adding optical filter films 618a between the collimators 618 and the optical detector array 621.

With the help of the pinhole camera effect, the fill factor of the collimator board, may be optimized. For example, to detect an area of 10 mm×10 mm in size, if each unit FOV covers an area of 1 mm×1 mm, a 10×10 collimator array can be used. If in each unit FOV the detector can get 20×20 definition image, the overall detection resolution is 200× 200, or 50 microns, or 500 psi. This method can be applied for all types of collimator approaches.

Figure 30:
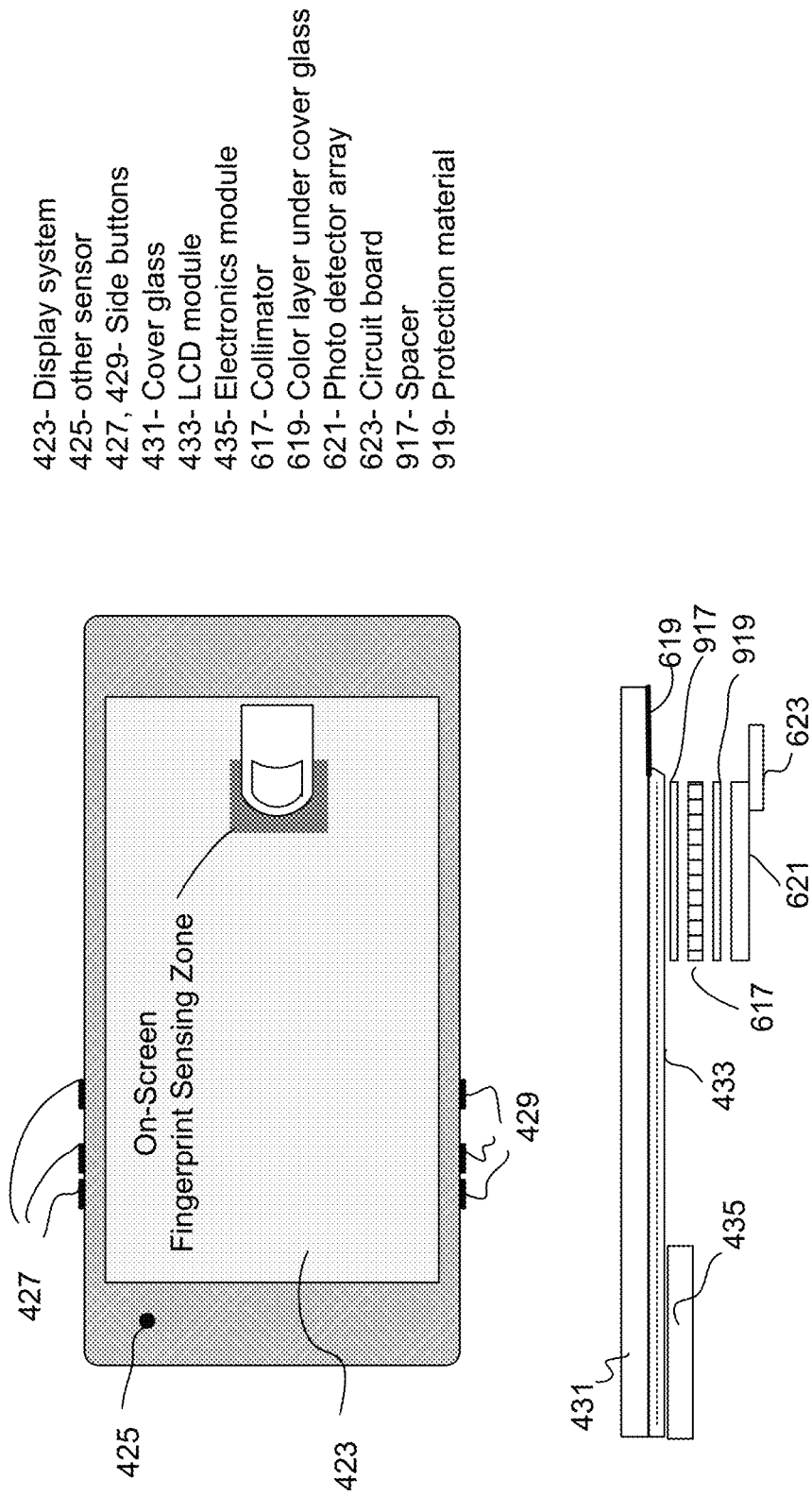

FIG. 30 shows another example for using the pinhole camera effect to improve the optical imaging resolution. In this example, the optical sensor module includes several layers: a spacer 917, a pinhole array 617 which may be an optical collimator array with a sufficiently small thickness, a protection material 919, a photo detector array 621, and a circuit board 623. The object optical distance is decided by the total material thickness from sensing surface to the pinhole plane, including the optical thickness of the display module 433, the thickness of the spacer 917, any filter coating thickness, any air gap thickness, and any glue material thickness. The image optical distance is decided by the total material thickness from the pinhole plane to the photo detector array, including the protection material thickness, any filter coating thickness, any air gaps thickness, any glue material thickness. The image magnification is decided by the image optical distance comparing with the object optical distance. The detection mode can be optimized by setting a proper magnification. For example, the magnification may be set to be less than 1, such as 0.7 or 0.5 etc. In some device designs, the spacer and the pinhole array layer may be combined into a single component. In other designs, the pinhole array and the protection layer may be combined to a single component so as to pre-define the center co-ordinates of each pinhole.

Figure 31:
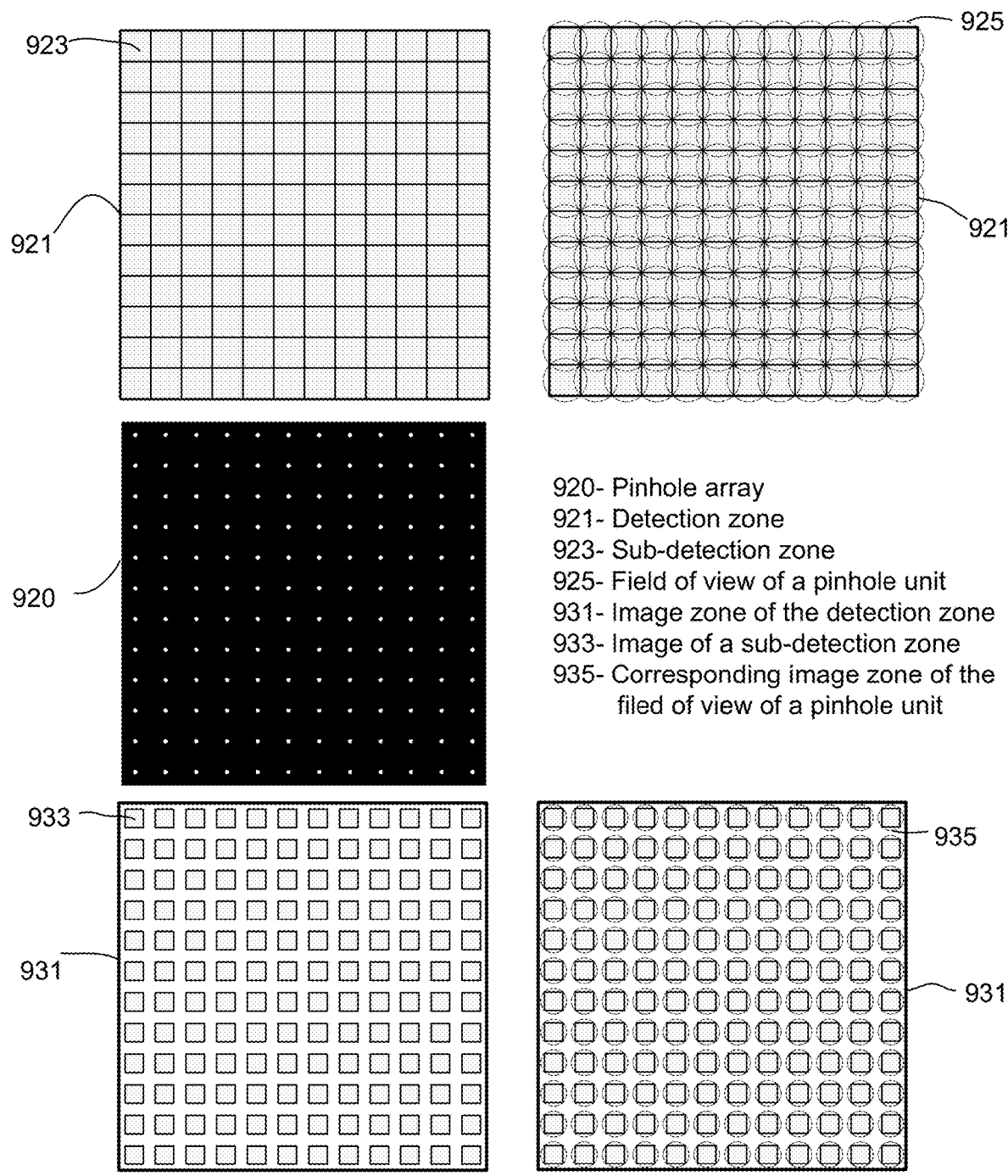

FIG. 31 shows an example of the optical imaging based on the pinhole camera effect. On the object side, the whole detection zone 921 on the LCD display panel is divided into multiple sub-detection zones 923. A pinhole array 920 is provided for imaging the detection zone 921. Each pinhole unit in the pinhole array 920 is responsible for a small field of view (FOV) 925. Each small FOV 925 covers a sub-detection zone 923. As shown in FIG. 31, each small FOV of one pinhole can overlap with small FOVs of its neighboring pinholes. On the image side, each sub-detection zone 923 in the optical detector array captures an image 933. Also shown in FIG. 31, each small FOV 925 of a pinhole has a corresponding image zone 935. The magnification of this system can be optimized so that the images of each sub-detection zone can be separately distinguished. In other words, the images of the small FOVs do not overlap each other. In this detection mode, the central coordinates of each pinhole are pre-defined and the image spot coordinates of each LCD display pixel can be pre-calibrated and this pre-calibration may be used to generate a calibration table for the calibration during the sensor operation. In this design, the image of the pinhole camera is inversed and the signal processing can recover the whole image based on the calibration table.

In the above illustrated examples for optical collimators, the direction of the optical collimators for directing light from a finger on the top of the display screen into the optical detector array for fingerprint sensing may be either perpendicular to the top touch surface of LCD display screen to collect returned probe light from the finger for fingerprint sensing, a majority of which is in a light direction perpendicular to the top touch surface. In practice, when a touched finger is dry, the image contrast in the detected images in the optical detector array by sensing such returned probe light that is largely perpendicular to the top touch surface is lower than the same image obtained from returned probe light that is at an angle with respect to the perpendicular direction of the top touch surface. This is in part because optical sensing of angled returned light spatially filters out the strong returned light from the top touch surface that is mostly perpendicular to the top touch surface. In consideration of this aspect of the optical sensing of the returned probe light from the top touch surface, the optical collimators may be oriented so that the axis of each collimator unit may be slanted with respect to the top touch surface as shown in the example in FIG. 22B.

In fabrication, however, it is more complex and costly to fabricate slanted collimators. One way to use perpendicular optical collimators as shown in FIGS. 20 and 21B while still achieving a higher contrast in the optical sensing by selectively detecting angled returned light from the top touch surface is to provide an optical deflection or diffraction device or layer between the perpendicular optical collimators and the returned light from the top touch surface prior to entering the perpendicular optical collimators. This optical deflection or diffraction device or layer can be, in some implementations, between the OLED display panel and the perpendicular optical collimators to select only returned probe light that is at some slanted angle to enter the perpendicular optical collimators for optical detection by the optical detector array on the other end of the perpendicular optical collimators while blocking or reducing the amount of the returned probe light from the top touch surface that is perpendicular to the top touch surface from entering the optical collimators. This optical deflection or diffraction device or layer may be implemented in various forms, including, e.g., an array of prisms, an optical layer with a diffraction pattern, or other devices located between the optical collimators and the display panel to select angled probe light returned from the display panel to enter the optical collimators while reducing an amount of the returned probe light that is perpendicular to the display panel and enters the optical collimators.

FIG. 32 shows an example of an optical sensor module using an optical pinhole array for optical sensing. As illustrated, a pinhole array 920a is formed between the LCD display module 433 and the optical photo detector array 621 to image the sensing area where finger 60 is pressed on onto the optical photo detector array 621.

The thickness T of the pinhole layers 920a dictates the field of view (FOV) angles. Together with the distances from the sensing surface to the pinhole array 920a and from the image plane to the pinhole array 920a, the sensing area FOVs and imaging area FOVi are defined. The image magnification is given by Di/Ds, where Di is the thickness of the optical transparent layer 919a between the pinhole array 920a and the optical detector array 621 and Ds is the thickness of the combined stack by the spacer 917, the LCD display module 433 and the top cover glass layer 431. The device parameters such as the pinhole layer thickness T, Ds, and Di can be optimized for a desired combination of FOV and image magnification. For example, the optical sensor module can be configured with desired parameters to render the neighboring FOVs of corresponding neighboring pinholes in the array 920a to properly overlap if so desired. Similarly, the neighboring FOVi can also be adjusted to be overlapped or fully separated as discrete FOVi. In an optical sensor module designed to cause neighboring FOVs to overlap each other, some of the spots on the sensing surface can have multiple image spots. This signature can be used to enhance the detection.

In the example in FIG. 32, optical filter films for reducing the background light may be formed or coated on the spacer 917, on the pinhole layers 920a, on the protection 919a, or on the display surfaces. As illustrated in the figure, when background light 937 is projected onto the finger tissues 60, short wavelength component are mostly absorbed, partial long wavelength (such as red light or infrared light) light is transmitted towards the detector 621. The optical filter films can be used to reject those long wavelength components to improve the detection of returned light signals that carry the finger information.

FIGS. 33A and 33B show an example of an optical fingerprint sensor under a LCD display panel having an optical deflection or diffraction device or layer.

As shown in FIG. 33A, each collimator 2001 in the collimator array may be an extended channel along an axis vertical or perpendicular to the display surfaces. A viewing angle adaptor optical layer 2210 is used to adjust the viewing angle of the returned probe light from the display panel and is located between the optical collimators 2001 and the LCD display panel to select angled probe light returned from the display panel to enter the optical collimators 2001 while reducing an amount of the returned probe light that is perpendicular to the display panel and enters the optical collimators 2001.

FIG. 33B shows more details of the viewing angle adaptor optical layer 3210 and the major probe light paths. For example, the viewing angle adaptor optical layer 3210 may be implemented as a diffraction pattern layer such as a prism structure 3210a. Only the returned probe light 82a and 82b from the finger with proper incident angles out of the display panel can be bent to transmit through the collimator 2001. In comparison, the returned probe light that is perpendicular to the display panel is directed by the viewing angle adaptor optical layer 2210 to be away from the original direction that is perpendicular to the display panel and thus becomes off-axis incident light to the optical collimator 2001. This reduces the amount of the returned probe light that is perpendicular to the display panel and that can enter the optical collimator 2001.

When the viewing angle is adjusted properly, the receiving light from different locations 63a and 63b of the fingerprint valley carries the fingerprint information. For example, under same illumination, light 82a may be stronger than light 82b because of the viewing angel and the fingerprint profiles of the fingertip skin. This design allows the optical sensor module to obtain some level of fingerprint shade. This arrangement improves the detection when the finger is dry.

In designing optical sensor modules under LCD display modules, various technical features or properties of LCD display modules should be considered and factored into the overall optical sensor module designs to improve the optical sensing operation. The following sections described several design examples.

One common component in various LCD display modules is a light diffuser which may a sheet that diffuses the incident light to different directions to achieve a large viewing angle and the spatial uniformity of the display. The presence of this LCD diffuser layer, however, can degrade the optical detection by the under-LCD optical sensor module.

Figure 34A:
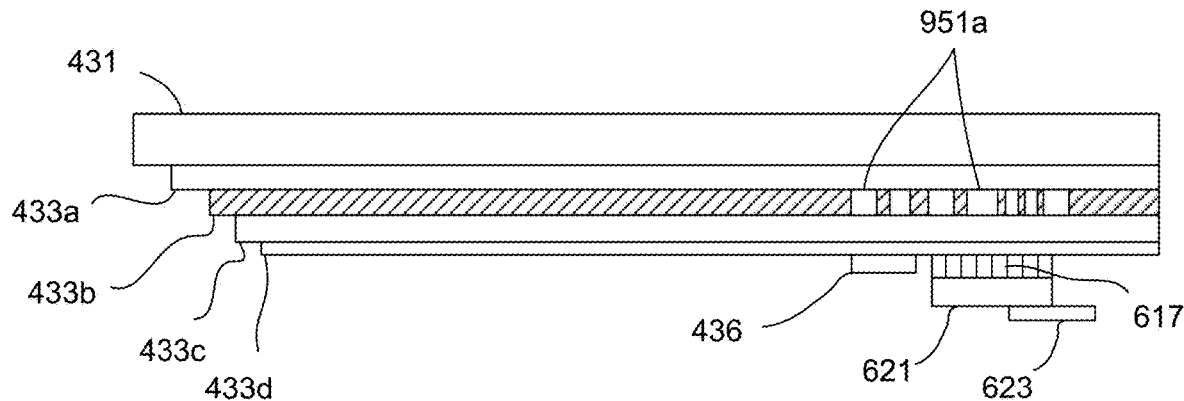
FIGS. 34A, 34B and 34C show examples of LCD diffuser designs for improved under-LCD optical sensing.
Figure 34B:
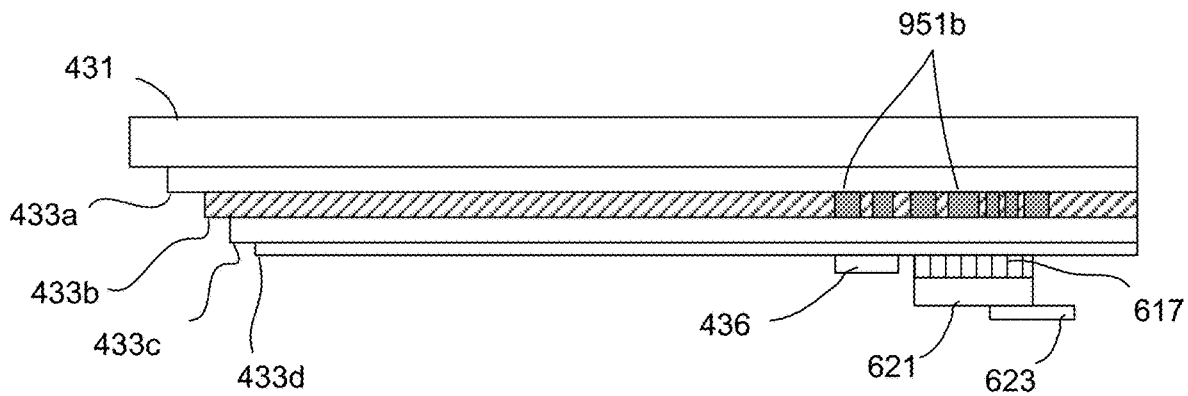

FIGS. 34A and 34B show a LCD light diffuser layer 433b located between the LCD waveguide layer 433c and other LCD layers 433a. In some LCD assemblies, the cover glass layer 431 may be separated by a distance from the underlying diffuser sheet 433b (e.g., several millimeters in some LCD devices), and the optical collimator array 617 is separated from the diffuser sheet 433b by the light waveguide board 433c (which may be sub mini-meters thick). Under this structure, the strong diffusion in the diffuser sheet 433b can significantly reduce the signal contrast in the signal light that passes through the LCD display module 433 to reach the optical detector array 621. The light diffusion at the LCD diffuser layer 433b, although desirable for display operations, degrades the fingerprint detection performance.

This undesired effect of the LCD diffuser layer 433b may be mitigated by using different techniques. Two examples are illustrated in FIGS. 34A and 34B.

FIG. 34A shows one example in which holes 951a can be made in the corresponding area or all over the diffuser sheet 433b in the LCD display module in the section of the diffuser sheet 433b above the optical sensor module to improve the transmission of the returned light from the top cover glass 431 to the optical detector array 621. The hole sizes, shapes and distribution can be selected based on the specific design needs. For example, the hole size may be larger than the probe light wave lengths so as to avoid strong diffraction. For example, a collimator unit aperture may be about 40 microns in diameter and the diffuser sheet hole size may be 5 microns, 10 microns, 30 microns, 40 microns, or 100 microns and so on. The inclusion of the holes 951a in the LCD diffuser layer 433b in this design is to establish a light path for each of the collimator unit. Each collimator unit aperture may have one or multiple holes in the diffuser sheet to provide a desired light path from the top cover glass 431 to the optical detector array 621. If the collimator unit apertures are discrete with a relatively large pitch distance (for example 1 mm or so), the holes in the diffuser sheet may be drilled with the same pitch distance. The non-uniformity in the detection can be calibrated.

FIG. 34B shows another example where the diffuser sheet can be structured to include low diffusion optical transparent spots 951b where the light diffusion is weak in the region above the optical sensor module to improve the transmission of the light to the optical sensor module. The transparent spot sizes, shapes and distribution e can be selected based on the specific design needs. For example, the hole size may be larger than the probe light wave lengths so as to avoid strong diffraction, and the spot distribution be such that each collimator unit has one or more transparent light paths to allow efficient reception of the returned light from the top cover glass 431 through the LCD display layers. If the collimator unit apertures are discrete with large pitch distance (for example 1 mm or so), the transparent spots in the diffuser sheet may be made with the same pitch distance. If the diffuser sheet is made of a rough surface material that diffracts or diffuses light, a selected material can be selectively applied to the rough surface to provide some transparent material to reduce the original optical diffusion of the rough surface. Examples for suitable materials include epoxy, wax, or oil and can effectively modify the diffusion.

For a given LCD diffuser layer, a long wavelength light source may be selected to generate the probe or illumination light so that the diffuser scattering for such light is weak so that more light can pass through the diffuser layer to reach the optical sensor module.

For another example, referring to FIGS. 35A and 35B, various LCD display modules include an optical reflector layer or film 433d in LCD below the LCD waveguide layer 433c to reflect the unused light back to the LCD layers for enhancing the display brightness. However, the presence of this optical reflector film 433d can block most of the light from reaching the optical sensor module under the LCD and thus can adversely affect the optical fingerprint sensing. This optical reflector layer can be modified in a way that maintains the desired optical reflection under the LCD waveguide layer in most locations while allowing for desired optical transmission at the location of the under-LCD optical sensor module. In some implementations, the collimator module 617 for the optical sensor under the LCD can be fixed to touch the reflector film 433d.

Figure 34C:

FIG. 34C shows another example for providing transparent light paths for guiding light from one or more illumination light sources 436 to improve the fingerprint sensing of the detection module without significant diffusion by the diffusion layer. For example, holes 969 may be selectively formed in the light diffuser film 433b to improve light transmission to the under-LCD optical fingerprint sensor. To avoid the influence of the display performance, the light path holes may be tilted to maintain some level of light diffusion function in the area of the holes 969. In addition, such holes 969 may be designed to be small, e.g., 0.3 mm or less, to further enhance diffusion of the backlighting while still providing improved optical imaging at the under-LCD optical fingerprint sensor. In implementations, the light path holes may be empty with air, may be filled with a transparent material.

In some designs, the light path holes 969 may not be limited at a certain area but may be distributed all over the light diffuser film 433b, e.g., the holes 969 may be evenly distributed in the entire film 433b. This design eliminates the undesired spatial non-uniform illumination created by the selected holes 969 in certain area but not in other areas. In some designs, the light path holes 969 may be distributed in a spatial gradient pattern so that any change in the LCD illumination caused by the holes 969 would be gradual and less visible.

FIG. 35A shows one example for modifying the optical reflector layer by including or forming light-transmitting holes in the region of the optical sensor module location in the optical reflector film to allow optical reflection for LCD display in most parts of the optical reflector film while providing the optical collimator array 617 with transparent light paths for receiving light reflected from the finger on top of the LCD. The hole sizes, shapes and distribution can be configured to meet the needs of optical sensing. For example, the hole size may be larger than the probe light wave lengths so as to avoid strong diffraction. For example, the collimator unit aperture may be around 40 microns in diameter and the diffuser sheet hole size may be 5 microns, 10 microns, 30 microns, 40 microns, or 100 microns and so on. Each collimator unit aperture may have one or multiple holes in the optical reflector layer to provide desired light paths for optical sensing. The non-uniformity in the detection can be calibrated. If the collimator unit apertures are discrete with large pitch distance (for example 1 mm or so), the holes in the reflector film may be drilled with the same pitch distance.

FIG. 35B shows another example for modifying the optical reflector layer in the LCD in which the optical reflectance of the optical reflector film may be modified to allow for some degree of optical transmission for optical sensing by the underlying optical sensor. Various commercial LCD reflector films use flexible plastic material as substrate and the optical transmittance of such plastic materials may be sufficient for transmitting sufficient light to the optical sensor module for fingerprint sensing.

In the above designs for the LCD diffuser layer and LCD reflector layer, the holes may be formed in a region where the one or more illumination light sources are located to allow sufficient transmission of the illumination light to pass through the LCD display module layers to reach the top cover glass for illuminating a finger for the optical sensing operation.

Figure 36:
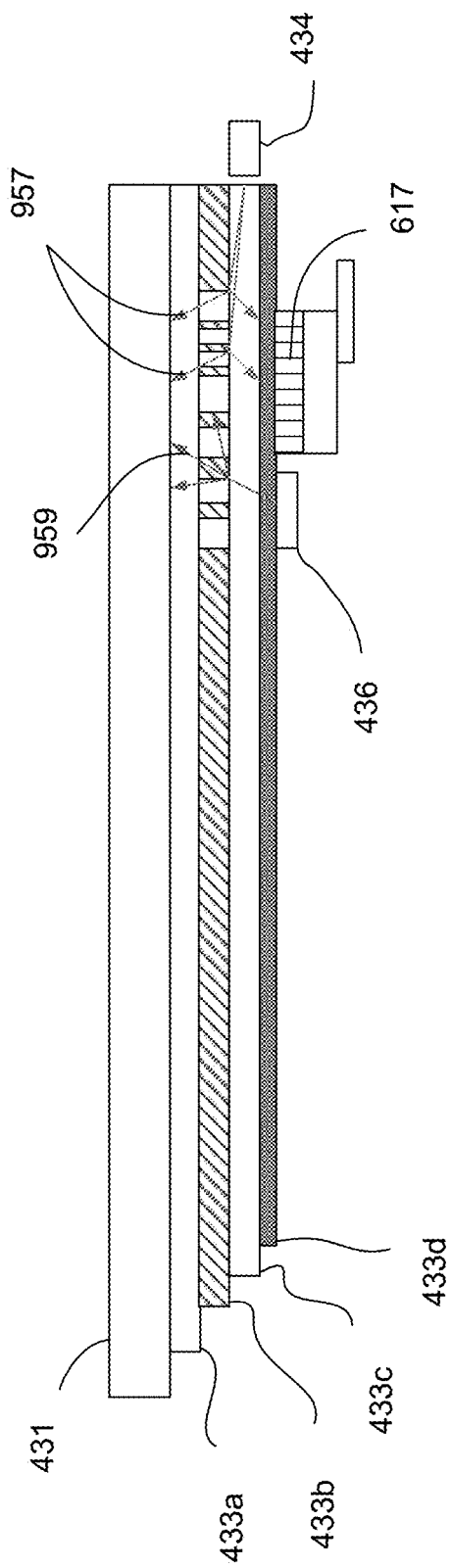
FIG. 36 shows an example of a LCD light source design for improved under-LCD optical sensing.

In the above designs, the optical sensor module is located underneath the LCD display module and thus is under the LCD waveguide layer which is designed to guide the backlighting light from the backlighting light source to the LCD display area. As shown in FIG. 36, the backlighting light from the display light sources 434 (e.g., LEDs) is guided by the waveguide 433c and is diffused by the LCD diffuser layer to leave the waveguide 433c to provide the needed backlighting for the LCD. The light may be uniformly leaked from one side surface of the waveguide 433c and is then diffused by the diffuser sheet 433b. In some LCDs, about half of the diffused light 957 may propagate towards the collimator 617 and becomes strong background light in the optical sensing detection.

One or more extra light sources 436 can be provided in connection with the optical sensor module: to illuminate the finger and to provide the light carrying the fingerprint pattern information to the optical sensor module underneath the LCD. Due to the location of the illumination light sources 436 (e.g., below the reflector film 433d next to or adjacent to the optical sensor), the light guide function of the waveguide 433c is not effective to the light from the illumination light sources 436 so that the light from the 436 can be more efficiently reach the top surface of the LCD panel for illuminating a finger.

In addition, the illumination light sources 436 can be designed to emit illumination at one or more optical wavelengths different from the LCD display illumination light wavelengths from the LCD display backlighting light sources 434. The illumination light sources 436 can be used for both fingerprint sensing and other sensing functions.

The above design for selecting the illumination light at one or more optical wavelengths that are different from the optical wavelength of the backlighting light for the LCD display may be used to reduce power consumption. Using the display backlighting light sources for the fingerprint detection requires the display backlighting light sources to be turned on for performing optical fingerprint sensing. This design consumes more power when compared to the above design where the illumination light for optical sensing is different from the backlighting light in optical wavelength in part to allow for optical sensing operation without turning on the LCD backlighting light. The above design for selecting the illumination light at one or more optical wavelengths that are different from the optical wavelength of the backlighting light for the LCD display enables flexible selection of the illumination light sources to gain additional advantages. For example, infrared light can be used as the illumination sources 436 so that the LCD diffuser layer becomes more transparent to the IR illumination light for desired higher transmission of the IR illumination light. For another example, the illumination light sources can be selected to provide multiple wavelengths for other functions such as anti-spoof liveness sensing, heartbeat sensing etc.

In designing an optical sensor module under LCD, the locations and spatial distribution of the illumination light sources 436 can be used to adjust the observing angle so as to optimize the sensing quality.

In placing an optical sensor module under a LCD module, additional optical designs may be used to enhance the delivery of the backlighting light from the waveguide layer into the LCD layers while maintaining sufficient delivery of the illumination light for optical sensing to the optical sensor module.

FIGS. 37A-37D show examples of enhancement structures that includes two or more layers of back light enhancement films such as 433px and 433py as part of the LCD layer structure shown as 433a. The backlight enhancement films 433px and 433py are formed on top of the light diffuser layer 433b.

In the example in FIG. 37A, each of the enhancement films 433px and 433py includes a polarized prism structure. The prism groove directions of the two enhancement films 433px and 433py are substantially perpendicular to each other to collectively form a pair of enhancement films to improve delivery of the illumination light to the LCD panel. However, this function of the enhancement films may adversely affect optical imaging of the under-LCD optical fingerprint sensor module 621U if not properly configured.

As shown in the examples in FIGS. 37B and 37C, the extra light source illumination direction and the detector viewing direction can be specifically configured not to be along the prism groove directions of the enhancement films 433px and 433py to reduce the adverse imaging impact of the enhancement films for optical fingerprint sensing. This design is to get a clear image without punch holes in the enhancement films. The viewing angle $\phi 1$ and the illumination angle $\phi 2$ should be adjusted according to the design of the enhancement films.

The example in FIG. 37D shows a particular design of the collimator unit 617U and a photodetector array unit 621U. The collimator unit 617U is used to provide an imaging function that is realized by a micro lens, pinholes or a combination of a micro lens and pinholes. A larger sensing area at the photodetector array unit 621U can be realized by optimizing the single detection unit design or by using multiple detection units.

Figure 38:
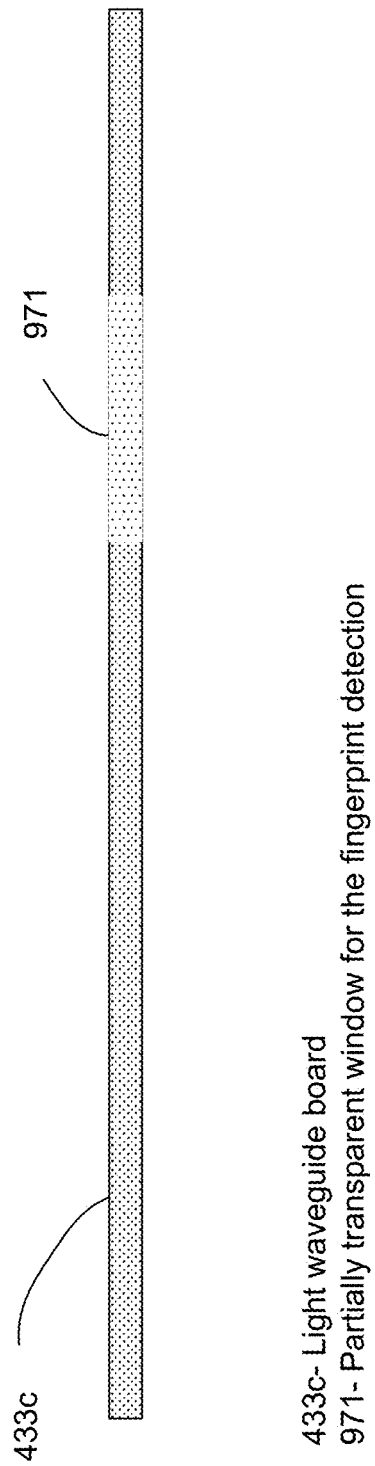
FIG. 38 shows an example of a LCD waveguide design for improved under-LCD optical sensing.

FIG. 38 shows an example of a light waveguide layer in the LCD module to include a partially transparent section in the detection light paths to allow for improve optical transmission of the illumination light for optical sensing to pass through the waveguide layer.

Figure 39A:
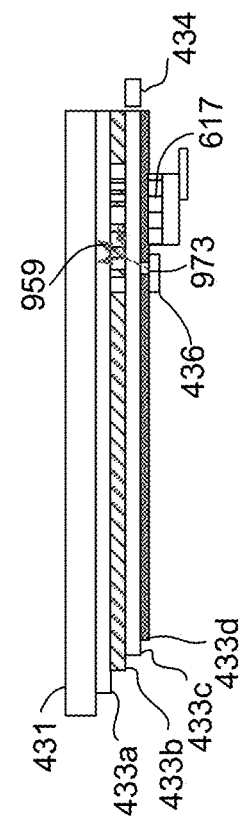
FIGS. 39A-39C show examples of LCD backlighting light source and illumination light source for improved under-LCD optical sensing.
Figure 39C:
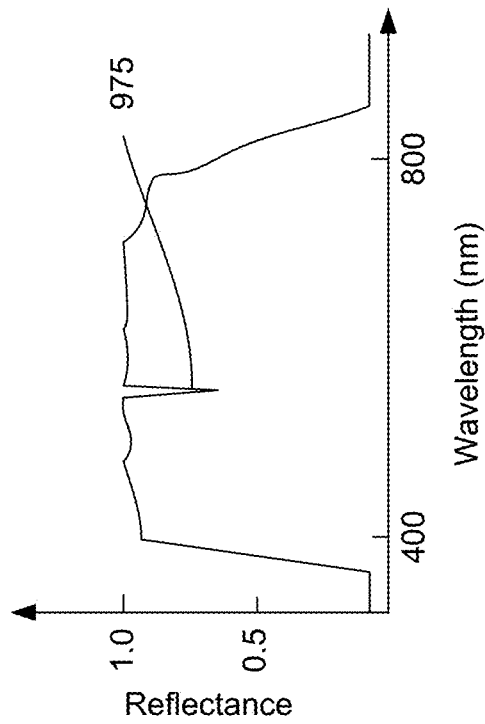
Figure 39B:
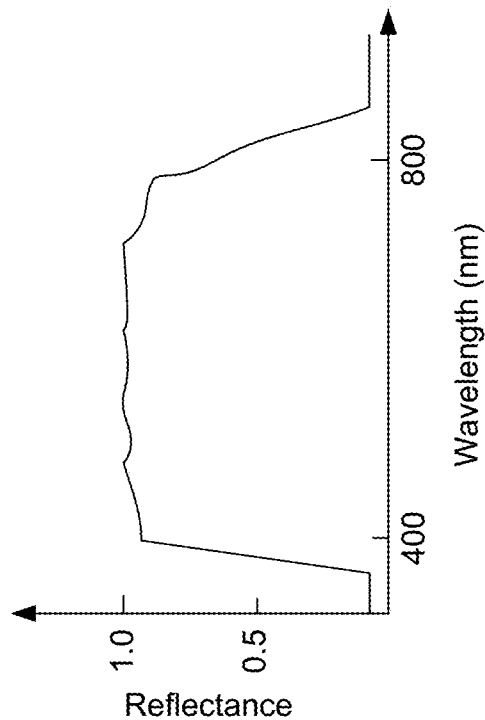

FIGS. 39A-39C show examples for designing an illumination light source for the optical sensing in an optical sensor module under the LCD display module. In a LCD display module, the optical reflector layer enhances the LCD display brightness by recycling unused backlighting light back to the LCD layers. In this regard, a defect in the optical reflectivity along the optical reflector film, e.g., a mechanical defect in the reflector film, can cause a visible change in the brightness of the LCD display and thus is undesirable. FIGS. 39A-39C illustrate design features for reducing the adverse effect of defects in the reflector layer or film.

As shown in FIG. 39A, micro holes 973 can be provided in the reflector layer 433d at the location of the illumination light sources 436 for the visible light component in the illumination light. This visible light component is used to provide illumination in a limited area of the display to show essential text or sign information without turning on the display back light.

As shown in FIG. 39B, another solution is to select the illumination light source wavelengths to be out of the reflector film's working band which is generally in the visible band. The illumination light sources 436 for optical sensing may be outside the reflection spectral range of the reflector film, e.g., short wavelength range below 400 nm (e.g., 380 nm) or long wavelength range beyond the visible red range (e.g., 780 nm, 900 nm, 940 nm, etc.) so that the illumination light can pass through the reflector film or layer without the need to form holes in the reflector film.

FIG. 39C shows yet another design solution that designs the reflector film to include a narrow band transmission window 975 for transmitting the illumination light for optical detection. For example, this narrow transparent or transmission window in the reflector film may be between 525 nm and 535 nm.

Portable devices such as mobile phones or other devices or systems based on the optical sensing disclosed in this document can be configured to provide additional operation features.

For example, the LCD display panel can be controlled to provide a local flash mode to illuminate the fingerprint sensing area by operating selected LCD display pixels underneath the sensing area. This can be provided in an optical sensor module under the LCD display panel, e.g., FIGS. 4A and 4B based on an optical imaging design or FIGS. 21A and 21B based on optical imaging via an optical collimator array. In the event of acquiring a fingerprint image, the LCD display pixels in the sensing window area and the illumination light sources can be turned on momentarily to produce high intensity illumination for optical sensing of a fingerprint, and, at the same time, the photo detection sensor array 621 is turned on to capture the fingerprint image in sync with the turning on of the illumination light. The time to turn on the illumination light can be relatively short but the emission intensity can be set to be high. For this reason, this mode for optical fingerprint sensing is a flash mode that enable the photo detector sensor array 621 to detect a larger amount of light to improve the image sensing performance.

The optical sensors for sensing optical fingerprints disclosed above can be used to capture high quality images of fingerprints to enable discrimination of small changes in captured fingerprints that are captured at different times. Notably, when a person presses a finger on the device, the contact with the top touch surface over the display screen may subject to changes due to changes in the pressing force. When the finger touches the sensing zone on the cover glass, changes in the touching force may cause several detectable changes at the optical detector array: (1) fingerprint deforming, (2) a change in the contacting area, (3) fingerprint ridge widening, and (4) a change in the blood flow dynamics at the pressed area. Those changes can be optically captured and can be used to calculate the corresponding changes in the touch force. The touch force sensing adds more functions to the fingerprint sensing.

Figure 40:
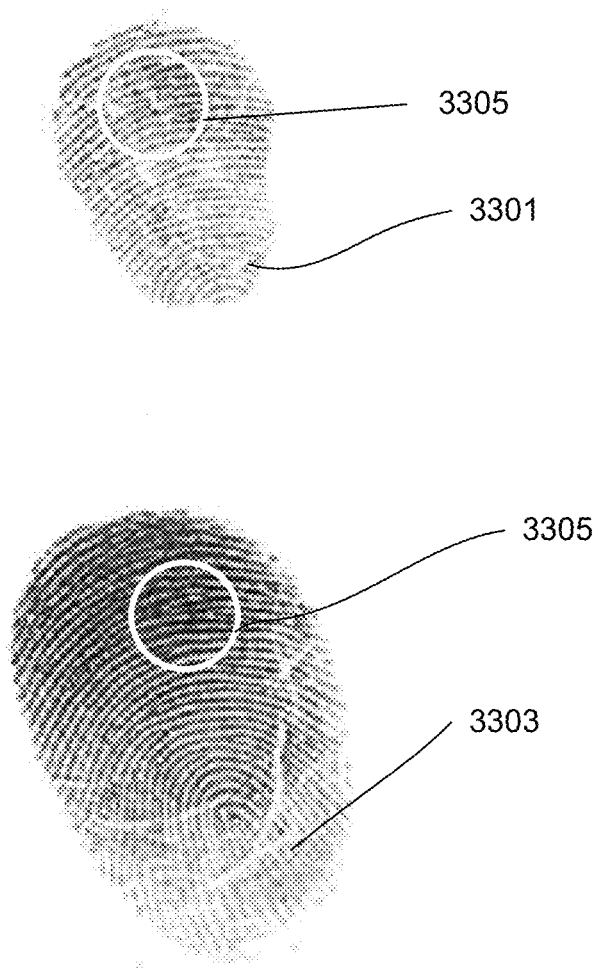
FIG. 40 shows two different fingerprint patterns of the same finger under different press forces: the lightly pressed fingerprint and the heavily pressed fingerprint.

Referring to FIG. 40, the contact profile area increases with an increase in the press force, meanwhile the ridge-print expands with the increase in the press force. Conversely, the contact profile area decreases with a decrease in the press force, meanwhile the ridge-print contracts or shrinks with the decrease in the press force. FIG. 40 shows two different fingerprint patterns of the same finger under different press forces: the lightly pressed fingerprint 2301 and the heavily pressed fingerprint 3303. The returned probe light from a selected integration zone 3305 of the fingerprint on the touch surface can be captured by a portion of the optical sensors on the optical detector array that correspond to the selected integration zone 3305 on the touch surface. The detected signals from those optical sensors are analyzed to extract useful information as further explained below.

When a finger touches the sensor surface, the finger tissues absorb the light power thus the receiving power integrated over the photo diode array is reduced. Especially in the case of total inner reflection mode that does not sense the low refractive index materials (water, sweat etc.), the sensor can be used to detect whether a finger touches the sensor or something else touches the sensor accidentally by analyzing the receiving power change trend. Based on this sensing process, the sensor can decide whether a touch is a real fingerprint touch and thus can detect whether to wake up the mobile device based on whether the touch is a real finger press. Because the detection is based on integration power detection, the light source for optical fingerprint sensing at a power saving mode.

In the detailed fingerprint map, when the press force increases, the fingerprint ridges expand, and more light is absorbed at the touch interface by the expanded fingerprint ridges. Therefore, within a relatively small observing zone 3305, the integrated received light power change reflects the changes in the press force. Based on this, the press force can be detected.

Accordingly, by analyzing the integrated received probe light power change within a small zone, it is possible to monitor time-domain evolution of the fingerprint ridge pattern deformation. This information on the time-domain evolution of the fingerprint ridge pattern deformation can then be used to determine the time-domain evolution of the press force on the finger. In applications, the time-domain evolution of the press force by the finger of a person can be used to determine the dynamics of the user's interaction by the touch of the finger, including determining whether a person is pressing down on the touch surface or removing a pressed finger away from the touch surface. Those user interaction dynamics can be used to trigger certain operations of the mobile device or operations of certain apps on the mobile device. For example, the time-domain evolution of the press force by the finger of a person can be used to determine whether a touch by a person is an intended touch to operate the mobile device or an unintended touch by accident and, based on such determination, the mobile device control system can determine whether or not to wake up the mobile device in a sleep mode.

In addition, under different press forces, a finger of a living person in contact with the touch surface can exhibit different characteristics in the optical extinction ratio obtained at two different probe light wavelengths as explained with respect FIGS. 14 and 15. Referring back to FIG. 40, the lightly pressed fingerprint 3301 may not significantly restrict the flow of the blood into the pressed portion of the finger and thus produces an optical extinction ratio obtained at two different probe light wavelengths that indicates a living person tissue. When the person presses the finger hard to produce the heavily pressed fingerprint 3303, the blood flow to the pressed finger portion may be severely reduced and, accordingly, the corresponding optical extinction ratio obtained at two different probe light wavelengths would be different from that of the lightly pressed fingerprint 3301. Therefore, the optical extinction ratios obtained at two different probe light wavelengths vary under different press forces and different blood flow conditions. Such variation is different from the optical extinction ratios obtained at two different probe light wavelengths from pressing with different forces of a fake fingerprint pattern of a man-made material.

Therefore, the optical extinction ratios obtained at two different probe light wavelengths can also be used to determine whether a touch is by a user's finger or something else. This determination can also be used to determine whether to wake up the mobile device in a sleep mode.

For yet another example, the disclosed optical sensor technology can be used to monitor the natural motions that a live person's finger tends to behave due to the person's natural movement or motion (either intended or unintended) or pulsing when the blood flows through the person's body in connection with the heartbeat. The wake-up operation or user authentication can be based on the combination of the both the optical sensing of the fingerprint pattern and the positive determination of the presence of a live person to enhance the access control. For yet another example, the optical sensor module may include a sensing function for measuring a glucose level or a degree of oxygen saturation based on optical sensing in the returned light from a finger or palm. As yet another example, as a person touches the display screen, a change in the touching force can be reflected in one or more ways, including fingerprint pattern deforming, a change in the contacting area between the finger and the screen surface, fingerprint ridge widening, or a blood flow dynamics change. Those and other changes can be measured by optical sensing based on the disclosed optical sensor technology and can be used to calculate the touch force. This touch force sensing can be used to add more functions to the optical sensor module beyond the fingerprint sensing.

Figure 42:
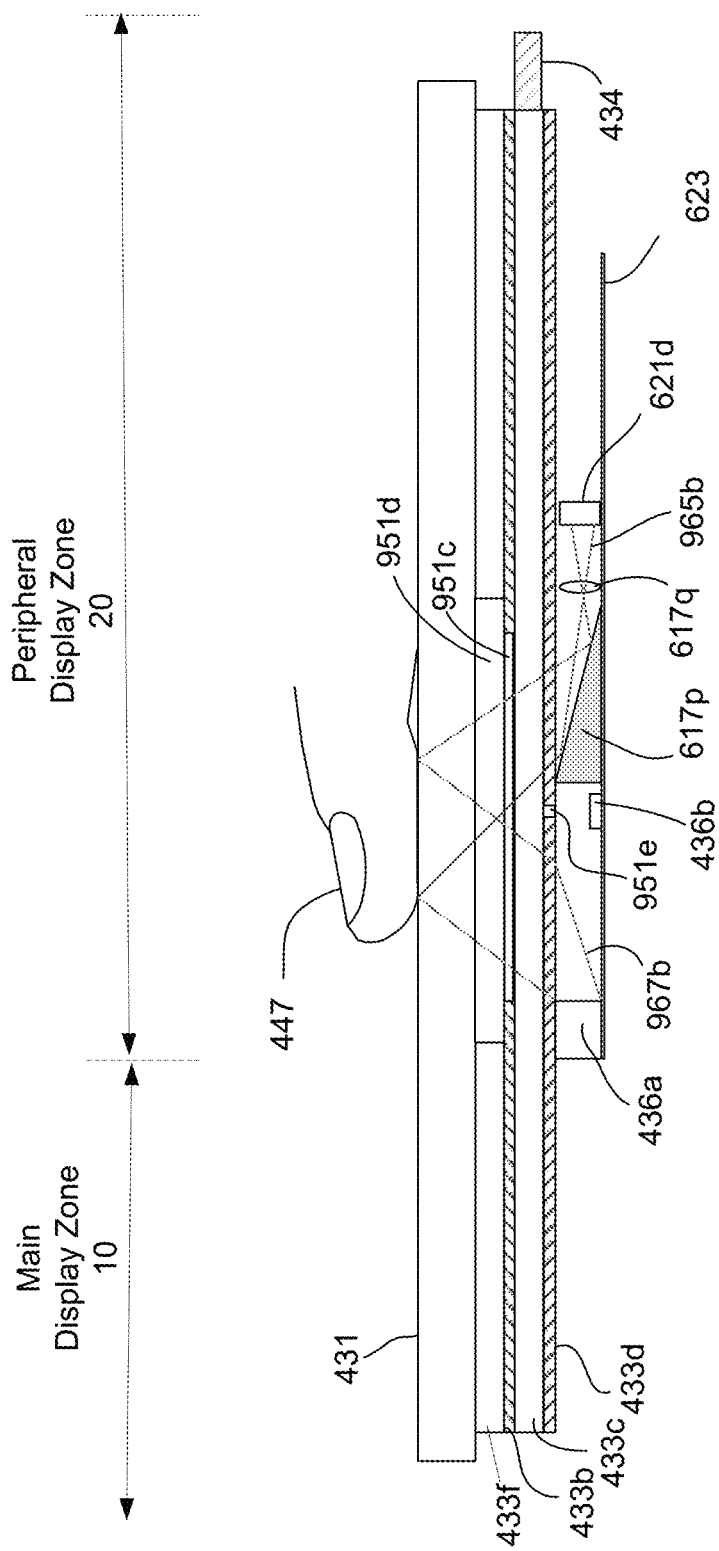

The features in connection with the under screen optical sensing described above in connection with FIGS. 3A-40 can be implemented to devices having a 2-zone display with both a main display zone and a peripheral display zone as well devices having a single-zone display without the peripheral display zone. FIGS. 41A, 41B and 42 show examples of specific implementations of an optical sensor module placed under an LCD display for a device having a LCD display module to provide the main and peripheral display zones in the same LCD panel.

FIG. 41A shows an example for placing an under-LCD optical sensor module under the LCD module within the peripheral display zone. For optical fingerprint sensing, one or more light sources 436*a* are placed under the LCD module 433 within the peripheral display zone 20 to send out a probe light beam 967*a* to transmit through the LCD module 433 and the top transparent layer 431 to reach the top sensing surface in the peripheral display zone 20 for optical sensing of a fingerprint or other properties. The probe light beam 967*a* may be a collimated beam. In operation, the probe light beam 967*a* at or near the top sensing surface interacts with a finger 447 and the reflected and/or scattered probe light caused by the finger 447 are directed back into the top transparent layer 431 as a probe signal light beam 965*a* that carries the fingerprint information and other information on the finger, e.g. a fingerprint pattern or map, the blood flow and the heartbeat etc. In this example, the design of the receiving optics to collect and route the probe signal light beam 965*a* from the top transparent layer 431 to the optical detector array 621*b* is free of an optical lens. Because the probe signal light beam 965*a* comes from the reflection of the cover glass surface of the top transparent layer 431, the fingerprint absorption map or pattern is added onto the probe signal light beam 965*a* and can be detected by the photo detector array 621*b*. The photo detector array 621*b* is oriented to have its detection surface parallel to the cover glass surface of the top transparent layer 431 and other layers. This arrangement forms a lens-less imaging projection configuration where the fingerprint map is projected onto the detector array 621*b* with a magnification ratio in 2 dimensions. The optical distortion tends to be low for probe light rays at different incident angles to the detector array 621*b* and the detected image contrast tends to be high.

FIG. 41B shows another example of a lens-less imaging projection configuration by placing an under-LCD optical sensor module under the LCD module within the peripheral display zone. Different from the design in FIG. 41A, the design in FIG. 41B orients the photo detector array 621*c* at an angle with respect to the cover glass surface of the top transparent layer 431 and other layers. This slanting orientation of the photo detector array 621*c* causes the image carried by the returned probe signal light beam 965*a* to be compressed in the direction along the surface of the photo detection array such that the dimension of the photo detector array pixels along this direction can is reduced accordingly to reduce overall cost of the photo detector array 621*c* in comparison to the photo detector array 621*b* with larger detector pixels or dimensions.

The above lens-less imaging projection configurations for an under-LCD optical sensor module in FIGS. 41A and 41B may also be used for an optical sensor module placed under a single-zone LCD panel. FIG. 4B shows an example of using this slanting orientation of the photo detector array 702 under a single-zone LCD panel.

Referring to the optical sensor module designs in FIGS. 6B through 11, the receiving optics of the under-LCD optical sensor module can also include one or more imaging lenses for optical sensing. FIG. 42 shows an example for placing an under-LCD optical sensor module under the LCD module within the peripheral display zone in a micro camera configuration where a lens is included as part of the receiving optics. The photo detector array 621*d* in this example is placed so that its detector array surface is perpendicular to or at an angle with respect to the cover glass surface of the top transparent layer 431 and other layers. A mirror 617*p* is placed in the optical path of the returned probe signal light beam 965*b* caused by the probe light beam 967*b* from the probe light source 436*b* under the LCD module to redirect the returned probe signal light beam 965*b* to be parallel to or at a small angle with respect to the direction parallel to the cover glass surface of the top transparent layer 431 and other layers. A lens 617*q* is placed in the optical path of the reflected beam from the mirror 617*p* and projects the reflected beam from the mirror 61'7*p* onto the photo detector array 621*d* along the cover glass surface of the top transparent layer 431 and other layers. In this micro camera design, the lens 617*q* produces a reduced optical image of the fingerprint pattern with a higher optical intensity, this gain of the image lens 617*q* permits the overall level of the probe light power to be reduced or improve the signal to noise performance in the optical sensing. In addition, because the lens 617*q* produces a reduced optical image of the fingerprint pattern at the photo detector array 621*d*, the micro camera can be implemented by using a small-size photo detector array as the photo detector array 621*d*. This reduces the cost of the photo detector array 621*d*. Furthermore, in this design, due to the presence of the mirror 617 to change the direction the received probe beam to be along the cover glass surface of the top transparent layer 431 and other layers, the spacing needed along the beam propagation direction due to the imaging operation of the imaging lens 617*q* can be accommodated since the needed space is along the cover glass surface of the top transparent layer 431 and other layers rather than perpendicular to the cover glass surface of the top transparent layer 431 and other layers. This optical layout with the imaging lens 617*q* can be used to keep the thickness or the dimension of the device in the direction perpendicular to the cover glass surface of the top transparent layer 431 and other layers to be small without compromising the proper imaging condition of the imaging lens 617*q*. The optics designs for the under-LCD optical sensor modules shown in FIGS. 6B through 11 similarly can maintain relatively small thickness in the direction perpendicular to the display screen.

Electronic devices with displays are often used in bright surroundings with varying levels of environmental or background light caused by natural light (e.g., natural day light from the sun) or by illumination lights such as in a well-lit office facility or stadium. Such environmental or background light can adversely impact the detection by the under-LCD optical sensor modules and should be suppressed. As mentioned above, background reduction techniques may be provided in an under-screen optical sensor module by performing certain controls and signal processing such as the two examples shown in FIGS. 12 and 13. In addition, one or more additional optical design features may be added to the above disclosed optical sensor module designs to reduce the background light based on background light filtering or adding extra illumination light sources. The different background light reduction techniques based on operation control/signal processing, optical filtering and adding extra illumination light sources can be combined in various ways in implementations.

In devices with LCD displays, one or more probe light sources are provided to produce the probe light for the under-LCD optical sensor modules and such probe light sources are separated from a backlighting light source for displaying images by the LCD display such as the backlighting light module 434 or the designated peripheral display zone illumination module 436*b* or 436*c* to illuminate the peripheral display zone 20. Therefore, the optical probe power for optical sensing can be independently controlled from the LCD illumination to provide sufficient illumination for optical sensing to improve the optical detection signal to noise ratio and to offset the environmental light influence. For example, the one or more probe light sources can be flashed with high output power for a short time during the fingerprint sensing so as to obtain optimized detection. For example, the one or more probe light sources can be modulated to provide improved optical sensing performance without affecting the display function. In addition, the one or more probe light sources can provide flexibility in the determination of whether a detected finger is a live finger to prevent malicious attempt by bypassing the fingerprint detection with a fake fingerprint. For example, multiple probe light sources may be provided to include light sources with sufficiently different optical wavelengths at which a finger exhibits different optical signatures for live finger detection, such as using green LEDs and near IR LEDs for the live finger detection as explained with reference to FIGS. 14 and 15 where finger tissues absorb the green light strongly so that the finger image manifests a desired large brightness gradient and the near IR light illuminates all through the finger so that the finger image brightness appears more uniform.

The optical filtering technique for reducing the background light can be implemented in various optical sensor module designs disclosed in this document. While the general goal of inserting optical filters in the optical path of the optical sensor module is to reject the environment light wavelengths, such as near IR and partial of the red light and other undesired wavelengths, the specific implementation of such optical filters can vary based on the specific needs of each application. Such optical filters can be formed by forming optical filter coatings on selected surfaces of the optical parts in the optical path leading to the optical detector array, including, e.g., the display bottom surface, surfaces of other optical components such as optical prisms, the upper sensor surface of the optical detector array, etc. For example, human fingers absorb most of the energy of the wavelengths under a certain wavelength (e.g., around ~580 nm), if the optical filters are designed to reject the light in the wavelengths from this wavelength around ~580 nm to infrared, the undesired environment light influence can be greatly reduced.

Figure 43:
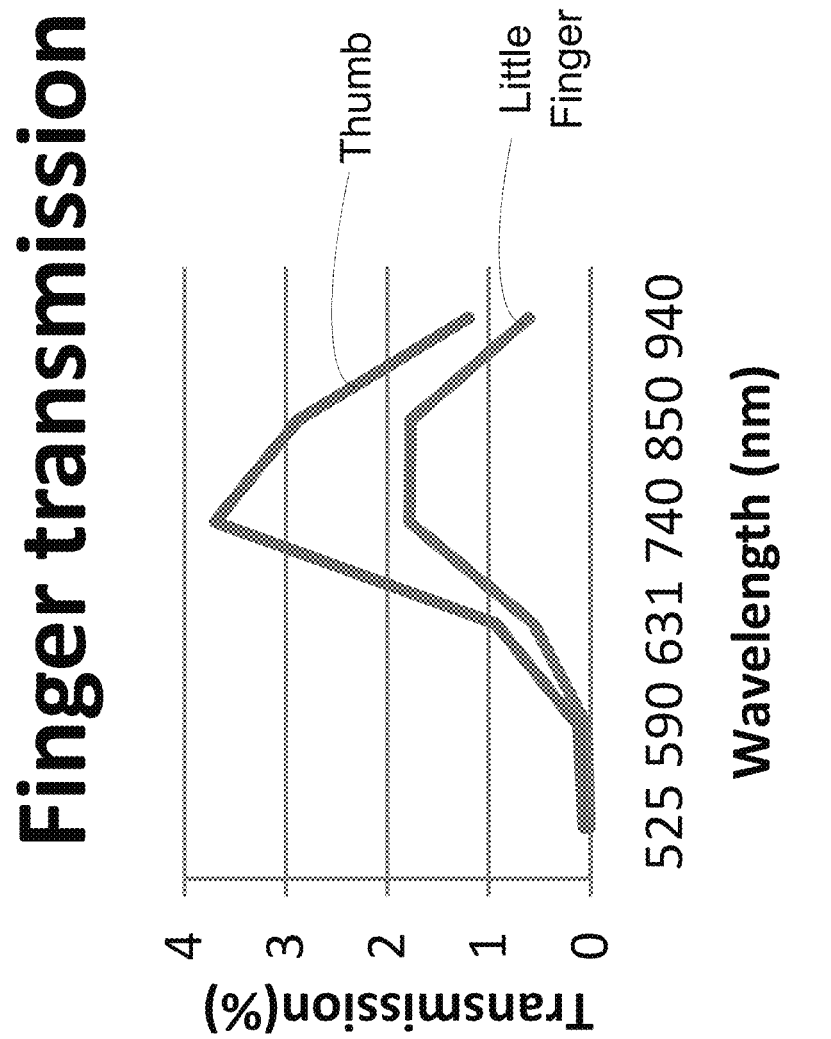
FIG. 43 shows an example of the optical transmission spectral profiles of a typical human thumb and litter finger at several different optical wavelengths from around 525 nm to around 940 nm.

FIG. 43 shows an example of the optical transmission spectral profiles of a typical human thumb and litter finger at several different optical wavelengths from around 525 nm to around 940 nm. For short wavelengths, such as wavelengths less than 610 nm, less than 0.5% of the environmental light may pass through the finger. Light at longer wavelengths such as red light and near IR light have higher transmission. The transmission of the environmental light through a finger goes to a wide range of directions due to scattering by the finger tissues and thus can mix with the signal light to be detected by the under-screen optical sensor module. When operated under the sunlight, the undesired environmental light from the sunlight can be handled carefully due to the high optical power of the sunlight so as to reduce or minimize the adverse impact to the optical fingerprint sensor performance.

Figure 44:
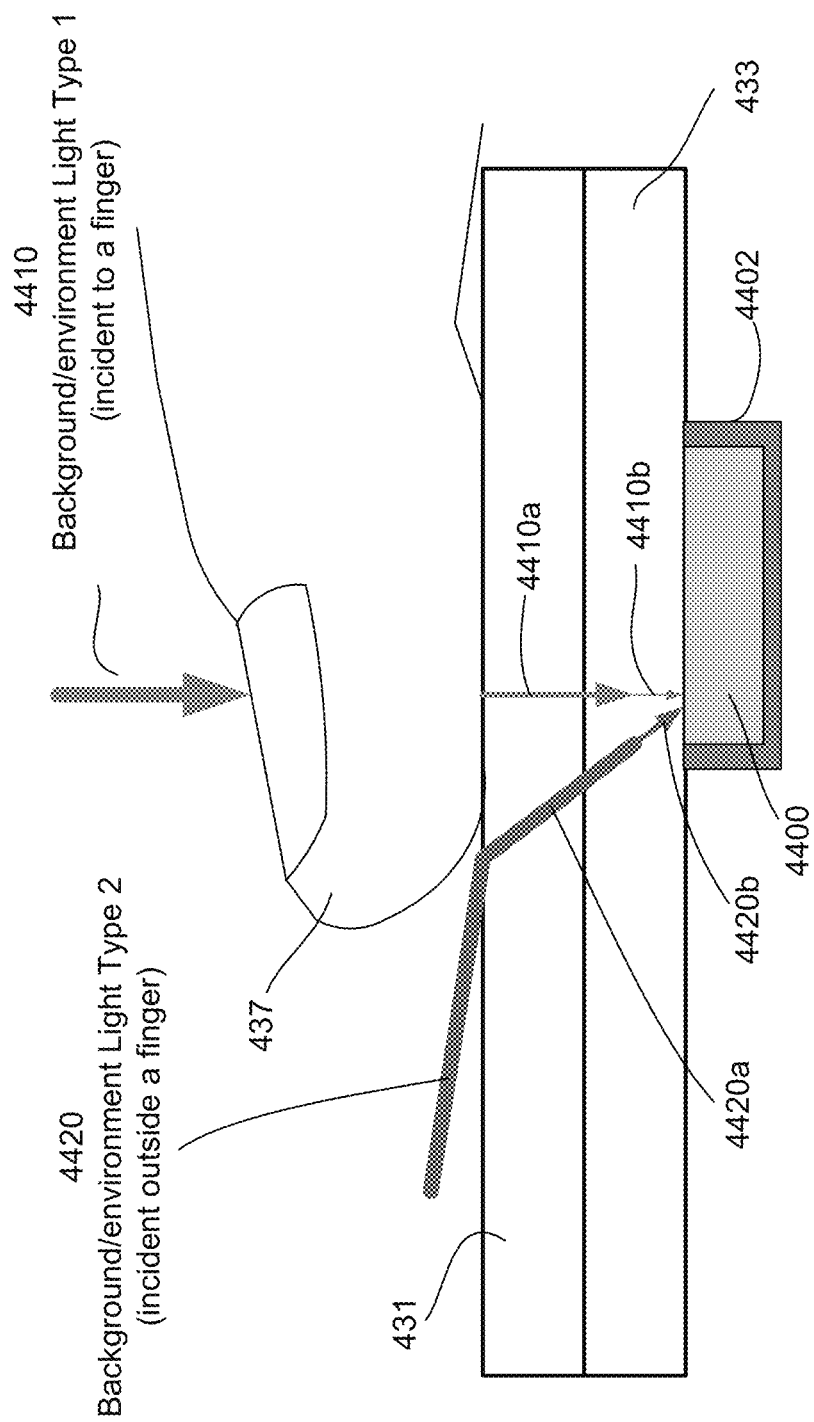
FIG. 44 illustrates influences of the background light in an example of an under-screen optical sensor module.

FIG. 44 illustrates influences of the background light in an under-screen optical sensor module 4400. The undesired environmental light that can adversely affect the optical fingerprint sensing may pass through different paths to reach the optical fingerprint sensor 4400: some environmental light (e.g., light rays 4410) passes through the finger to enter the optical fingerprint sensor 4400 (Type 1) via the top transparent layer 431 (e.g., light rays 4410*a*) and the LCD module 433 (e.g., light rays 4410*b*), and some environment light (e.g., light rays 4420) does not pass through the finger but enters the optical fingerprint sensor 4400 from one or more sides around the finger (Type 2) such as light rays 4420*a* in the top transparent layer 431 and light rays 4420*b* in the LCD module 433.

In the illustrated under-screen optical sensor module 4400 for fingerprint sensing, a sensor package or housing 4402 can be formed outside the under-screen optical sensor module 4400 and may include an optical opaque or absorptive material as a background light blocker, at least for some of incident background light incident at large angles that does not pass through the finger but enters the optical fingerprint sensor 4400 from one or more sides around the finger.

With respect to the Type 1 environmental light 4410 that propagates through the finger, the finger absorbs some of the incident light 4410 so that part of the Type 1 light 4410*a* transmits through the finger to reach the cover glass 431, and subsequently transmits through the cover glass 431 to reach the LCD layers in the LCD module 433. A portion of such Type 1 light 4410*b* passes through LCD layers to enter the optical fingerprint sensor package 4400/4402 and tends to include incident environmental light at large incident angles.

The optical fingerprint sensor package 4402 can be designed to spatially block some of the incident environment light 4420*b* at large angles from entering the optical fingerprint sensor 4400 by providing an optical window on the top to receive mostly incident light from above the optical window formed by the sensor package 4402 so that only the top side of the optical sensor module 4400 that is engaged to (e.g., being glued) the bottom of the LCD module 433 is open to receive light and the sensor bottom and side walls are not optically transparent so that the environmental light that can enter the optical fingerprint sensor is reduced. Therefore, for the environmental light that enters into the optical sensor module without first transmitting through the finger (e.g., the Type 2 environmental light), the packaging of the optical sensor module can be designed to provide absorption or blockage of such light with light blocking side walls or properly designed optical receiving aperture so that such light, when reaching to the receiving optics material or the package material, is absorbed or blocked.

The undesired environmental light can include different wavelength components and thus such different environmental light components can be handled differently to reduce their impacts to the optical fingerprint sensing in implementing the disclosed technology. For example, the undesired environmental light may include (1) light components that transmit through the finger in the red (e.g., longer than 580 nm) and longer wavelengths (e.g., infrared light) and (2) light components that do not transmit through the finger in the shorter wavelengths than the red wavelengths (e.g., less than 580 nm). Due to the wavelength-dependent absorption of the finger shown in FIG. 43, the transmitted environmental light through the finger usually includes some near IR and partial of the red light component. Therefore, the optical filtering can be included in the optical fingerprint sensor package to filter out the undesired environmental light that would otherwise enter the optical detector array.

An example design is to use one or more IR blocking filter coatings, e.g., an IR-cut filter coating, to reduce the IR or near IR light in the transmitted light from the finger. However, various IR-cut filters used for imaging devices normally only restrict wavelengths greater than 710 nm. When a device is exposed to direct or indirect sunlight, this filtering performance may not be good enough for reducing IR background light in optical fingerprint sensing. Suitable IR filtering coatings should extend the short end cut-off wavelength to shorter wavelengths below 710 nm, for example, 610 nm, in some applications.

Due to the spectral responses of various IR blocking or cut coatings, a single IR cut filter with an extended working band to shorter wavelengths may not provide the desired IR blocking performance. In some filter designs for the under-screen optical sensor module, two or more optical filters may be used in combination to achieve the desired IR blocking performance in the sensor light paths. This use of two or more filters is in part because one significant technical issue is the strong background light from the natural day light from the sun. In the examples of disclosed optical sensors under the LCD module, an optical filtering mechanism can be built into the under-screen optical sensor stack to block or reduce the strong background light from the natural day light from the sun that enters the optical detector array 600a. Accordingly, one or more optical filter layers may be integrated into the under-screen optical sensor stack above the optical detector array to block the undesired background day light from the sun while allowing the illumination light for the optical fingerprint sensing to pass through to reach the optical detector array.

For example, in some implementations, the one or more optical filters for reducing the undesired IR environmental/background light can be placed between the LCD module and the optical detector array to be optically transmissive to returned probe light (e.g., probe light between 400 nm and 650 nm or at other probe wavelengths) while blocking light with optical wavelengths longer than 650 nm, including the strong IR light in the day light. In practice, some commercial optical filters have transmission bands that may not be desirable for this particular application for under screen optical sensors disclosed in this document. For example, some commercial multi-layer bandpass filters may block light above 600 nm but would have transmission peaks in the spectral range above 600 nm, e.g., optical transmission bands between 630 nm and 900 nm. Strong background light in the day light within such optical transmission bands can pass through to reach the optical detector array and adversely affect the optical detection for optical fingerprint sensing. Those undesired optical transmission bands in such optical filters can be eliminated or reduced by combining two or more different optical filters together with different spectral ranges so that undesired optical transmission bands in one filter can be in the optical blocking spectral range in another optical filter in a way that the combination of two or more such filters can collectively eliminate or reduce the undesired optical transmission bands between 630 nm to 900 nm. Specifically, for example, two optical filters can be combined by using one filter to reject light from 610 nm through 1100 nm while transmitting visible light below 610 nm in wavelength and another filter to reject light in a shifted spectral range from 700 nm through 1100 nm while transmitting visible light under 700 nm in wavelength. This combination of two or more optical filters can be used to produce desired rejection of the background light at optical wavelengths longer than the upper transmission wavelength. Such optical filters may be formed as coatings at various locations between the LCD module and the optical sensor module.

In some implementations, when using two or more optical filters as disclosed above, an optical absorbing material can be filled between the two filters to exhibit proper absorption for the rejected light band so that the bouncing light between the two optical filters can be absorbed. For example, a piece of blue glass that has high absorption from 610 nm to 1100 nm can be used as a base of the filters and the two filters are coated on up and down surfaces of the blue glass, and this component can be used as the spacer or the protection material above the optical sensor module.

In addition to using proper optical filtering for cutting background light in the red and IR ranges in an under-screen optical sensor module, the background light may include light in the shorter wavelength spectral ranges including the UV wavelengths. In some implementations, the environmental light in the UV band should be reduced or eliminated because this band of light generates noise for the optical sensing. This UV elimination can be realized by using one or more UV-cut optical coatings or by a UV-absorbing material in the probe light path above the optical sensor module. Finger tissues, silicon, and black oil ink and others tend to absorb the UV light strongly. The material absorption of UV light can be used to reduce the UV light influence to the optical fingerprint sensing.

Figure 45:
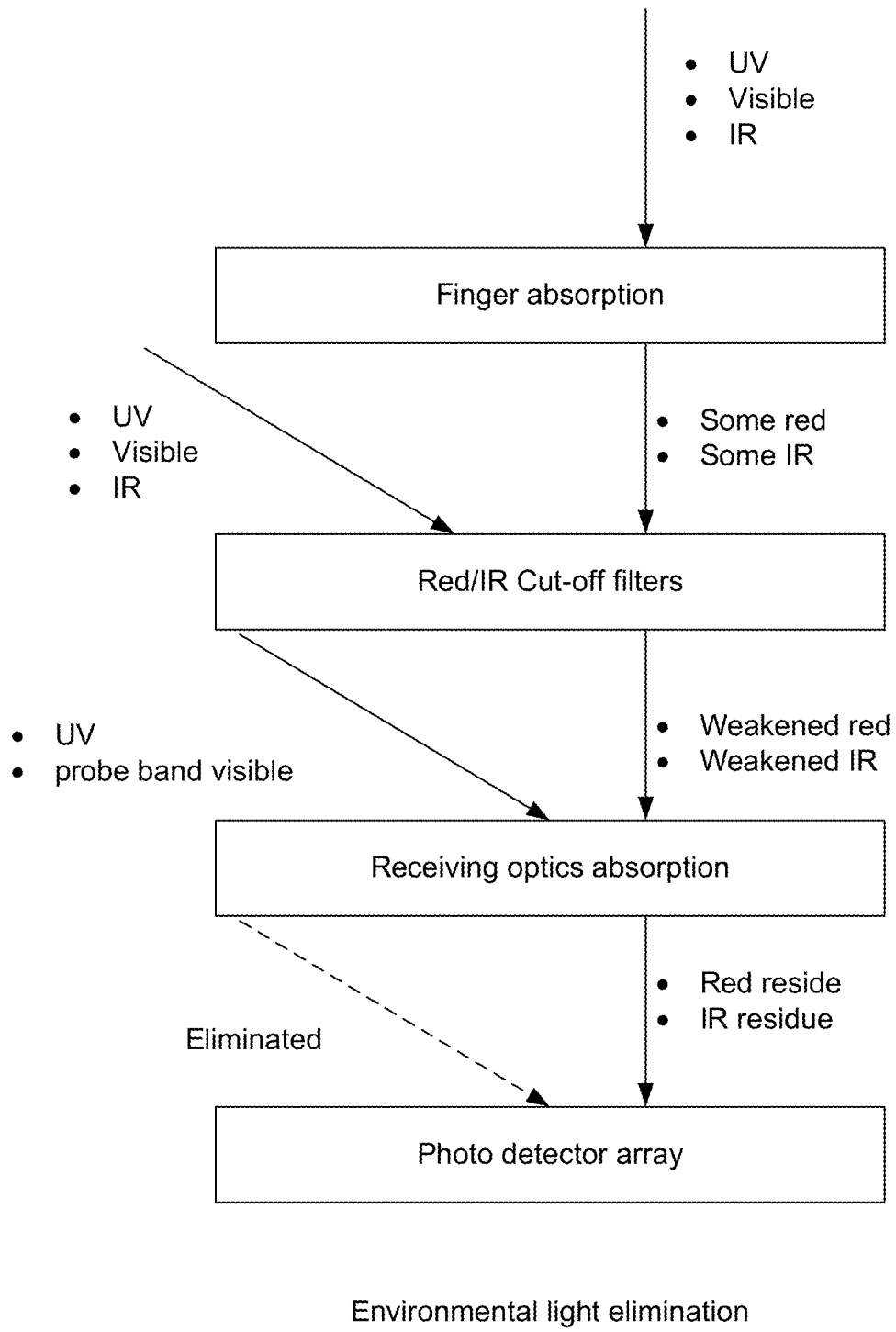
FIG. 45 shows an example of a design algorithm for designing the optical filtering in an under-screen optical sensor module to reduce the impact of the background light in optical sensing.

FIG. 45 shows an example of a design algorithm for designing the optical filtering in an under-screen optical sensor module in light of the above discussions for reducing background light. Hence in addition to designing proper optical filters in the optical path to the optical sensor module, additional design features for reducing the background light can be added to the design of the receiving optics for the optical detector array in the optical sensor module. Those optical filtering considerations and the further background light reduction via operation control and signal processing in operating such an optical sensor module can be combined to achieve the desired optical sensing performance.

Figure 46:
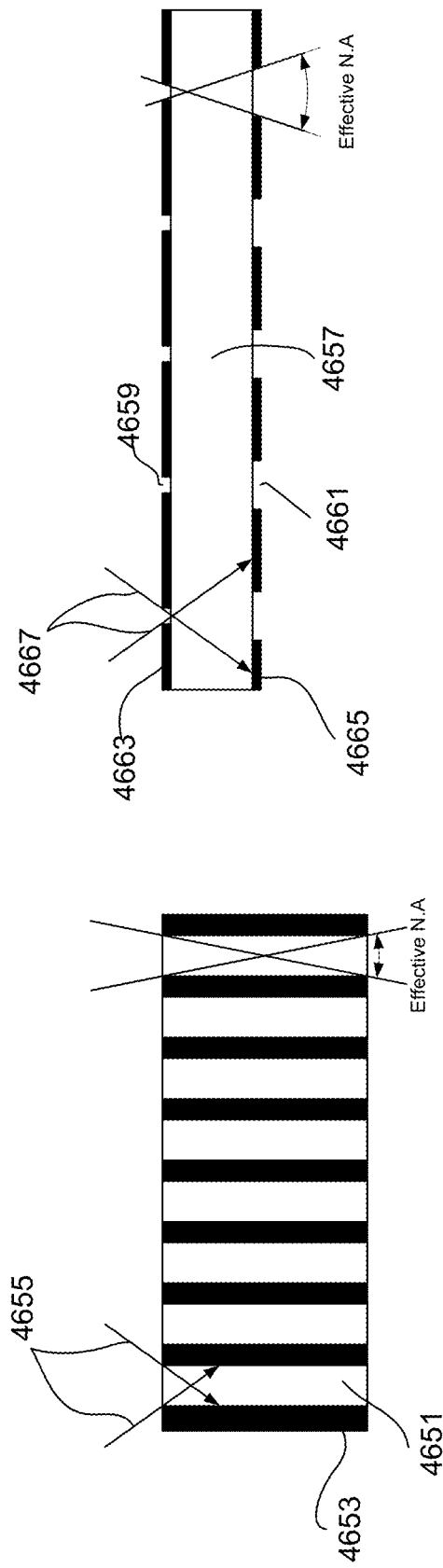
FIG. 46 shows two examples in FIGS. 46A and 46B for an under-screen optical sensor module having an optical collimator array or an optical pinhole array before the optical detector array as part of the receiving optics with a small optical numerical aperture to reduce the background light that enters the optical detector array.

In an under-screen optical sensor module having an optical collimator array or an optical pinhole array before the optical detector array, the optical collimator array or optical pinhole array is part of the receiving optics and can be designed with a small optical numerical aperture to reduce the background light that enters the optical detector array. FIG. 46 shows two examples in FIGS. 46A and 46B.

Referring to FIG. 46A, the collimator pinhole 4651 can be designed to be optically transparent within the probe light band, the collimator wall materials 4653 can be selected to absorb the light 4655 that reaches the wall. If the collimator material is silicon, a blackened, light absorbing coating can be formed on each wall.

Referring to FIG. 46B, the pinhole array of pinholes 4659 as part of the receiving optics can be constructed to have an effective numeral aperture to block the environmental light with large incident angles. A light blocking layer with an array of aperture restriction holes 4661 may be formed below the array of the pinholes 4659 so that the light 4667 out of the effective numeral aperture can be blocked by the opaque section of the light blocking layer with the aperture restriction holes 4661. The materials 4663 and 4665 that form the imaging camera pinholes 4659 and the aperture restriction holes 4661 can an optically opaque material or optically absorbing material such as a black oil ink, or an optical reflection material such as a metal film.

In some implementations, one or more optical filters may be used as the substrate for supporting the pinhole camera type optics so that multiple functional parts can be combined or integrated into one piece of hardware. This integration or combination of different background light reduction mechanism can reduce the device cost and may also reduce the device thickness.

Figure 47:
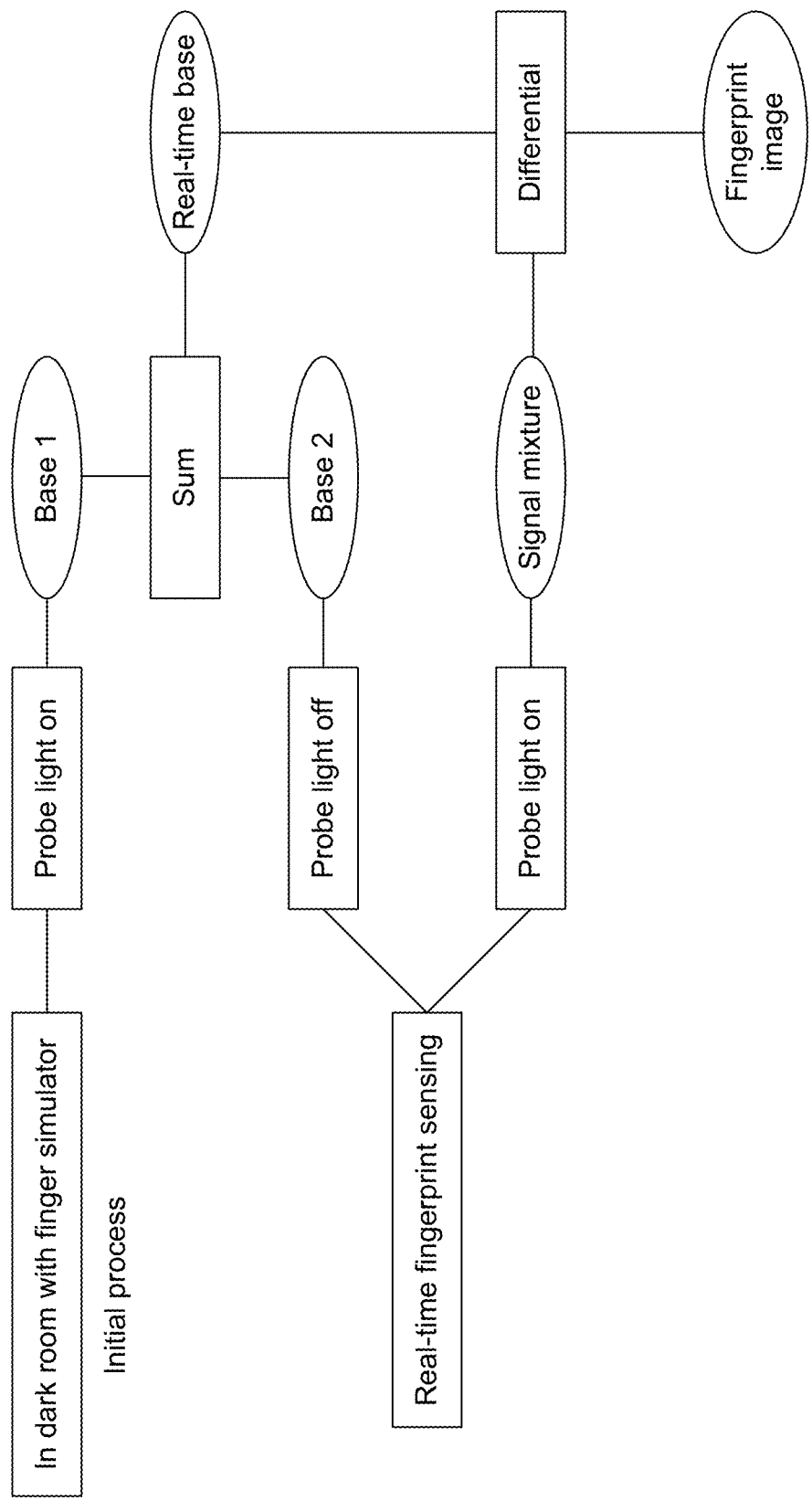
FIG. 47 illustrates an example of a sensor initialization process that measures a baseline background level at the optical detector array each time a fingerprint is obtained.

An under-screen optical sensor module may also be operated with a sensor initialization process to reduce undesired influences of the background light. Like the techniques shown in FIGS. 12 and 13, this sensor initialization process is operational in nature. FIG. 47 illustrates an example of this sensor initialization process that measures a baseline background level at the optical detector array each time a fingerprint is obtained. Before preforming the actual fingerprint sensing, in a dark room environment without any environmental light influence, the illumination light or the optical probe light for the optical sensing is turned on, a finger simulator device is placed on the cover glass to record the image data. The finger simulator device is designed to simulate the finger skin reflection behavior but does not have any fingerprint pattern. This image data obtained from the finger simulator device is saved into memory as the base 1 data for the background light reduction processing in real sensing operations. This process can be a device calibration process done in factory before shipping the device.

In real time fingerprint sensing, the environmental influence is present. In operation, the illumination light or the optical probe light is first turned off to record the image data as base 2, which is made under a condition with the environmental light. This base 2 represents the total influence of all the environmental light residues. The sum of base 1 and base 2 gives the real-time base. Next, the illumination light or optical probe light is turned on to perform fingerprint sensing to capture a real-time signal which is a mixture of the real fingerprint signal from the fingerprint and the real-time base. A differential between the signal mixture and the real-time base can be performed as part of the signal processing to reduce the signal contribution by the environmental light so that the image quality of the fingerprint image can be obtained.

The above example in FIG. 47 illustrates a method for operating an electronic device capable of detecting a fingerprint by optical sensing by operating an optical sensor module located below a touch display panel, that provides touch sensing operations for the device, to produce probe light to the illuminate a top transparent layer of the touch display panel to operate an optical detector array inside the optical sensor module to obtain a first image from returned probe light from the top transparent layer. This method includes operating the optical detector array inside the optical sensor module, while turning off the probe light, to obtain a second image under illumination with only environmental light without illuminating the top transparent layer of the touch display panel with any probe light; and processing the first image and the second image to remove an effect from the environmental light in an imaging operation of the device.

Based on the above, the undesired effect of the background light to the performance of the under-screen optical sensor module can be mitigated in different techniques, including implementing optical filtering in the optical path to the optical detector array to reduce the background light, designing the receiving optics for the optical detector array to reduce the background light, or controlling the operations of the optical sensor module and signal processing to further reduce the effect of the background light to the optical sensing performance. Those different techniques may be used individually or in combination to meet the desired device performance.

The above examples of techniques for reducing the background or environmental light are generally based on blocking or filtering out the background or environmental light from reaching the under-LCD optical sensor module. However, a portion of the background light that transmits through a finger to reach the top glass surface at a fingerprint sensing region may carry the fingerprint information and thus can be used to fingerprint sensing. Referring back to FIG. 44 where the Type 1 background light rays 4410*b* that transmit though the finger and a portion of such background rays 4410*b* at the top of the optical sensor module 4400 are in optical wavelengths between 650 nm and 950 nm as shown in FIG. 43. The background rays 4410*b* at the top of the optical sensor module 4400 can be detected for optical fingerprint sensing because the background light between 650 nm and 950 nm can transmit into the finger tissues and propagate through the stratum corneum of the finger skin to be imprinted with the fingerprint information by the internal structural variations inside the finger skin caused by the fingerprint ridge area and valley area and such internal structural variations manifest light signals with different brightness and this brightness contrast as a fingerprint pattern caused by the finger tissue absorption, refraction, and reflection, by finger skin structure shading, and/or by optical reflectance difference at the finger skin.

This technique of using transmitted light between 650 nm and 950 nm through finger tissues to obtain the fingerprint information is different from the technique based on reflected light caused by the surface topographical pattern formed by the finger ridges and valleys outside the finger as illustrated in FIGS. 5A, 5B and 5C. When relying on the surface reflection at a finger shown in FIGS. 5A, 5B and 5C, the presence of water or sweat ("wet finger contact conditions") or other materials such as dirty or debris ("dirty finger contact conditions") between the finger and the top glass surface can change the optical reflection and cause undesired variations in the image contrast, thus adversely impacting the fingerprint sensing performance. In contrast, one of the advantages of using the optical transmitted light for obtaining the fingerprint pattern via finger internal structural variations is that the optical fingerprint sensing is less sensitive to the surface contact condition of a finger in contact with the top glass surface in comparison with the optical fingerprint sensing based on the reflected light caused by the surface topographical pattern formed by the finger ridges and valleys outside the finger as illustrated in FIGS. 5A, 5B and 5C.

There are technical challenges in using such background light for optical fingerprint sensing. For example, the background light can be strong such as the sunlight and can saturate the optical detectors in the optical sensor array 4400. It is recognized that, however, devices with LCD displays may also be structured such as the LCD layers with the liquid crystal cells to exhibit certain optical transmission properties to facilitate mitigation of the adverse impact of the background or environmental light in the under-LCD optical sensing while using the background rays 4410*b* at the top of the optical sensor module 4400 in the optical wavelengths between 650 nm and 950 nm for fingerprint sensing. For example, LCD layers with the front and back optical polarization layers on two opposite sides of the LC cell layers may be designed to selectively block or reduce optical transmission of certain background light in the visible and UV spectra ranges from reaching the under-LCD optical sensor module while allowing a portion of the background rays 4410*b* at the top of the optical sensor module 4400 in the optical wavelengths between 650 nm and 950 nm for fingerprint sensing. As a specific example, LCD layers with the front and back optical polarization layers on two opposite sides of the LC cell layers may be designed to block the visible light or the light at wavelengths shorter than 650 nm when the LC cells are turned to the off mode to block optical transmission while still transmitting for light at longer wavelengths, such as 800 nm or longer. This operation of the LCD module in the non-transmission off mode at the LC cells can be used to reduce the total amount of the background light from reaching the optical sensor module 4400 while allowing the optical sensor module 4400 to use the a portion of the fingerprint-carrying background light 440*b* for optical sensing. Under this design, the probe light sources 436*a* for optical sensing should be designed to emit probe light in the longer wavelength range where the LC cells in the off mode to block optical transmission can still be transparent to allow transmission of light at longer wavelengths, such as 800 nm or longer. For example, the probe light sources 436*a* for optical sensing can be designed to emit probe light at 850 nm in order to pass through the LCD layers in the off mode to illuminate the finger and to return back to the optical sensor module 4400 by pass through the LCD layers in the off mode. With this design, when the optical sensor module 4400 and probe light module 436*a* are activated for fingerprint detection or other optical sensing, the LCD pixels in the corresponding fingerprint sensing area of the peripheral display zone 20 or the task bar can be turned off so that the liquid crystal material and the reflector film block the visible light band and part of the light in the near IR band. This improves the total amount of the signal light that carries the fingerprint information while reducing the amount of the background light at the optical sensor module 4400.

In general, for under-LCD optical sensing, the probe light sources 436*a* for optical sensing can designed to emit probe light in the longer wavelength range between 650 nm and 950 nm for fingerprint sensing to allow optical transmission through finger tissues, such as 800 nm or longer, so that both (1) the transmitted light for obtaining the fingerprint pattern via finger internal structural variations as explained above and (2) the reflected probe light caused by the surface topographical pattern formed by the finger ridges and valleys outside the finger as illustrated in FIGS. 5A, 5B and 5C may be used for optical fingerprint sensing. For example, the probe light sources 436*a* for optical sensing can be designed to emit probe light at 850 nm to obtain the fingerprint information based on the two mechanisms to reduce the impact by undesired wet or dirty finger contact conditions due to the presence of the transmitted probe light at the optical sensor module.

FIG. 48 shows an example of a device using an under-LCD optical sensor module based on probe light between 650 nm and 950 nm for fingerprint sensing that can transmit through finger tissues. Two different probe light sources 436*a* and 4661 are provided at two different locations for optical sensing on the top glass cover 431 and are specifically designed to produce the probe light at the same probe wavelength between 650 nm and 950 nm for fingerprint sensing. The first probe light source module 436*a* is located adjacent or the optical sensor module 4820 under the LCD module 433 to produce first probe light directed to the fingerprint sensing area on the top glass cover 431 upward at relatively small incident angles to produce the reflected probe light signal as illustrated in FIGS. 5A, 5B and 5C. This first probe light also produces returned probe light caused by a portion of the first probe light that transmits into the finger. This portion of the first probe light inside the finger is scattered back by the finger tissues and passes through the finger once more time to be imprinted with the fingerprint pattern via transmitting through the finger surface in contact with the top glass cover 431. These two portions of the first probe light are directed by the receiving optics of the optical sensor module 4820 to the optical detector array for optical sensing. The first probe light is not illustrated in FIG. 48.

The second probe light source module 4661 is located under the top glass cover 431 but is away from the fingerprint sensing area on the top glass cover 431 such that it produces and directs second probe light 4661*a* to the fingerprint sensing area on the top glass cover at large incident angles so largely the optical reflection of the second probe light at the surface does not enter into the optical sensor module 4820. However, a portion of the second probe light 4661*a* at the surface transmits into the finger and this portion of the second probe light 4661*a* inside the finger is scattered back as light 4661*b* by the finger tissues and passes through the finger once more time to be imprinted with the fingerprint pattern via transmitting through the finger surface in contact with the top glass cover 431. This signal probe light 4661*b* caused by the second probe light 4661 is directed by the receiving optics of the optical sensor module 4820 to the optical detector array for optical sensing.

Therefore, the optical sensor module 4820 not only receives probe light signals from two different probe light sources but also receives the same fingerprint pattern information from two types of light-finger interactions: (1) the surface reflection by the finger's bridges and valleys and (2) the interaction by the internal structures of the finger associated with the finger's bridges and valleys. This produces an improved optical sensing in devices with LCD panels structured to provide the main and peripheral display zones in the same LCD panel or devices with LCD panels structured as a single-zone display.

Figure 49:
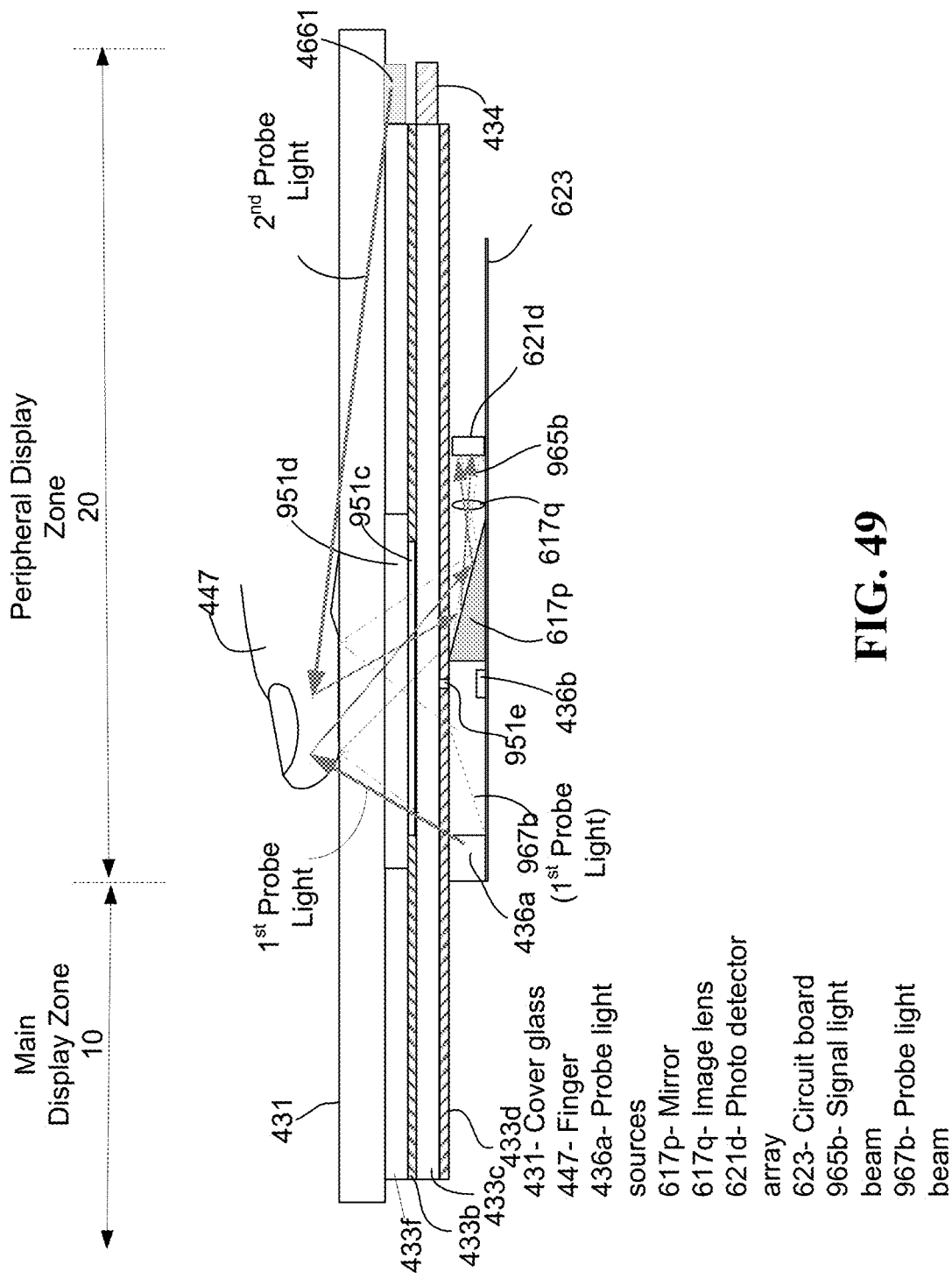
FIG. 49 shows a particular example for implementing the probe light design in FIG. 48 to the device example in FIG. 42 with a LCD display structured to provide the main and peripheral display zones and by using two different probe light sources at two different locations to produce probe light that can transmit through finger tissues for optical sensing.

FIG. 49 shoes a particular example for implementing the probe light design in FIG. 48 to the device example in FIG. 42 with a LCD display structured to provide the main and peripheral display zones in the same LCD panel. Two different probe light sources 436*a* and 4661 are provided in the device example in FIG. 42 with the mirror 617*p* and the lens 617*q* as part of the receiving optics for optical sensing and the light sources 436a and 466l. The first probe light source module 436a is located adjacent or the optical sensor module 4820 under the LCD module 433 to produce two types of probe light signals: (1) the reflected probe light signal (in dashed lines) from the finger external surface as explained and marked in FIG. 42 and (2) the returned probe light signal (in solid lines) caused by the probe light transmitted into the finger and is scattered back to transmit through the finger to enter the receiving optics (mirror 617p and the lens 617q) and the optical detector array 621d. The second probe light source module 466l is located side by side with the LCD module 433 under their common top glass cover 431 to produce the second probe light at large incident angles at the sensing area to transmit into the finger and is scattered back to transmit through the finger to enter the receiving optics (mirror 617p and the lens 617q) and the optical detector array 621d. The optical reflection of the second probe light from the second probe light source module 466l is not depicted in FIG. 49 and the probe signal caused by scattering inside the finger is shown in solid lines.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An electronic device capable of detecting a fingerprint by optical sensing, comprising:
a liquid crystal display (LCD) screen that provides touch sensing operations and includes a LCD display panel structure to display images, wherein the LCD display screen includes (1) a main display zone having LCD display pixels and a peripheral display zone having LCD display pixels wherein the main display zone and peripheral display zone collectively form a seamless contiguous LCD display area, and (2) a LCD backlighting module that provides backlighting light to illuminate both the main display zone and peripheral display zone;
a designated peripheral display zone illumination module located relative to the LCD screen and structured to produce and direct illumination light only to the peripheral display zone to enable the peripheral display zone to display images or information independently from the main display zone and to be operable to display images or information when the LCD backlighting module is turned off;
a top transparent layer formed over the LCD screen as an interface for being touched by a user for the touch sensing operations and for transmitting the light from LCD screen to display images or information to a user; and
an optical sensor module located below the LCD display panel structure and structured to receive probe light that is from an object in contact with or near the peripheral display zone and passes through the LCD screen to detect a fingerprint.

2. The device as in claim 1, comprising:
a control module coupled to the main display zone, peripheral display zone, the LCD backlighting module and the designated peripheral display zone illumination module to enable the designated peripheral display zone illumination module to illuminate the peripheral display zone to display images when the LCD backlighting module is turned off.

3. The device as in claim 2, wherein:
the control module is structured to control the peripheral display zone to display a fingerprint sensing zone in the peripheral display zone for a user to place a finger for fingerprint sensing by the optical sensor module.

4. The device as in claim 2, wherein:
the control module is structured to control the peripheral display zone to display a message independent of whether the main display zone is turned on or not.

5. The device as in claim 2, wherein:
the control module is structured to control the peripheral display zone to display an icon that allows a user to launch an app or perform a function by touching the icon independent of whether the main display zone is turned on or not.

6. The device as in claim 2, wherein:
the control module is structured to control the peripheral display zone to display information independent of whether the main display zone is turned on or not.

7. The device as in claim 2, wherein:
the control module is structured to control the peripheral display zone to display a group of icons at different positions in the peripheral display zone independent of whether the main display zone is turned on or not, wherein an icon allows a user to launch an app or perform a function by touching the icon.

8. The device as in claim 7, wherein:
the control module is structured to control, independent of whether the main display zone is turned on or not, the peripheral display zone to display different groups of icons in the peripheral display zone by allowing one group of icons to be displayed at a time while enabling a user to slide a finger in the peripheral display zone to use another group of icons to replace the currently displayed group of icons.

9. The device as in claim 1, wherein:
the designated peripheral display zone illumination module is located within the LCD display panel structure and above the optical sensor module within the peripheral display zone.

10. The device as in claim 1, wherein:
the designated peripheral display zone illumination module is located below the LCD display panel structure within the peripheral display zone.

11. The device as in claim 10, wherein:
the designated peripheral display zone illumination module is located below the peripheral display zone of the LCD display panel structure and near the optical sensor module.

12. The device as in claim 10, wherein:
the LCD display panel structure includes a light diffuser layer that diffuses light and a light reflector layer for redirecting illumination light in the LCD display panel structure back to LCD pixels for displaying operations,
each of the light diffuser and the light reflector layer includes holes or passages at a selected area above the optical sensor module and the designated peripheral display zone illumination module to allow light to be transmitted to reach the optical sensor module and to allow light from the designated peripheral display zone illumination module to illuminate LCD pixels in the peripheral display zone of the LCD display panel structure.

13. The device as in claim 10, wherein:
the LCD display panel structure includes a light diffuser layer that diffuses light and a light reflector layer for redirecting illumination light in the LCD display panel structure back to LCD pixels for displaying operations,
each of the light diffuser and the light reflector layer includes a modified region at a selected area different from other parts of the light diffuser or the light reflector layer above the optical sensor module and the designated peripheral display zone illumination module to allow light to be transmitted to reach the optical sensor module and to allow light from the designated peripheral display zone illumination module to illuminate LCD pixels in the peripheral display zone of the LCD display panel structure.

14. The device as in claim 10, further comprising:
one or more probe light sources that produce probe light, a portion of which passes through the LCD screen to illuminate a sensing area on the top transparent layer above the LCD screen,
the optical sensor module includes an optical detector array of optical detectors located to receive the probe light that is directed back from the top transparent layer for optical sensing, and
wherein the designated peripheral display zone illumination module is placed near the one or more probe light sources below the LCD display panel structure.

15. The device as in claim 14, wherein:
the designated peripheral display zone illumination module is located between the one or more probe light sources and the optical detector array of the optical sensor module.

16. The device as in claim 1, wherein:
the optical sensor module includes an optical detector array of optical detectors located to receive the probe light that is directed back from the top transparent layer for optical sensing; and
the optical sensor module includes a lens that collects the probe light that is directed back from the top transparent layer for optical sensing and directs the collected probe light onto the optical detector array.

17. The device as in claim 16, wherein:
the optical sensor module includes an optical reflector located in an optical path of the probe light from the top transparent layer to the lens to reflect the probe light from the top transparent layer towards the lens.

18. The device as in claim 1, wherein:
the optical sensor module includes an optical detector array of optical detectors located to receive the probe light that is directed back from the top transparent layer for optical sensing; and
the optical detector array in the optical sensor module is located to collect the probe light without a lens.

19. The device as in claim 1, wherein:
the optical sensor module located below the LCD display panel structure is configured such that at least part of the optical sensor module is located below the peripheral display zone, the optical sensor module structured to receive probe light that is from an object in contact with or near the peripheral display zone and passes through the LCD screen to detect a fingerprint.

20. The device as in claim 1, wherein:
the optical sensor module includes an optical collimator array of optical collimators that receives the probe light and an optical detector array of optical sensors to receive the probe light from the optical collimator array for optical sensing.

21. The device as in claim 20, wherein:
the top transparent layer includes a designated fingerprint sensing region for a user to touch with a finger for fingerprint sensing;
the optical sensor module below the LCD display panel structure includes a transparent block in contact with the display panel substrate to receive light from the LCD display panel structure and returned from the top transparent layer, wherein the optical sensor module is positioned relative to the designated fingerprint sensing region and structured to selectively receive returned light via the optical collimator array from the top surface of the top transparent layer when in contact with a person's skin.

22. The device as in claim 21, wherein:
the LCD display panel structure includes a light diffuser layer that diffuses light and the light diffuser includes holes or passages at a selected area above the optical sensor module to allow light to be transmitted to reach the optical sensor module.

23. The device as in claim 21, wherein:
the LCD display panel structure includes a light reflector layer for redirecting illumination light in the LCD display panel structure back to LCD pixels for displaying operations and the light reflector layer includes holes or passages at a selected area above the optical sensor module to allow light to be transmitted to reach the optical sensor module.

24. The device as in claim 1, wherein:
the LCD display panel structure includes a light diffuser layer that diffuses light and the light diffuser includes holes at a selected area above the optical sensor module to allow light to be transmitted to reach the optical sensor module, and an optical reflector layer formed on a bottom region of the LCD display panel structure to reflect light back to the LCD display panel structure, wherein the optical reflector layer includes a selected area above the optical sensor module to allow light to be transmitted to reach the optical sensor module.

25. The device as in claim 1, comprising:
a device electronic control module coupled to the display panel structure to supply power to the one or more probe light sources to turn off power to the one or more probe light sources in a sleep mode,
wherein the device electronic control module is configured to wake up the LCD display panel structure from the sleep mode when the optical sensor module detects the presence of a person's skin at the designated fingerprint sensing region of the top transparent layer.

26. The device as in claim 25, wherein:
the device electronic control module is configured to operate one or more probe light sources to intermittently emit the probe light, while turning off power to the LCD display panel structure, when the LCD display panel structure is in the sleep mode, to direct the intermittently probe light to the designated fingerprint sensing region of the top transparent layer for monitoring whether there is a person's skin in contact with the designated fingerprint sensing region for waking up the device from the sleep mode.

27. The device as in claim 1, further comprising:
a device electronic control module that grants a user's access to the device if a detected fingerprint matches a fingerprint an authorized user.

28. The device as in claim 27, wherein:
the optical sensor module is configured to, in addition to detecting fingerprints, also detect a biometric parameter different form a fingerprint by optical sensing to indicate whether a touch at the top transparent layer associated with a detected fingerprint is from a live person, and
the device electronic control module is configured to grant a user's access to the device if both (1) a detected fingerprint matches a fingerprint an authorized user and (2) the detected biometric parameter indicates the detected fingerprint is from a liver person.

29. The device as in claim 28, wherein:
the biometric parameter includes a heartbeat.

30. The device as in claim 28, wherein:
the biometric parameter includes different optical absorption properties of living human tissues at different probe wavelengths.

31. The device as in claim 1, comprising:
a device electronic control module coupled to the optical sensor module to receive information on multiple detected fingerprints obtained from sensing a touch of a finger, wherein the device electronic control module measures a change in the multiple detected fingerprints and determines a touch force that causes the measured change.

32. The device as in claim 31, wherein:
the change includes a change in the fingerprint image due to the touch force, a change in the touch area due to the touch force, or a change in spacing of fingerprint ridges.

33. The device as in claim 1, wherein:
the LCD display panel structure includes a peripheral display zone illumination waveguide covering a region of the peripheral display zone and optically coupled to receive illumination light from the designated peripheral display zone illumination module, and
the peripheral display zone illumination waveguide is structured to distribute the illumination light to illuminate the peripheral display zone only.

34. The device as in claim 1, comprising:
one or more probe light sources located relative to the peripheral display zone to produce the probe light within an optical spectral range that can transmit through finger tissues to enter a finger to cause both reflected probe light from a finger surface and returned probe light caused by scattering inside the finger towards the optical sensor module located below the LCD display panel structure.

35. The device as in claim 34, wherein:
the probe light is at a wavelength between 650 nm to 950 nm.

36. The device as in claim 34, wherein:
the probe light is at a wavelength between 800 nm to 950 nm.

37. The device as in claim 1, comprising:
a first probe light source located under the LCD panel structure near the optical sensor module within the peripheral display zone to produce first probe light, as part of the probe light, at a probe wavelength within an optical spectral range that can transmit through finger tissues to enter a finger, to cause both first reflected probe light from a finger surface and first returned probe light caused by scattering inside the finger towards the optical sensor module located below the LCD display panel structure; and
a second probe light source located outside the LCD panel structure and under the top transparent layer to produce second probe light within the optical spectral range to enter a finger to cause second returned probe light caused by scattering inside the finger towards the optical sensor module located below the LCD display panel structure,
wherein the optical sensor module detects a combination of the first reflected probe light, the first returned probe light and the second returned probe light for fingerprint sensing.

38. An electronic device capable of detecting a fingerprint by optical sensing, comprising:
a liquid crystal display (LCD) display panel structure to display images or information and to provide touch sensing operations, the LCD display panel structure including LCD layers to display images or information by processing illumination backlighting light in a main display zone and a peripheral display zone which collectively form a seamless contiguous LCD display area, a light diffusion layer that diffuses the illumination backlighting light in the main display zone and peripheral display zone, a waveguide layer that receives the illumination backlighting light and directs the received illumination backlighting light to the main display zone and peripheral display zone, and a light reflector layer for redirecting illumination backlighting light in the LCD layers of the main display zone and peripheral display zone for displaying operations, each of the light diffuser and the light reflector layer structured to include holes or passages at a selected area in the peripheral display zone of the LCD display panel structure to allow light to be transmitted, and
a LCD backlighting light module coupled to the waveguide layer of the LCD display panel structure to produce backlighting light to the LCD layers for displaying images or information;
a designated peripheral display zone illumination module located to produce and direct illumination light only to the peripheral display zone to enable the peripheral display zone to display images or information independently from the main display zone and to be operable to display images or information when the LCD backlighting module is turned off;
a top transparent layer formed over the LCD display panel structure as an interface for being touched by a user for the touch sensing operations;
an optical sensor module located below the LCD display panel structure to receive probe light from the top transparent layer and passes through the LCD display panel structure to detect a fingerprint; and one or more probe light sources, separate from the LCD backlighting light module, located under the top transparent layer, to produce the probe light that illuminates a designated fingerprint sensing area on the top transparent layer in the peripheral display zone for a user to place a finger for optical fingerprint sensing by the optical sensor module.

39. The device as in claim 38, wherein:
the designated peripheral display zone illumination module is located within the LCD display panel structure and above the optical sensor module within the peripheral display zone.

40. The device as in claim 38, wherein:
the designated peripheral display zone illumination module is located below the LCD display panel structure within the peripheral display zone.

41. The device as in claim 40, wherein:
the optical sensor module includes an optical detector array of optical detectors located to receive the probe light that is directed back from the top transparent layer for optical sensing, and
the designated peripheral display zone illumination module is placed near the one or more probe light sources below the LCD display panel structure.

42. The device as in claim 41, wherein:
the designated peripheral display zone illumination module is located between the one or more probe light sources and the optical detector array of the optical sensor module.

43. The device as in claim 38, wherein:
the optical sensor module includes an optical detector array of optical detectors located to receive the probe light that is directed back from the top transparent layer for optical sensing, and
the optical sensor module includes a lens that collects the probe light that is directed back from the top transparent layer for optical sensing and directs the collected probe light onto the optical detector array.

44. The device as in claim 43, wherein:
the optical sensor module includes an optical reflector located in an optical path of the probe light from the top transparent layer to the lens to reflect the probe light from the top transparent layer towards the lens.

45. The device as in claim 38, wherein:
the optical sensor module located below the LCD display panel structure is configured such that at least part of the optical sensor module is located below the peripheral display zone, the optical sensor module structured to receive probe light that is from an object in contact with or near the peripheral display zone and passes through the LCD screen to detect a fingerprint.

46. The device as in claim 38, wherein:
the optical sensor module includes an optical collimator array of optical collimators that receives the probe light and an optical detector array of optical sensors to receive the probe light from the optical collimator array for optical sensing.

47. The device as in claim 38, wherein:
the one or more probe light sources produce the probe light at different optical wavelengths so that the optical sensor module captures optical properties in reflected probe light by an object in contact with the designated fingerprint sensing area on the top transparent layer at the different optical wavelengths, and
the device control module is operable to process the captured optical properties in reflected probe light by the object at the different optical wavelengths to determine whether the object is a finger of a live person.

48. The device as in claim 38, wherein:
the LCD display panel structure includes a peripheral display zone illumination waveguide covering a region of the peripheral display zone and optically coupled to receive illumination light from the designated peripheral display zone illumination module, and
the peripheral display zone illumination waveguide is structured to distribute the illumination light to illuminate the peripheral display zone only.

49. The device as in claim 38, wherein:
each probe light source is structured to produce the probe light within an optical spectral range that can transmit through finger tissues to enter a finger to cause both reflected probe light from a finger surface and returned probe light caused by scattering inside the finger towards the optical sensor module located below the LCD display panel structure.

50. The device as in claim 49, wherein:
the probe light is at a wavelength between 650 nm to 950 nm.

51. The device as in claim 49, wherein:
the probe light is at a wavelength between 800 nm to 950 nm.

52. The device as in claim 38, wherein:
a first probe light source is located under the LCD panel structure near the optical sensor module within the peripheral display zone to produce first probe light, as part of the probe light, at a probe wavelength within an optical spectral range that can transmit through finger tissues to enter a finger, to cause both first reflected probe light from a finger surface and first returned probe light caused by scattering inside the finger towards the optical sensor module located below the LCD display panel structure; and
a second probe light source is located outside the LCD panel structure and under the top transparent layer to produce second probe light within the optical spectral range to enter a finger to cause second returned probe light caused by scattering inside the finger towards the optical sensor module located below the LCD display panel structure,
wherein the optical sensor module detects a combination of the first reflected probe light, the first returned probe light and the second returned probe light for fingerprint sensing.

* * * * *